United States Patent
Baltzer et al.

(10) Patent No.: US 7,795,289 B2
(45) Date of Patent: *Sep. 14, 2010

(54) USE OF ACYLAMINOTHIAZOLE DERIVATIVES AS THERAPEUTIC AGENTS

(75) Inventors: Sylvie Baltzer, Strausbourg (FR); Bruno Schoentjes, Bois-Guillaume (FR); Viviane Van Dorsselaer, Strasbourg (FR)

(73) Assignee: Sanofi-Aventis, Paris (FR)

( * ) Notice: Subject to any disclaimer, the term of this patent is extended or adjusted under 35 U.S.C. 154(b) by 270 days.

This patent is subject to a terminal disclaimer.

(21) Appl. No.: 11/859,443

(22) Filed: Sep. 21, 2007

(65) Prior Publication Data

US 2008/0051436 A1 Feb. 28, 2008

Related U.S. Application Data

(60) Division of application No. 11/035,803, filed on Jan. 14, 2005, now Pat. No. 7,291,636, which is a continuation of application No. PCT/FR03/02194, filed on Jul. 11, 2003.

(30) Foreign Application Priority Data

Jul. 17, 2002 (FR) .................................. 02 09061

(51) Int. Cl.
*A61K 31/426* (2006.01)
(52) U.S. Cl. ....................................... 514/371
(58) Field of Classification Search ................. 514/371
See application file for complete search history.

(56) References Cited

U.S. PATENT DOCUMENTS 5,712,270 A 1/1998 Sabb et al.

7,291,636 B2 * 11/2007 Baltzer et al. ............... 514/371
2004/0152747 A1 8/2004 Chen et al.

FOREIGN PATENT DOCUMENTS

WO WO 98/22430 5/1998

OTHER PUBLICATIONS

Pallàs et al., Current Pharmaceutical Design, (2006), 12(33), pp. 4389-4408.*
Higaki, J., N., et. al., A Combinatorial Approach to the Identification of Dipeptide Aldehyde Inhibitors of B-Amyloid Production, J. Med. Chem. vol. 42, pp. 3889-3898 (1999).
Pallas, M., et. al., Molecular and Biochemical Features in Alzheimer's Disease, Current Pharmaceutical Design (2006) vol. 12, pp. 4389-4408.

* cited by examiner

*Primary Examiner*—Laura L. Stockton
(74) *Attorney, Agent, or Firm*—Balaram Gupta

(57) ABSTRACT

This invention discloses and claims a method of treatment of a disease as defined herein using a compound conforming to the general formula (I):

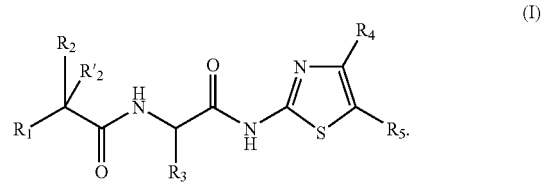

Wherein $R_1$, $R_2$, $R'_2$, $R_3$, $R_4$ and $R_5$ are as described herein. Specifically, the compounds of the present invention exhibit an inhibitory effect on the production of β-amyloid peptide (β-A4) by inhibition of gamma protease. Therefore, the compounds of the present invention are useful in the treatment of pathologies such as senile dementia, Alzheimer's disease, Down's syndrome, Parkinson's disease, amyloid angiopathy and/or cerebrovascular disorders.

6 Claims, No Drawings

USE OF ACYLAMINOTHIAZOLE DERIVATIVES AS THERAPEUTIC AGENTS

This application is a division of U.S. application Ser. No. 11/035,803, filed Jan. 14, 2005, now U.S. Pat. No. 7,291,636, which is a continuation of International application No. PCT/FR2003/002,194, filed Jul. 11, 2003, both of which are incorporated herein by reference in their entirety; which claims the benefit of priority of French Patent Application No. 02/09,061, filed Jul. 17, 2002.

BACKGROUND OF THE INVENTION

Field of the Invention

The present invention relates to acylaminothiazole derivatives, their preparation and their therapeutic use.

SUMMARY OF THE INVENTION

The present invention first provides compounds conforming to the general formula (I):

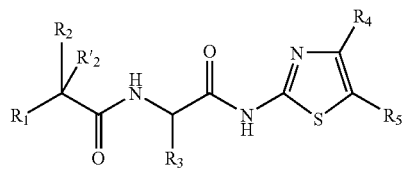

(I)

in which $R_1$ represents:
  a $C_{1-6}$ alkyl optionally substituted by one to three substituents selected from a halogen, a hydroxyl, a trifluoromethyl, a $C_{1-6}$ alkoxy, a $C_{1-6}$ thioalkyl, a thiophene or a phenyl; or
  a $C_{3-7}$ cycloalkyl, a thiophene, a benzothiophene, a pyridinyl, a furanyl or a phenyl;
  the phenyl groups being optionally substituted by one to three substituents selected from a halogen atom, a $C_{1-6}$ alkyl, a $C_{1-6}$ alkoxy, a hydroxyl, a methylenedioxy, a phenoxy or a benzyloxy;

$R_2$ and $R'_2$ represent independently of one another a hydrogen atom, a halogen atom, a hydroxyl, a $C_{1-3}$ alkoxy, a $C_{1-3}$ alkyl, a $C_{3-7}$ cycloalkyl, an O—C(O)—$C_{1-16}$ alkyl group, or $R_2$ and $R'_2$ taken together form an oxo group;

$R_3$ represents a hydrogen atom, a $C_{1-6}$ alkyl optionally substituted by a hydroxyl or a $C_{1-3}$ alkoxy;

$R_4$ and $R_5$ represent independently of one another:
  a hydrogen atom, a $C_{1-7}$ alkyl optionally substituted by a $C_{3-7}$ cycloalkyl or phenyl; or
  a $C_{3-7}$ cycloalkyl, a phenyl, a naphthyl or a —C(X)$R_6$;
  the $C_{3-7}$ cycloalkyl and phenyl groups being optionally substituted by one or more groups selected from a halogen atom, a hydroxyl, a $C_{1-3}$ alkyl, a $C_{1-3}$ alkoxy, a trifluoromethyl, a trifluoromethoxy, a phenyl, a phenoxy, a benzyloxy, a —CH$_2$O-phenyl, an —OCH$_2$-pyridinyl;
  the benzyloxy group being optionally substituted by one to three groups selected from a halogen, a trifluoromethyl, a methyl;

on condition that at least one group $R_4$ or $R_5$ represents a group —C(X)$R_6$;

X represents an oxygen atom or a sulfur atom;

$R_6$ represents a $C_{1-6}$ alkoxy group, a hydroxyl or a group —NR$_7$R$_8$; the $C_{1-6}$ alkoxy group being optionally substituted by a phenyl;

$R_7$ and $R_8$ represent independently of one another:
  a hydrogen atom, a $C_{1-6}$ alkyl group optionally substituted by a $C_{3-7}$ cycloalkyl, a $C_{3-7}$ cycloalkenyl, $C_{1-3}$ alkoxy, a phenyl, a morpholinyl or a pyridinyl; or
  a $C_{3-7}$ cycloalkyl, $C_{1-6}$ alkoxy or a phenyl; or
  $R_7$ and $R_8$, taken together with the nitrogen atom to which they are attached, form an aziridine, azetidine, pyrrolidine, piperidine or morpholine ring;
  the $C_{3-7}$ cycloalkyl and phenyl groups being optionally substituted by one or two substituents selected from $C_{1-3}$ alkyl groups, a hydroxyl, a $C_{1-3}$ alkoxy or a halogen atom.

DETAILED DESCRIPTION OF THE INVENTION

Among the compounds of general formula (I) a first group of preferred compounds are those for which:

$R_1$ represents:
  a $C_{1-5}$ alkyl, preferably a methyl, ethyl, 1-methylethyl, 2-methylpropyl, tert-butyl, 1-ethylpropyl, optionally substituted by one to three substituents selected from a fluorine, a hydroxyl, a $C_{1-4}$ thioalkyl, preferably a thiomethyl, a thiophene or a phenyl; or
  a $C_{4-7}$ cycloalkyl, preferably a cyclopropyl or a cyclohexyl, a furanyl, a thiophene, a benzothiophene, a pyridinyl or a phenyl; the phenyl being optionally substituted by one to three substituents selected from a halogen atom, preferably a fluorine or a chlorine, a hydroxyl, a benzyloxy or a methylenedioxy; and/or $R_2$ and $R'_2$ represent independently of one another a hydrogen atom, a halogen atom, preferably a fluorine, a hydroxyl, a $C_{1-3}$ alkyl, preferably a methyl or an ethyl, a $C_{3-7}$ cycloalkyl, preferably a cyclohexyl, a $C_{1-3}$ alkoxy, preferably a methoxy, an O—C(O)—$C_{1-4}$ alkyl group, preferably O—C(O)—CH$_3$, or $R_2$ and $R'_2$ taken together form an oxo group; and/or $R_3$ represents a $C_{1-4}$ alkyl, preferably a methyl, an ethyl, a propyl or a butyl, optionally substituted by a $C_{1-3}$ alkoxy, preferably a methoxy; and/or $R_4$ and $R_5$ represent independently of one another:
  a hydrogen atom, a $C_{1-7}$ alkyl, preferably a methyl, ethyl, 1-methylethyl, n-propyl, butyl, 2-methylpropyl, tert-butyl, 3-methylbutyl, 1-ethylpropyl, 2,2-dimethylpropyl, hexyl, 5-methylhexyl, optionally substituted by a phenyl or a $C_{3-7}$ cycloalkyl, preferably a cyclohexyl; or
  a $C_{3-7}$ cycloalkyl, preferably a cyclopropyl or a cyclohexyl, a phenyl, a naphthyl or a —C(X)$R_6$; the phenyl being optionally substituted by one or two groups selected from a halogen, preferably a bromine, a $C_{1-3}$ alkyl, preferably a methyl or a 1-methylethyl, a hydroxyl, a $C_{1-3}$ alkoxy, preferably a methoxy or ethoxy, a trifluoromethyl, a trifluoromethoxy, a phenyl, a phenoxy, a benzyloxy, a —CH$_2$O-phenyl, an —OCH$_2$-pyridinyl;
  the benzyloxy group being optionally substituted by a group selected from a halogen, preferably a chlorine or a fluorine, a trifluoromethyl or a methyl;

on condition that at least one group $R_4$ or $R_5$ represents a group —C(X)$R_6$; and/or X represents an oxygen atom; and/or $R_6$ represents a $C_{1-6}$ alkoxy group, preferably a methoxy, ethoxy, tert-butyloxy, a hydroxyl or a group —$NR_7R_8$; the $C_{1-6}$ alkoxy group being optionally substituted by a phenyl; and/or $R_7$ and $R_8$ represent independently of one another:
  a hydrogen atom, a $C_{1-3}$ alkyl group, preferably a methyl, ethyl or 1-methylethyl, optionally substituted by a $C_{1-3}$ alkoxy, preferably a methoxy, a $C_{3-7}$ cycloalkenyl, preferably a cyclohexenyl, a phenyl, a morpholinyl or a pyridinyl; a $C_{1-3}$ alkoxy, preferably a methoxy; or
  a $C_{3-6}$ cycloalkyl, preferably a cyclohexyl; or
  $R_7$ and $R_8$, taken together with the nitrogen atom to which they are attached, form an azetidine, piperidine or morpholine ring;
  the phenyl group being optionally substituted by one or two $C_{1-3}$ alkoxy groups, preferably methoxy.

Among the compounds of general formula (I), a second group of preferred compounds are those for which:

$R_1$ represents:
  a $C_{1-6}$ alkyl optionally substituted by one or two substituents selected from a hydroxyl, a $C_{1-6}$ alkoxy, a $C_{1-6}$ thioalkyl, a trifluoromethyl, a thiophene or a phenyl; or
  a $C_{3-7}$ cycloalkyl, a thiophene, a benzothiophene, a pyridinyl, a furanyl or a phenyl;
  the phenyl groups being optionally substituted by one to three substituents selected from a halogen atom, a $C_{1-6}$ alkyl, a $C_{1-6}$ alkoxy, a hydroxyl, a methylenedioxy, a phenoxy or a benzyloxy; and/or $R_2$ and $R'_2$ represent independently of one another a hydrogen atom, a halogen atom, a hydroxyl, a $C_{1-3}$ alkoxy, a $C_{1-3}$ alkyl, a $C_{3-7}$ cycloalkyl, an O—C(O)—$C_{1-6}$ alkyl group, or $R_2$ and $R'_2$ taken together form an oxo group; and/or $R_3$ represents a hydrogen atom or a $C_{1-6}$ alkyl optionally substituted by a hydroxyl or a $C_{1-3}$ alkoxy; and/or $R_4$ and $R_5$ represent independently of one another:
  a hydrogen atom, a $C_{1-7}$ alkyl optionally substituted by a $C_{3-7}$ cycloalkyl or phenyl; or
  a $C_{3-7}$ cycloalkyl, a phenyl, a naphthyl or a —C(X)$R_6$;
  the $C_{3-7}$ cycloalkyl and phenyl groups being optionally substituted by one or more groups selected from a halogen atom, a hydroxyl, a $C_{1-3}$ alkyl, a $C_{1-3}$ alkoxy, a phenyl, a phenoxy, a benzyloxy;

on condition that at least one group $R_4$ or $R_5$ represents a group —C(X)$R_6$; and/or X represents an oxygen atom or a sulfur atom; and/or $R_6$ represents a $C_{1-6}$ alkoxy group, a hydroxyl or a group —$NR_7R_8$; and/or $R_7$ and $R_8$ represent independently of one another:
  a hydrogen atom, a $C_{1-6}$ alkyl group optionally substituted by a $C_{3-7}$ cycloalkyl, a $C_{3-7}$ cycloalkenyl, a phenyl or a pyridinyl; or
  a $C_{3-7}$ cycloalkyl, $C_{1-6}$ alkoxy or a phenyl; or
  $R_7$ and $R_8$, taken together with the nitrogen atom to which they are attached, form an aziridine, azetidine, pyrrolidine, piperidine or morpholine ring;
  the $C_{3-7}$ cycloalkyl and phenyl groups being optionally substituted by a $C_{1-3}$ alkyl group, a hydroxyl, a $C_{1-3}$ alkoxy or a halogen atom.

Among the compounds of general formula (I) a third group of preferred compounds are those for which:

$R_1$ represents:
  a $C_{1-5}$ alkyl, preferably a methyl, ethyl, 1-methylethyl, 2-methylpropyl, tert-butyl, 1-ethylpropyl, optionally substituted by one or two substituents selected from a hydroxyl, a $C_{1-4}$ thioalkyl, preferably a thiomethyl, a trifluoromethyl, a thiophene or a phenyl; or
  a $C_{4-7}$ cycloalkyl, preferably a cyclopropyl or a cyclohexyl; a furanyl, a thiophene, a benzothiophene, a pyridinyl or a phenyl; the phenyl being optionally substituted by one or two substituents selected from a halogen atom, preferably a fluorine or a chlorine, a hydroxyl, a benzyloxy or a methylenedioxy; and/or $R_2$ and $R'_2$ represent independently of one another a hydrogen atom, a halogen atom, preferably a fluorine, a hydroxyl, a $C_{1-3}$ alkyl, preferably a methyl or an ethyl, a $C_{3-7}$ cycloalkyl, preferably a cyclohexyl, a $C_{1-3}$ alkoxy, preferably a methoxy, an O—C(O)—$C_{1-4}$ alkyl group, preferably O—C(O)—$CH_3$, or $R_2$ and $R'_2$ taken together form an oxo group; and/or $R_3$ represents a $C_{1-4}$ alkyl, preferably a methyl, an ethyl, a propyl or a butyl, optionally substituted by a $C_{1-3}$ alkoxy, preferably a methoxy; and/or $R_4$ and $R_5$ represent independently of one another:
  a hydrogen atom, a $C_{1-7}$ alkyl, preferably a methyl, ethyl, 1-methylethyl, n-propyl, butyl, 2-methylpropyl, tert-butyl, 3-methylbutyl, 1-ethylpropyl, 2,2-dimethylpropyl, hexyl, 5-methylhexyl, optionally substituted by a phenyl or a $C_{3-7}$ cycloalkyl, preferably a cyclohexyl; or
  a $C_{3-7}$ cycloalkyl, preferably a cyclopropyl or a cyclohexyl; a phenyl, a naphthyl or a —C(X)$R_6$;
  the phenyl being optionally substituted by one or two groups selected from a $C_{1-3}$ alkyl, preferably a 1-methylethyl, a hydroxyl, a $C_{1-3}$ alkoxy, preferably a methoxy or ethoxy; a phenoxy, a $C_{1-3}$ alkoxy, preferably a methoxy or an ethoxy, a hydroxyl, a phenoxy or a benzyloxy;

on condition that at least one group $R_4$ or $R_5$ represents a group —C(X)$R_6$; and/or X represents an oxygen atom; and/or $R_6$ represents a $C_{1-6}$ alkoxy group, preferably a methoxy, ethoxy, tert-butyloxy, a hydroxyl or a group —$NR_7R_8$; and/or $R_7$ and $R_8$ represent independently of one another:
  a hydrogen atom, a $C_{1-3}$ alkyl group, preferably a methyl, ethyl or 1-methylethyl, optionally substituted by a $C_{3-7}$ cycloalkenyl, preferably a cyclohexenyl, a phenyl or a pyridinyl; or
  a $C_{1-3}$ alkoxy, preferably a methoxy, a $C_{3-6}$ cycloalkyl, preferably a cyclohexyl; or
  $R_7$ and $R_8$, taken together with the nitrogen atom to which they are attached, form an azetidine, piperidine or morpholine ring.

The compounds for which at one and the same time X, $R_1$, $R_2$, $R'_2$, $R_3$, $R_4$, $R_5$, $R_6$, $R_7$ and $R_8$ are as defined above in the groups of preferred compounds are particularly preferred and more specifically, among these, the compounds for which:

$R_1$ represents a $C_{1-4}$ alkyl, preferably a 1-methylethyl or a tert-butyl, or a phenyl substituted by two fluorine atoms; and/or $R_2$ represents a hydroxyl and $R'_2$ represents a hydrogen atom; and/or $R_3$ represents a $C_{1-4}$ alkyl, preferably a methyl, ethyl or propyl; and/or X represents an oxygen atom.

In the context of the present invention:

$C_{t-z}$, where t and z may take the values from 1 to 7, is understood to mean a carbon chain which can have from t to z carbon atoms: for example, $C_{1-3}$, a carbon chain which can have from 1 to 3 carbon atoms; $C_{3-6}$, a carbon chain which can have from 3 to 6 carbon atoms; and so on;

alkyl is understood to mean a linear or branched saturated aliphatic group; for example, a $C_{1-6}$ alkyl group represents a linear or branched carbon chain of from 1 to 6 carbon atoms, more particularly a methyl, ethyl, propyl, 1-methylethyl, butyl, isobutyl, sec-butyl, tert-butyl, and so on, preferably a methyl, ethyl, propyl or 1-methylethyl;

cycloalkyl is understood to mean a cyclic alkyl group; for example, a $C_{3-7}$ cycloalkyl group represents a cyclical carbon chain of from 3 to 7 carbon atoms, more particularly a cyclopropyl, cyclobutyl, cyclopentyl, cyclohexyl, cycloheptyl, preferably a cyclopentyl or cyclohexyl;

cycloalkenyl is understood to mean a mono- or polyunsaturated cyclic alkyl group; for example, a $C_{3-7}$ cycloalkenyl group represents a mono- or polyunsaturated cyclical carbon chain of from 3 to 7 carbon atoms, more particularly a cyclopropenyl, cyclobutenyl, cyclopentenyl, cyclohexenyl, cycloheptenyl, preferably a cyclopentenyl or cyclohexenyl;

thioalkyl is understood to mean an S-alkyl group with a linear or branched, saturated aliphatic chain;

alkoxy is understood to mean an alkyloxy group with a linear or branched, saturated aliphatic chain;

halogen atom is understood to mean a fluorine, a chlorine, a bromine or an iodine; and "$R_2$ and $R'_2$ taken together form an oxo group" is understood to mean the group such that:

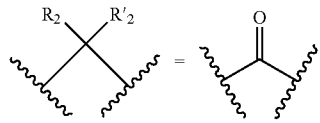

The compounds of general formula (I) may include one or more asymmetric carbons. They may therefore exist in the form of enantiomers or diastereoisomers. These enantiomers and diastereoisomers and their mixtures, including the racemic mixtures, form part of the invention.

When the carbon bearing $R_2$ and $R'_2$ and/or the carbon bearing $R_3$ are asymmetric, preference is given to the compounds of general formula (I) for which the carbon bearing $R_2$ and $R'_2$ is of (S) configuration and/or the carbon bearing $R_3$ is of (S) configuration.

The compounds of formula (I) may exist in the form of bases or of addition salts with acids. Such addition salts form part of the invention.

These salts are advantageously prepared with pharmaceutically acceptable acids, but the salts of other useful acids, for example, for the purification or isolation of the compounds of formula (I), also form part of the invention.

The compounds of general formula (I) may exist in the form of hydrates or solvates, namely in the form of associations or combinations with one or more molecules of water or with a solvent. Such hydrates and solvates likewise form part of the invention.

The present invention secondly provides processes for preparing the compounds of formula (I).

Thus these compounds may be prepared by processes, illustrated in the following schemes, whose operating conditions are conventional for the person skilled in the art.

A protective group is understood to mean a group which makes it possible to block the reactivity of a functional group or position during a chemical reaction which might affect it, and which liberates the molecule after cleavage according to methods known to the person skilled in the art. Examples of protective groups and of methods of protection and deprotection are given, inter alia, in *Protective groups in Organic Synthesis*, Greene et al., 2nd ed. (John Wiley & Sons, Inc., New York).

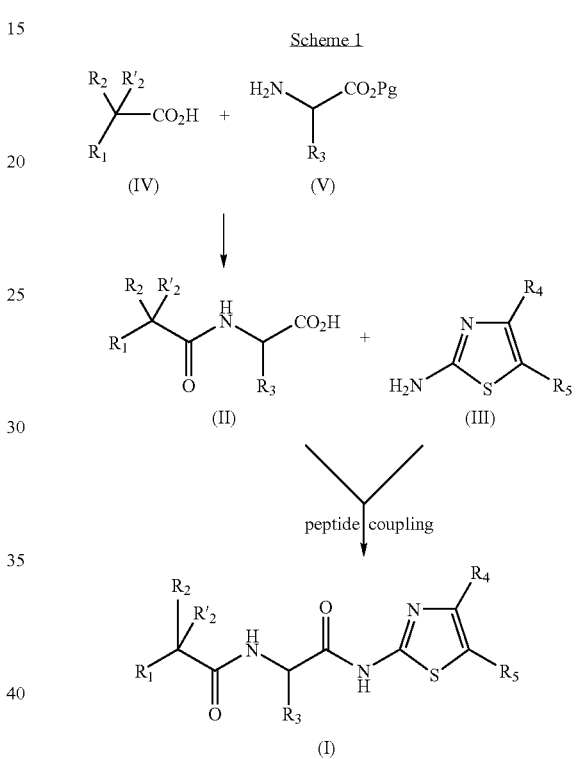

Scheme 1

In accordance with scheme 1 the compound of formula (I) can be obtained by peptide coupling of 2-aminothiazole of formula (III) with the acylamino acid of formula (II) according to conditions known to the person skilled in the art, for example in the presence of benzotriazol-1-yloxytris(pyrrolidino)phosphonium hexafluorophosphate (PyBOP) or benzotriazol-1-yloxytris(dimethylamino)phosphonium hexafluorophosphate (BOP) and of N-ethylmorpholine or N-methylmorpholine in an inert solvent such as dimethylformamide, acetonitrile or dichloromethane at a temperature which can range from 0° C. to the ambient temperature.

The compound of formula (II) may be obtained by peptide coupling of the compound of formula (IV) with the protected acid of formula (V), in which Pg represents a protective group, for example a benzyl, according to methods known to the person skilled in the art, as described above.

The compound thus obtained is subsequently deprotected. In the case where the protection is a benzyl, the compound is hydrogenated beforehand in the presence of palladium on carbon in absolute ethanol at atmospheric pressure of hydrogen, at ambient temperature, to give the compound of formula (II).

Alternatively the compound of formula (I) can be prepared in accordance with scheme 2.

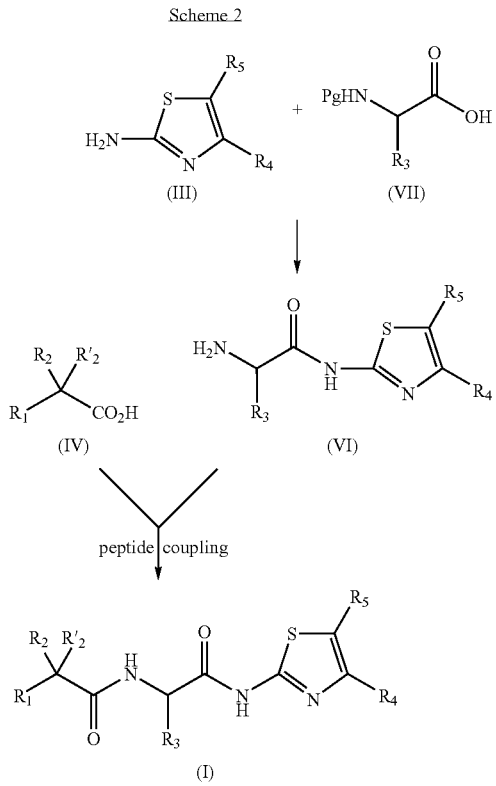

Scheme 2

In accordance with this scheme the compound of formula (I) may be obtained by peptide coupling of the compound of formula (IV) with the amine of formula (VI) according to methods known to the person skilled in the art, such as for example in the presence of hydroxybenzotriazole hydrochloride (HOBt) and 1-ethyl-3-(3-dimethylaminopropyl)carbodiimide (EDAC, HCl).

The compound of formula (VI) can be obtained by peptide coupling of the 2-aminothiazole of formula (III) with the protected amine of formula (VII) according to methods known to the person skilled in the art, as described above. The amine can be protected, for example, by means of an N-tert-butoxycarbonyl (Boc), according to conventional methods known to the person skilled in the art, then deprotected by acidic hydrolysis, in the presence of gaseous hydrochloric acid dissolved in an anhydrous solvent or of trifluoroacetic acid.

The compounds of formula (I) in which $R_2$ and $R'_2$ form an oxo group can be obtained by oxidizing a hydroxyl of the compound of formula (I) in which $R_2$ or $R'_2$ represents a hydroxyl group. The reaction can be performed under conditions known to the person skilled in the art, for example with the Dess-Martin reagent. These compounds can also be obtained by direct coupling of a keto acid of formula (IV) in which $R_2$ and $R'_2$ together form an oxo group with an amine of formula (VI) according to conditions known to the person skilled in the art. The methods of preparing such keto acids are known to the person skilled in the art.

The compound of formula (III) in which $R_4$=—C(O)—$R_6$, $R_6$ representing a $C_{1-6}$ alkoxy group, can be obtained in accordance with scheme 3.

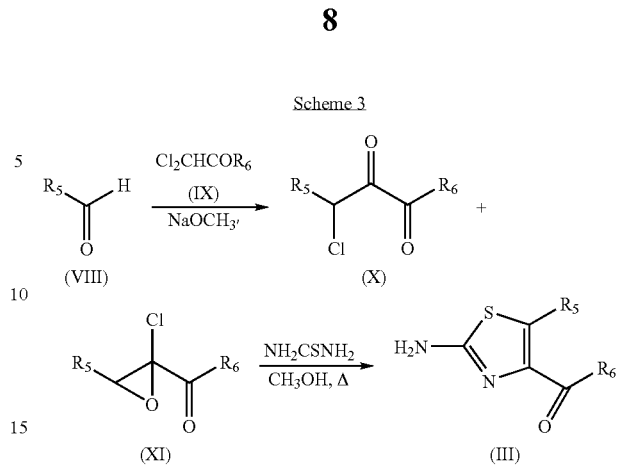

Scheme 3

In accordance with this scheme the compound of formula (III) can be obtained by reacting an aldehyde of formula (VIII) in which $R_5$ is as defined above with the methyldichloroacetate of formula (IX) in which $R_6$ represents a $C_{1-6}$ alkoxy optionally substituted by a phenyl, and, for example, sodium methoxide or ethoxide at 0° C. in an adaptation of the process described by Takeda (Bull. Chem. Soc. JP, 1970, vol. 43, p. 2997). The mixture of products (X) and (XI) obtained is treated with thiourea in the presence, for example, of methanol or ethanol at reflux for 4 or 8 hours to give the compound of formula (III).

The compound of formula (III) in which $R_4$=—C(O)—$R_6$, $R_6$ representing a hydroxyl, can be obtained by hydrolyzing the above compounds for which $R_6$ represents a $C_{1-6}$ alkoxy group optionally substituted by a phenyl, according to conditions known to the person skilled in the art.

The compound of formula (III) in which $R_5$=—C(O)—$R_6$, $R_6$ representing a $C_{1-6}$ alkoxy group, can be obtained in accordance with scheme 4.

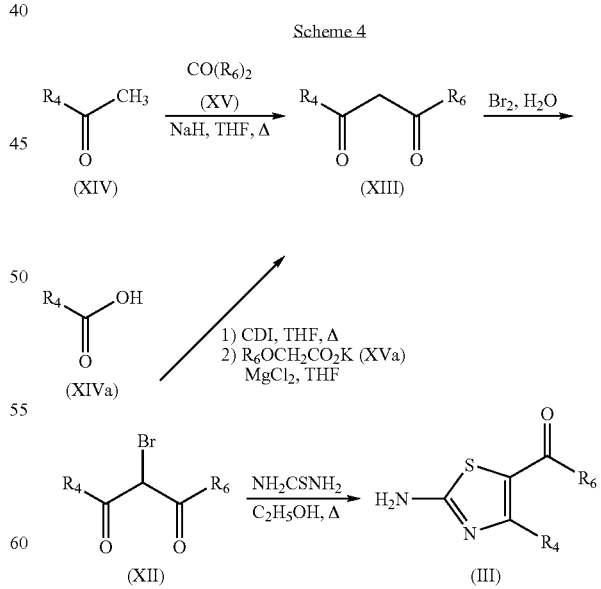

Scheme 4

In accordance with scheme 4 the compound of formula (III) can be obtained by brominating a β-keto ester of formula (XIII) in which $R_6$ represents a $C_{1-6}$ alkoxy optionally substituted by a phenyl, followed by reaction with the thiourea, in an adaptation of the process described by A. Barton, Breukelman, Kaye (J.C.S. Perkin I, 1982, p. 159), to give the compound of formula (XII).

The β-keto ester of formula (XIII) can be obtained by reacting a ketone of formula (XIV) in which $R_4$ is as defined above with a dialkyl carbonate of formula (XV) in which $R_6$ represents a $C_{1-6}$ alkoxy optionally substituted by a phenyl, in an adaptation of the process described by L. Crombie, R. C. F. Jones and C. J. Palmer (J.C.S. Perkin Trans. I, 1987, p. 323). The β-keto ester of formula (XIII) can also be obtained by reacting an acid of formula (XIVa) activated with carbonyldiimidazole (CDI) with a malonate of formula (XVa) in which $R_6$ represents a $C_{1-6}$ alkoxy optionally substituted by a phenyl, in an adaptation of the process described, for example, by D. W. Brooks, L. D.-L. Lu and S. Masamune (Angew. Chem. Int. Ed. Engl., 18, 1979, p. 72).

Where $R_4$ represents a hydrogen atom the preparation of the compound of formula (XIII) is accomplished in an adaptation of the process described, for example, by Tetrahedron Letters, 42, 2001, p. 2101. The compound of formula (III) in which $R_5$=—C(O)—$R_6$, $R_6$ representing a hydroxyl, can be obtained by hydrolyzing the above compounds for which $R_6$ represents a $C_{1-6}$ alkoxy group, according to conditions known to the person skilled in the art.

The compound of formula (III) in which $R_4$ or $R_5$ represents a group —C(O)—$NR_7R_8$ can be obtained in accordance with scheme 5.

Scheme 5

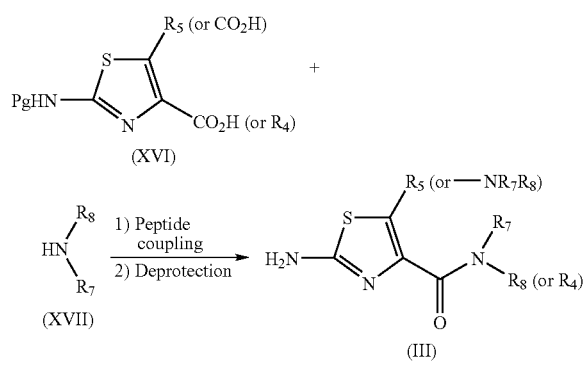

In accordance with this scheme the compound of formula (III) is obtained by peptide coupling of the compound of formula (XVI) in which $R_5$ or $R_4$ represents a carboxyl group and Pg a protective group such as a Boc with a compound of formula (XVII) in which $R_7$ and $R_8$ are as defined above in the presence, for example, of HOBt and (EDAC, HCl). The compound thus obtained is then deprotected according to conditions known to the person skilled in the art. The compound of formula (XVI) in which Pg represents a Boc can be obtained by protecting a compound of formula (III) in which $R_4$ or $R_5$ represents a group —C(O)$R_6$ and $R_6$ is a $C_{1-6}$ alkoxy optionally substituted by a phenyl by the action of di-tert-butyl dicarbonate in anhydrous tetrahydrofuran in the presence of dimethylaminopyridine at ambient temperature, followed by hydrolysis of the carboxylate according to conditions known by the person skilled in the art, for example with lithium hydroxide in a 7:3 (v/v) tetrahydrofuran/water mixture at a temperature of 60° C.

The starting compounds, particularly the compounds of formula (IV), (V), (VII), (VIII), (IX), (XIV), (XIVa), (XV), (XVa) and (XVII), are available commercially or are described in the literature, or can be prepared by methods described therein or known to the person skilled in the art. The compounds of formula (IV) in which $R_2$ or $R'_2$ represents a hydroxyl may be prepared by adding trimethylsilyl cyanide to an aldehyde in an adaptation of the process described by D. A. Evans et al. (J.C.S., Chem. Comm. 1973, p. 55) or by reacting sodium nitrite with an alpha-amino acid in an adaptation of the process described by I. Shinn et al., (J. Org. Chem., 200, 65, p. 7667).

When a functional group of a compound is reactive, for example when $R_1$ contains a hydroxyl, it may necessitate prior protection before reaction. The person skilled in the art will be able to determine easily the need for prior protection.

The meanings of $R_1$, $R_2$, $R'_2$, $R_3$, $R_4$, $R_5$, X, $R_6$, $R_7$ and $R_8$ in the compounds of formula (II) to (XVII) are as defined for the compounds of formula (I).

The compounds of formula (II), (III) and (VI) are novel and likewise form part of the invention. They are useful as synthetic intermediates for the preparation of compounds of general formula (I).

The following examples describe the preparation of certain compounds in accordance with the invention. These examples are not limitative and merely illustrate the invention.

The numbers of the compounds exemplified refer to those given in the subsequent table. The elemental microanalyses and the NMR, IR or mass spectra confirm the structures of the compounds obtained.

EXAMPLE 1

Methyl 2-amino-5-(1-methylethyl)thiazole-4-carboxylate 14.4 g of isobutyraldehyde in solution in 400 ml of diethyl ester is admixed at 0° C. with 24.6 g of methyl dichloroacetate then dropwise with 400 ml of a solution of sodium methoxide (0.5M) in methanol. After 1 h at 0° C., 100 ml of saturated aqueous sodium chloride solution are added and the mixture is extracted with ether. The organic phase is dried over anhydrous sodium sulfate. The ether alone is evaporated, retaining the methanol, 8 g of thiourea are added and the mixture is heated at reflux for 6 h. The reaction medium is evaporated to dryness and the residue is taken up in ethyl acetate and washed with 10% aqueous ammonium hydroxide solution then with saturated aqueous sodium chloride solution. The organic phase is dried over anhydrous sodium sulfate and then concentrated. The residue is taken up in 100 ml of ether and filtered on a frit to yield 18.6 g of the title compound as a white solid.

NMR 300 MHz (CDCl$_3$) δ ppm: 1.25 (d, 6H); 3.35 (s, 3H); 4.10 (m, 1H); 5.50 (s, 2H).

EXAMPLE 2

Ethyl 2-amino-4-(2,2-dimethylpropyl)thiazole-5-carboxylate 4 g of 4,4-dimethylpentanone in solution in 100 ml of anhydrous tetrahydrofuran are admixed with 3 g of 60% sodium hydride followed by 8.2 g of diethyl carbonate, dropwise. The reaction medium is heated at reflux for 5 h.

It is cooled and hydrolyzed with 50 ml of distilled water.

The tetrahydrofuran is evaporated. The residue is extracted with ethyl acetate. The organic phase is dried over sodium sulfate and then evaporated. This gives 4.9 g of a colored oil.

NMR 300 MHz δ in ppm (CDCl$_3$): 1.05 (s, 9H); 1.28 (t, 3H); 2.42 (s, 2H); 3.40 (s, 2H); 4.18 (q, 4H).

A suspension of 4.9 g of the β-keto ester obtained above in 75 ml of distilled water at 0° C. is admixed dropwise with 1.4 ml of bromine. The reaction medium is stirred at 0° C. for 1 h then extracted with ethyl acetate. The organic phase is washed with saturated sodium chloride solution then dried over sodium sulfate.

Evaporation gives 4.1 g of an orange-colored oil.

NMR 300 MHz (CDCl$_3$) δ ppm: 1.00 (s, 9H); 1.30 (t, 3H); 2.60 (ms, 2H); 4.25 (q, 2H); 4.75 (s, 1H).

A solution of 4.10 g of bromo-β-keto ester in 60 ml of ethanol is admixed with 1.1 g of thiourea. The reaction medium is heated at reflux for 6 h, then evaporated to dryness. The residue is taken up in ethyl acetate and washed with 10% aqueous ammonium hydroxide solution then with saturated aqueous sodium chloride solution and dried over sodium sulfate. Following evaporation, the residue is recrystallized from an ethyl acetate/pentane mixture. This gives 2.1 g of a white solid.

NMR 300 MHz (CDCl$_3$) δ ppm: 0.97 (s, 9H); 1.21 (t, 3H); 2.92 (s, 2H); 4.25 (q, 2H); 5.65 (s, 2H).

EXAMPLE 3

Methyl 2-[2-[2-(3,5-difluorophenyl)acetyl-amino] propanoylamino]-5-propylthiazole-4-carboxylate (Compound 2)

EXAMPLE 3.1

N-3,5-Difluorophenylacetyl-(S)-alanine

A solution of 1.72 g of 3,5-difluorophenyl-acetic acid in 50 ml of dimethylformamide at 0° C. is admixed with 1.01 g of N-methylmorpholine, 5.72 g of PyBOP, 2.15 g of (S)-alanine benzyl ester hydrochloride and 1.01 g of N-methylmorpholine. The mixture is allowed to return to ambient temperature and is stirred for 18 h. The reaction medium is evaporated and the residue is taken up in ethyl acetate and washed twice with saturated aqueous sodium bicarbonate solution, a solution of potassium hydrogen sulfate (1M) and then with saturated aqueous sodium chloride solution. The organic phase is dried over anhydrous sodium sulfate. The residue is chromatographed on a silica gel column, eluting with a 7:3 (v/v) petroleum ether/ethyl acetate mixture, to give 1.9 g of a white solid.

NMR 300 MHz (CDCl$_3$) δ ppm: 1.40 (d, 3H); 3.54 (s, 2H); 4.62 (m, 1H); 5.18 (m, 2H); 6.10 (d, 1H); 6.73 (t, 2H); 6.80 (d, 1H); 7.32 (m, 5H).

A solution of 1.9 g of N-3,5-difluorophenylacetyl-(S)-alanine benzyl ester in 80 ml of absolute ethanol is admixed with 300 mg of 10% palladium on carbon. The reaction medium is hydrogenated at atmospheric pressure and at ambient temperature for 8 h. The reaction medium is filtered on paper, washed with absolute ethanol and then evaporated. This gives 1.37 g of a white solid.

NMR 300 MHz (CDCl$_3$) δ ppm: 1.36 (d, 3H); 3.48 (s, 2H); 3.70 (s, 1H); 4.40 (m, 1H); 6.65 (t, 2H); 6.70 (d, 1H); 6.95 (d, 1H).

EXAMPLE 3.2

Methyl 2-[2-[2-(3,5-difluorophenyl)-acetylamino] propanoylamino]-5-propylthiazole-4-carboxylate A solution of 0.24 g of methyl 2-amino-5-propylthiazole-4-carboxylate, prepared by the process described in Example 1, in 25 ml of dimethylformamide at 0° C. is admixed with 0.12 g of N-methylmorpholine, 0.69 g of PyBOP and then 0.275 g of the compound obtained in step 3.1 of Example 3. The reaction is allowed to return to ambient temperature and the mixture is stirred for 18 h.

The solvent is evaporated, and the residue is taken up in ethyl acetate and washed twice with saturated aqueous sodium bicarbonate solution, once with water, once with a 1N aqueous solution of potassium hydrogen sulfate and then with saturated aqueous sodium chloride solution. The organic phase is dried over anhydrous sodium sulfate and concentrated. The residue is chromatographed on a silica column, eluting with a 1:1 (v/v) petroleum ether/ethyl acetate mixture, to give 0.22 g of a white powder.

LC/MS: MH$^+$=426.

NMR 500 MHz (CDCl$_3$) δ ppm: 0.91 (q, 3H); 1.30 (d, 3H); 1.61 (m, 2H); 3.06 (t, 2H); 3.53 (s, 2H); 3.77 (s, 3H); 4.38 (m, 1H); 6.98 (m, 2H); 7.08 (m, 1H); 8.57 (d, 1H); 12.49 (s, 1H).

EXAMPLE 4

Methyl 2-[2-[2-(3,5-difluorophenyl)acetyl-amino] propanoylamino]-4-propylthiazole-5-carboxylate (Compound 144)

A solution of 0.3 g of methyl 2-amino-4-propylthiazole-5-carboxylate prepared by the process described in Example 2, in 30 ml of dimethylformamide at 0° C. is admixed with 0.101 g of N-methylmorpholine, 0.86 g of PyBOP and 0.34 g of N-3,5-difluoro-phenylacetyl-(S)—alanine, obtained in step 3.1 of Example 3. The reaction medium is allowed to return to ambient temperature and then is stirred for 18 h. After the solvent has been evaporated the residue is taken up in ethyl acetate and washed twice with saturated aqueous sodium bicarbonate solution, twice with water, once with a 1M aqueous solution of potassium hydrogen sulfate and then with saturated aqueous sodium chloride solution. The organic phase is dried over anhydrous sodium sulfate and then concentrated. The residue is chromatographed on a silica column, eluting with a 3:7 (v/v) ethyl acetate/petroleum ether mixture, to give 0.45 g of a white powder.

LC/MS: MH$^+$=426.

NMR 500 MHz (DMSO) δ ppm: 0.88 (t, 3H); 1.32 (d, 3H); 1.66 (m, 2H); 2.95 (m, 2H); 3.54 (s, 2H); 3.76 (s, 3H); 4.47 (m, 2H); 6.97 and 7.10 (2m, 3H); 8.63 (d, 1H); 12.66 (s, 1H).

EXAMPLE 5

Methyl 2-[2-[2-(3,5-difluorophenyl)acetylamino]-(2S)-pentanoylamino]-5-(1-methylethyl)thiazole-4-carboxylate (Compound 18)

EXAMPLE 5.1

Methyl 2-(2-amino-(2S)-pentanoylamino)-5-(1-methylethyl)thiazole-4-carboxylate

A solution of 2.3 g of methyl 2-amino-5-(1-methylethyl)thiazole-4-carboxylate, obtained in Example 1, in 100 ml of dimethylformamide at 0° C. is admixed with 1.22 g of N-methylmorpholine, 6.34 g of PyBOP and then 2.65 g of (S)-Boc-norvaline. The reaction medium is allowed to return to ambient temperature and then is stirred for 16 h.

Following evaporation, the residue is taken up in ethyl acetate and washed twice with saturated aqueous sodium bicarbonate solution, twice with water, once with a 1H aqueous solution of potassium hydrogen sulfate and then with saturated aqueous sodium chloride solution. The organic phase is dried over anhydrous sodium sulfate and then concentrated. The residue is chromatographed on a silica gel column, eluting with a 3:7 (v/v) ethyl acetate/petroleum ether mixture. This gives 3.5 g of a white solid.

NMR 300 MHz (CDCl$_3$) δ ppm: 0.97 (t, 3H); 1.37 (d, 6H); 1.45 (s, 9H); 1.67 (m, 2H); 1.90 (m, 2H); 3.90 (s, 3H); 4.10 (m, 1H); 4.38 (unresolved complex, 1H); 4.90 (unresolved complex, 1H).

A solution of 3.3 g of the product obtained above in 60 ml of trifluoroacetic acid is stirred at ambient temperature for 30 min, followed by evaporation. The residue is taken up in ethyl acetate and washed twice with saturated aqueous sodium carbonate solution and then with saturated aqueous sodium chloride solution. The organic phase is dried over anhydrous sodium sulfate and then evaporated to give 2 g of a white solid.

NMR 300 MHz (CDCl$_3$) δ ppm: 0.97 (t, 3H); 1.35 (d, 6H); 1.40 to 1.60 (m, 2H); 1.80 (m, 2H); 3.60 (m, 1H); 3.97 (s, 3H); 4.12 (m, 1H).

EXAMPLE 5.2

Methyl 2-[2-[2-(3,5-difluorophenyl)acetyl-amino]-(2S)-pentanoylamino]-5-(1-methylethyl)thiazole-4-carboxylate A solution of 0.7 g of methyl 2-(2-amino-(2S)-pentanoylamino)-5-(1-methylethyl)thiazole-4-carboxylate, obtained in step 5.1 of Example 5, in 30 ml of dimethylformamide at 0° C. is admixed with 0.255 g of N-methylmorpholine, 1.30 g of PyBOP and then 0.43 g of 3,5-difluorophenylacetic acid. The reaction is allowed to return to ambient temperature and the mixture is stirred for 18 h. The reaction medium is evaporated. The residue is taken up in ethyl acetate and washed twice with saturated aqueous sodium bicarbonate solution, twice with water, once with a 1M aqueous solution of potassium hydrogen sulfate and then with saturated aqueous sodium chloride solution. The organic phase is dried over anhydrous sodium sulfate and then concentrated. The residue is chromatographed on a silica column, eluting with a 1:1 (v/v) petroleum ether/ethyl acetate mixture, to give 0.7 g of a white solid.

LC/MS: MH$^+$=454.

NMR 500 MHz (DMSO) δ ppm: 0.85 (t, 3H); 1.26 (d, 6H); 1.28-1.65 (m, 4H); 3.53 (m, 2H); 3.78 (s, 3H); 3.97 (m, 1H); 4.36 (m, 1H); 6.96 (d, 2H); 7.08 (m, 1H); 8.49 (d, 1H); 12.52 (s, 1H).

EXAMPLE 6

Methyl 2-[2-[2-(3,5-difluorophenyl)acetylamino]-(2S)-pentanoylamino]-4-(1-methylethyl)thiazole-5-carboxylate (Compound 146)

The procedure of Example 5 is repeated, replacing the methyl 2-amino-5-(1-methylethyl)thiazole-4-carboxylate with methyl 2-amino-4-(1-methylethyl)thiazole-5-carboxylate, prepared by the process described in Example 2.

LC/MS: MH$^+$=454.

NMR 500 MHz (DMSO) δ ppm: 0.87 (t, 3H); 1.27 (d, 6H); 1.35 (m, 2H); 1.64 (m, 2H); 3.54 (s, 2H); 3.77 (s, 3H); 3.90 (m, 1H); 4.45 (m, 1H); 6.96-7.09 (m, 3H); 8.53 (d, 1H); 12.69 (s, 1H).

EXAMPLE 7

Methyl 2-[2-[2-(3,5-difluorophenyl)-2-hydroxyacetylamino]-(2S)-pentanoylamino]-5-(1-methylethyl)thiazole-4-carboxylate (Compounds 19 and 20)

A solution of 1 g of methyl 2-(2-amino-(2S)-pentanoylamino)-5-(1-methylethyl)thiazole-4-carboxylate, obtained in step 5.1 of Example 5, in 80 ml of dimethylformamide at 0° C. is admixed with 0.366 g of N-methylmorpholine, 1.87 g of PyBOP and then 0.677 g of 3,5-difluoromandelic acid. The reaction medium is allowed to return to ambient temperature, stirred for 16 h and then concentrated. The residue is taken up in ethyl acetate and washed twice with saturated aqueous sodium bicarbonate solution, twice with water, once with a 1M aqueous solution of potassium hydrogen sulfate and then with saturated aqueous sodium chloride solution. The organic phase is dried over anhydrous sodium sulfate and then concentrated.

The residue is chromatographed on a silica gel column, eluting with a mixture of petroleum ether and ethyl acetate ranging from 7:3 (1:1) (v/v). The two isomers (S,S) and (R,S) can be separated in this way. This gives 0.45 g of a white powder ((S,S) isomer) and 0.50 g (mixture of the two diastereoisomers). The mixture of the two diastereoisomers (0.50 g) is rechromatographed on a silica gel column, eluting with a 7:3 (v/v) to (1:1) petroleum ether/ethyl acetate mixture, to give 0.25 g of a white powder ((R,S) isomer).

(S,S) isomer:
LC/MS: MH$^+$=470.
NMR 500 MHz (DMSO) δ ppm: 0.80 (t, 3H); 1.18 (m, 2H); 1.22 (d, 6H); 1.68 (m, 2H); 3.78 (s, 3H); 3.97 (m, 1H); 4.43 (m, 1H); 5.05 (d, 1H); 6.55 (d, 1H); 7.13 (m, 3H); 8.24 (d, 1H); 12.46 (s, 1H).
$\alpha_D^{20}$=−53° (c=1/MeOH)
(R,S) isomer:
LC/MS: MH$^+$=470.
NMR 500 MHz (DMSO) δ ppm: 0.82 (t, 3H); 1.26 (d, 6H); 1.26 (m, 2H); 1.68 (m, 2H); 3.78 (s, 3H); 3.97 (m, 1H); 4.40 (m, 1H); 5.07 (d, 1H); 6.42 (d, 1H); 7.12 (m, 3H); 8.27 (d, 1H); 12.51 (s, 1H).
$\alpha_D^{20}$=−83° (c=1/MeOH)

EXAMPLE 8

Methyl 2-[2-[2-(3,5-difluorophenyl)-2-hydroxyacetylamino]-(2S)-pentanoylamino]-4-(1-methylethyl)thiazole-5-carboxylate (Compounds 150 and 151)

The procedure of Example 7 is repeated, replacing the methyl 2-(2-(S)-pentanoylamino)-5-(1-methylethyl)thiazole-4-carboxylate with methyl 2-(2-(S)—pentanoylamino)-4-(1-methylethyl)thiazole-5-carboxylate obtained by the process described in step 5.1 of Example 5.

(S,S) isomer:
LC/MS: MH$^+$=471.
NMR 500 MHz (DMSO) δ ppm: 0.81 (t, 3H); 1.18 (d, 6H); 1.22 (m, 2H); 1.71 (m, 2H); 3.77 (s, 3H); 3.90 (m, 1H); 4.50 (m, 1H); 5.06 (s, 1H); 6.54 (s, 1H); 7.12 (m, 3H); 8.30 (d, 1H); 12.66 (s, 1H).
$\alpha_D^{20}$=−73° (c=1/MeOH)

(R,S) isomer:
LC/MS: MH+=471 (95% purity)
NMR 500 MHz (DMSO) δ ppm: 0.83 (t, 3H); 1.19 (d, 6H); 1.22 (m, 2H); 1.70 (m, 2H); 3.77 (s, 3H); 3.91 (m, 1H); 4.48 (m, 1H); 5.07 (s, 1H); 6.42 (s, 1H); 7.12 (m, 3H); 8.34 (d, 1H); 12.67 (s, 1H).
$\alpha_D^{20}$=−104° (c=1/MeOH)

EXAMPLE 9

2-[2-[2-(3,5-Difluorophenyl)acetylamino]-(2S)-pentanoylamino]-5-(1-methylethyl)thiazole-4-N,N-dimethylcarboxamide (Compound 26)

EXAMPLE 9.1

2-tert-Butoxycarbonylamino-5-(1-methylethyl)thiazole-4-carboxylic acid

A solution of 4.4 g of methyl 2-amino-5-(1-methylethyl)thiazole-4-carboxylate, obtained in Example 1, in 150 ml of tetrahydrofuran is admixed with 5.27 g of di-tert-butyl dicarbonate and 0.13 g of dimethylaminopyridine. The mixture is stirred at ambient temperature for 16 h. The reaction medium is evaporated. The residue is taken up in ethyl acetate and washed twice with a 0.5N aqueous solution of hydrochloric acid, once with water, then with saturated aqueous sodium chloride solution. The organic phase is dried over anhydrous sodium sulfate and concentrated. This gives 6.1 g of the protected aminothiazole derivative in the form of a solid which is used as it is without purification.
NMR 300 MHz (CDCl$_3$) δ ppm: 1.25 (d, 6H); 1.50 (s, 9H); 3.85 (s, 3H); 3.97 (m, 1H).
LC/MS: MH+=301 (M-Boc)+=201

A solution of 6.10 g of the product obtained above in 150 ml of tetrahydrofuran is admixed at ambient temperature with a solution of 1.68 g of lithium hydroxide in 80 ml of distilled water. The tetrahydrofuran reaction mixture is heated at reflux for 16 h and then concentrated. The residue is taken up in water and washed twice with ethyl acetate. The aqueous phase is acidified with a 1N solution of hydrochloric acid to approximately pH~4, saturated with sodium chloride and extracted twice with ethyl acetate. The organic phase is dried over anhydrous sodium sulfate and then concentrated. This gives 5.10 g of a white solid.
LC/MS: MH+=287.
NMR 300 MHz (CDCl$_3$) δ ppm: 1.19 (d, 6H); 1.45 (s, 9H); 3.80 (s, 3H); 3.90 (unresolved complex s, 1H); 4.15 (m, 1H).

EXAMPLE 9.2

2-tert-Butoxycarbonylamino-5-(1-methylethyl)thiazole-4-N,N-dimethylcarboxamide

A solution of 2 g of 2-tert-butoxycarbonyl-amino-5-(1-methylethyl)thiazole-4-carboxylic acid, obtained in step 9.1, in 80 ml of dimethylformamide is admixed with 1.07 g of hydroxybenzotriazole hydrate, 1.33 g of (EDAC, HCl) then 0.57 g of N,N-dimethylamine hydrochloride and 0.77 g of N-methylmorpholine. The reaction medium is stirred at ambient temperature for 16 h and then concentrated. The residue is taken up in ethyl acetate and washed twice with saturated aqueous sodium bicarbonate solution, twice with a 1M aqueous solution of potassium hydrogen sulfate, once with water and then with saturated aqueous chloride solution. The organic phase is dried over anhydrous sulfate and concentrated. This gives 1.45 g of a white solid.

LC/MS: MH+=314
NMR 300 MHz (CDCl$_3$) δ ppm: 1.30 (d, 6H); 1.53 (s, 9H); 2.98 (s, 3H); 3.09 (s, 3H); 3.40 (m, 1H); 8.00 (s, 1H).

EXAMPLE 9.3

2-Amino-5-(1-methylethyl)thiazole-4-N,N-dimethylcarboxamide 1.4 g of 2-tert-butoxycarbonylamino-5-(1-methylethyl)thiazole-4-N,N-dimethylcarboxamide, obtained in step 9.2, are admixed with 30 ml of trifluoroacetic acid. The mixture is stirred at ambient temperature for 30 min and then concentrated. The residue is taken up in ethyl acetate and washed twice with saturated aqueous sodium carbonate solution then with saturated aqueous sodium chloride solution. The organic phase is dried over anhydrous sodium sulfate and then concentrated. This gives 0.90 g of a white solid.
LC/MS: MH+=214
NMR 300 MHz (CDCl$_3$) δ ppm: 1.22 (d, 6H); 3.00 (s, 3H); 3.30 (m, 1H); 4.90 (s, 1H).

EXAMPLE 9.4

2-((2S)-Pentanoylamino)-5-(1-methylethyl)-thiazole-4-N,N-dimethylcarboxamide 0.9 g of 2-amino-5-(1-methylethyl)thiazole-4-N,N-dimethylcarboxamide, obtained in step 9.3, is coupled with 1 g of (S)-Boc-norvaline by the process described in step 5.1 of Example 5. Chromatography on silica, eluted with a 1:1 (v/v) mixture of ethyl acetate and petroleum ether, gives 1.1 g of a viscous oil which crystallizes at ambient temperature.
LC/MS: MH+=413
NMR 300 MHz (CDCl$_3$) δ ppm: 0.97 (t, 3H); 1.30 (d, 6H); 1.40 (s, 9H); 1.65 (m, 2H); 1.90 (m, 2H); 2.95 (s, 3H); 3.08 (s, 3H); 3.48 (m, 1H); 4.30 (m, 1H); 5.25 (unresolved complex, 1H). 1.1 g of the compound obtained above are deprotected in 20 ml of trifluoroacetic acid by the process described in step 9.3. This gives 0.77 g of a white solid.
LC/MS: MH+=313
NMR 300 MHz (CDCl$_3$) δ ppm: 0.98 (t, 3H); 1.60 (d, 6H); 1.30-1.95 (unresolved complex 4H); 2.98 (s, 3H); 3.08 (s, 3H); 3.40 (m, 1H); 3.58 (m, 1H).

EXAMPLE 9.5

2-[2-[2-(3,5-Difluorophenyl)acetylamino]-(2S)-pentanoylamino]-5-(1-methylethyl)thiazole-4-N,N-dimethylcarboxamide A solution of 0.23 g of 2-((2S)-pentanoyl-amino)-5-(1-methylethyl)thiazole-4-N,N-dimethyl-carboxamide, obtained in step 9.4, in 15 ml of dimethylformamide at 0° C. is admixed with 0.088 g of N-methylmorpholine and then 0.416 g of PyBOP and 0.138 g of 3,5-difluorophenylacetic acid. The reaction medium is allowed to return to ambient temperature for 16 h and then is concentrated. The residue is taken up in ethyl acetate and washed twice with a 0.5N aqueous solution of hydrochloric acid, once with water and then with saturated aqueous sodium chloride solution. The organic phase is dried over anhydrous sodium sulfate and concentrated. Chromatography on a silica column, eluted with a 1:1 (v/v) mixture of ethyl acetate and petroleum ether, gives 0.26 g of a white solid.
LC/MS: MH+=467.

NMR 500 MHz (DMSO) δ ppm: 0.87 (t, 3H); 1.24 (d, 6H); 1.29-1.67 (m, 4H); 2.86 (s, 3H); 2.95 (s, 3H); 3.22 (m, 1H); 3.54 (m, 2H); 4.41 (m, 1H); 6.98 (d, 2H); 7.08 (m, 1H); 8.49 (d, 1H); 12.21 (s, 1H).

$\alpha_D^{20}$=−74° (c=1.0, MeOH)

EXAMPLE 10

2-[2-[2-(3,5-Difluorophenyl)-2-hydroxy-(2S)-acetylamino]-(2S)-pentanoylamino]-5-(1-methylethyl) thiazole-4-N,N-dimethylcarboxamide (Compound 88) and 2-[2-[2-(3,5-difluorophenyl)-2-hydroxy-(2R)-acetylamino]-(2S)-pentanoylamino]-5-(1-methylethyl)thiazole-4-N,N-dimethylcarboxamide (Compound 89)

By the process described above in step 9.5 of Example 9, 0.77 g of 2-((2S)-pentanoylamino)-5-(1-methylethyl)thiazole-4-N,N-dimethylcarboxamide, obtained in step 9.4 of Example 9, is coupled with 0.51 g of 3,5-difluoromandelic acid in the presence of 0.28 g of N-methylmorpholine and 1.4 g of PyBOP at 0° C. and chromatography on a silica column, eluted with a 75:25 (v/v) mixture of ethyl acetate and petroleum ether, gives 0.80 g of a white solid.

LC/MS: MH$^+$=483 (2 peaks: 2 diastereoisomers (R,S) and (S,S)).

NMR 500 MHz (DMSO) δ ppm: 0.72 (t, 3H); 1.06 (m, 1H); 1.16 (m, 1H); 1.27 (d, 6H); 1.58 (m, 2H); 2.10 (s, 3H); 3.78 (s, 3H); 3.96 (m, 1H); 4.37 (m, 1H); 5.97 (s, 1H); 7.34 and 7.47 (2m, 5H); 8.62 (s, 1H); 12.49 (s, 1H).

$\alpha_D^{20}$=−67° (c=1.0, /MeOH)

The two diastereoisomers can be separated by preparative HPLC on a C$_{18}$ column with an acetonitrile/H$_2$O gradient from 95:5 (v/v) to 5:95 in 23 min.

This gives 0.1 g ((S,S) isomer) of a white solid,

LC/MS: MH$^+$=483.

NMR 500 MHz (DMSO) δ ppm: 0.80 (t, 3H); 1.25 (d, 6H); 1.28 (m, 2H); 1.75 (m, 2H); 2.80 (s, 3H); 3.00 (s, 3H); 3.25 (m, 1H); 4.49 (m, 1H); 5.08 (s, 1H); 6.55 (broad s, 1H); 7.13 (d, 3H); 8.25 (d, 1H); 12.15 (s, 1H).

and 0.17 g ((R,S) isomer) of a white solid.

LC/MS: MH$^+$=483.

NMR 500 MHz (DMSO) δ ppm: 0.88 (t, 3H); 1.22 (d, 6H); 1.30 (m, 2H); 1.68 (m, 2H); 2.87 (s, 3H); 2.98 (s, 3H); 3.25 (m, 1H); 4.45 (m, 1H); 5.10 (s, 1H); 6.42 (s, 1H); 7.18 (m, 5H); 8.30 (d, 1H); 12.20 (s, 1H).

EXAMPLE 11

Methyl 2-[2-[2-hydroxy-2-phenyl-(2S)-acetylamino]-(2S)-pentanoylamino]-5-(1-methylethyl)-thiazole-4-carboxylate (Compound 30) and methyl 2-[2-[2-hydroxy-2-phenyl-(2R)-acetylamino]-(2S)-pentanoylamino]-5-(1-methylethyl)thiazole-4-carboxylate (Compound 31)

0.35 g of methyl 2-(2-amino-(2S)-pentanoylamino)-5-(1-methylethyl)thiazole-4-carboxylate, obtained in step 5.1 of Example 5, in solution in 20 ml of dimethylformamide at 0° C. is admixed with 0.13 g of N-methylmorpholine, 0.67 g of PyBOP then 0.20 g of (S)-mandelic acid or (R)-mandelic acid. The reaction medium is allowed to return to ambient temperature and then is stirred for 16 h and concentrated.

The residue is taken up in ethyl acetate and washed by the process described in Example 7. Following evaporation of the organic phase, the residue is chromatographed on a silica column, eluting with a 1:1 (v/v) ethyl acetate/petroleum ether mixture. This gives 0.36 g of the (S,S) diastereoisomer and 0.37 g of the (R,S) diastereoisomer, in the form of a white powder.

(S,S) isomer:

LC/MS: MH$^+$=434.

NMR 500 MHz (DMSO) δ ppm: 0.80 (t, 3H); 1.16 (m, 2H); 1.26 (s, 9H); 1.68 (m, 2H); 3.78 (s, 3H); 3.97 (m, 1H); 4.43 (m, 1H); 4.98 (d, 1H); 6.31 (d, 1H); 7.32 (m, 5H); 8.14 (d, 1H); 12.46 (s, 1H).

$\alpha_D^{20}$=−51° (c=1.0, /MeOH).

(R,S) isomer:

LC/MS: MH$^+$=434.

NMR 500 MHz (DMSO) δ ppm: 0.85 (t, 3H); 1.28 (s, 6H); 1.28 (m, 2H); 1.68 (m, 2H); 3.78 (s, 3H); 3.97 (m, 1H); 4.44 (m, 1H); 5.00 (d, 1H); 6.17 (d, 1H); 7.30 (m, 5H); 8.17 (d, 1H); 12.51 (s, 1H).

$\alpha_D^{20}$=−110° (c=1.0, /MeOH).

EXAMPLE 12

Methyl 2-[2-[2-(3,5-difluorophenyl)-2-oxoacetylamino]-(2S)-pentanoylamino]-5-(1-methylethyl)-thiazole-4-carboxylate (Compound 75)

A solution of 0.3 g of methyl 2-[2-[2-(3,5-difluorophenyl)-2-hydroxyacetylamino]-(2S)-pentanoylamino]-5-(1-methylethyl)thiazole-4-carboxylate, obtained in Example 7, in 40 ml of absolute dichloromethane stabilized with amylene is admixed with 0.55 g of Dess-Martin periodinane reagent and 0.09 g of tert-butanol. The reaction mixture is stirred at ambient temperature for 20 h and then evaporated. The residue is chromatographed (without prior treatment) on a silica column, eluting with an 8:2 (v/v) petroleum ether/ethyl acetate mixture. This gives 0.20 g of a white powder.

LC/MS: MH$^+$=468 (purity 100%)

NMR 500 MHz (DMSO) δ ppm: 0.97 (t, 3H); 1.20 (d, 6H); 1.40 (m, 2H); 1.80 (m, 2H); 3.87 (s, 3H); 4.05 (m, 1H); 4.60 (m, 1H); 7.60 (m, 2H); 7.80 (m, 1H); 7.99 (m, 2H); 9.30 (d, 1H); 12.70 (s, 1H).

EXAMPLE 13

Methyl 2-[2-[-2-[-(3,5)-difluorophenyl-2-hydroxy-(2S)-acetylamino]-(2S)-pentanoylamino]-4-methylthiazole-5-carboxylate (Compound 165)

The title compound is obtained by the processes described in Examples 7 and 8 as set forth below.

A solution of 0.90 g of methyl 2-(2-amino-(2S)-pentanoylamino)-4-(methyl)thiazole-5-carboxylate, obtained by the process described in Example 5.1, in 75 ml of dimethylformamide at 0° C. is admixed with 0.366 g of N-methylmorpholine, 1.87 g of PyBOP then 0.677 g of 3,5-difluoromandelic acid. The reaction medium is allowed to return to ambient temperature and is stirred for 16 h and then concentrated. The residue is taken up in ethyl acetate and washed twice with saturated aqueous sodium bicarbonate solution, twice with water, once with (1M) aqueous potassium hydrogen sulfate solution and then with saturated aqueous sodium chloride solution. The organic phase is dried over anhydrous sodium sulfate and then concentrated. The residue is chromatographed on a column of silica gel, eluting with a mixture of petroleum ether and ethyl acetate ranging from 8:2 to 7:3 (v/v). This gives 0.1 g of a white powder (S,S isomer) and 0.7 g (mixture of the 2 diastereoisomers).

(S,S) isomer:
LC/MS: MH+=442
NMR 500 MHz (DMSO) δ ppm: 0.82 (t, 3H); 1.26 (m, 2H); 1.69 (m, 2H); 2.63 (s, 3H); 3.77 (s, 3H); 4.50 (m, 1H); 5.07 (d, 1H); 6.55 (d, 1H); 7.16 (m, 3H); 8.31 (d, 1H); 12.65 (s, 1H).

EXAMPLE 14

Methyl 2-[2-[2-(3,5)-difluorophenyl)-2-oxoacetylamino]-(2S)-pentanoylamino]-4-methylthiazole-5-carboxylate (Compound 167)

A solution of 0.7 g of methyl 2-[2-[2-(3,5)-difluorophenyl-2-hydroxy-(2S)-acetylamino-(2S)-pentanoylamino]-4-methylthiazole-5-carboxylate, obtained in Example 13, in 80 ml of absolute dichloromethane stabilized with amylene is admixed with 1.35 g of Dess-Martin periodinane reagent and 0.24 g of tert-butanol. The reaction mixture is stirred at ambient temperature for 20 h and then evaporated. The residue is chromatographed (without prior treatment) on a silica column, eluting with an 8:2 (v/v) petroleum ether/ethyl acetate mixture. This gives 0.68 g of a white powder.
LC/MS: MH+=440
$\alpha_D^{20}$=−87° (c=1, MeOH).
NMR 500 MHz (DMSO) δ ppm: 0.90 (t, 3H); 1.38 (m, 2H); 1.75 (m, 2H); 2.63 (s, 3H); 3.78 (s, 3H); 4.61 (m, 1H); 7.69 (m, 3H); 9.43 (d, 1H).

EXAMPLE 15

Methyl 2-[2-[2-hydroxy-3,3-dimethyl-(2S)-butyrylamino]-(2S)-pentanoylamino]-5-(1-methylethyl)-thiazole-4-carboxylate (Compound 97)

A solution of 0.24 g of methyl 2-(2-amino-(2S)-pentanoylamino)-5-(1-methylethyl)thiazole-4-carboxylate, obtained in step 5.1 of Example 5, in 10 ml of dimethylformamide at 0° C. is admixed with 97 μl of N-methylmorpholine, 0.116 g of (S)-(−)-2-hydroxy-3,3-dimethylbutyric acid and then 0.46 g of PyBOP. The reaction medium is stirred for 18 hours after return to ambient temperature and then is concentrated under reduced pressure. The residue is taken up in 50 ml of ethyl acetate and washed successively with 50 ml of a saturated solution of $KHSO_4$ in $H_2O$, 50 ml of a saturated solution of $K_2CO_3$ in $H_2O$, 50 ml of saturated NaCl solution and then 50 ml of $H_2O$. After drying and evaporation of the organic phase, the residue is chromatographed on a silica (40 g) column, eluted with a gradient from 100% of petroleum ether to a 30/70 mixture of petroleum ether/ethyl acetate (v/v). This gives 0.269 g of white crystals.
LC/MS: MH+=414.
NMR 500 MHz (DMSO) δ ppm: 0.90 (t, 3H); 0.93 (s, 9H); 1.30 (d, 6H); 1.32 (m, 2H); 1.71 (m, 2H); 3.58 (d, 1H); 3.82 (s, 3H); 4.02 (m, 1H); 4.52 (m, 1H); 5.60 (d, 1H); 7.82 (d, 1H); 12.45 (s, 1H).
$\alpha_D^{20}$=−74° (c=1.0, /MeOH).

EXAMPLE 16

Methyl 2-[2-(2-fluoro-2-phenyl-(2S)-acetylamino-(2S)-pentanoylamino]-5(1-methylethyl)thiazole-4-carboxylate (Compound 98) and methyl 2-[2-(2-fluoro-2-phenyl-(2R)-acetylamino-(2S)-pentanoylamino]-5(1-methylethyl)thiazole-4-carboxylate (Compound 99)

A solution of 0.60 g of methyl 2-(2-amino-(2S)-pentanoylamino)-5-(1-methylethyl)thiazole-4-carboxylate, obtained in step 5.1 of Example 5, in 15 ml of dimethylformamide at 0° C. is admixed with 242 μl of N-methylmorpholine, 0.34 g of α-fluorophenylacetic acid and then 1.144 g of PyBOP. The reaction medium is stirred for 18 hours following return to ambient temperature and then is concentrated under reduced pressure. The residue is taken up in 50 ml of ethyl acetate and washed successively with 50 ml of a saturated solution of $KHSO_4$ in $H_2O$, 50 ml of a saturated solution of $K_2CO_3$ in $H_2O$, 50 ml of saturated NaCl solution and then 50 ml of $H_2O$. After drying and evaporation of the organic phase, the residue is chromatographed on a silica (40 g) column, eluted with a gradient from 100% petroleum ether to a 30/70 mixture of petroleum ether/ethyl acetate (v/v). This gives 123 mg of (S,S) isomer and 177 g of (R,S) isomer.

(S,S) isomer:
LC/MS: MH+=436.
NMR 500 MHz (DMSO) δ ppm: 0.87 (t, 3H); 1.22 (d, 6H); 1.32 (m, 2H); 1.70 (m, 2H); 3.78 (s, 3H); 3.98 (m, 1H); 4.52 (m, 1H); 5.90 and 6.00 (2s, 1H); 7.44 (m, 5H); 8.70 (d, 1H); 12.55 (s, 1H).
$\alpha_D^{20}$=−55° (c=1.0, /MeOH).

(R,S) isomer:
LC/MS: MH+=436.
NMR 500 MHz (DMSO) δ ppm: 0.90 (t, 3H); 1.24 (m, 2H); 1.30 (s, 6H); 1.77 (m, 2H); 3.85 (s, 3H); 4.05 (m, 1H); 4.48 (m, 1H); 5.97 and 6.05 (2s, 1H); 7.50 (m, 5H); 8.80 (d, 1H); 12.62 (s, 1H).
$\alpha_D^{20}$=−71.3° (c=1.0, MeOH).

EXAMPLE 17

Methyl 2-[2-[2-(3-chloro)-2-hydroxy-(2S)-acetylamino]-(2S)-pentanoylamino]-5-(1-methylethyl)-thiazole-4-carboxylate (Compound 107)

EXAMPLE 17.1

2-(3-Chlorophenyl)-2-hydroxy-(2S)-acetic acid

A solution of 2.85 ml of 3-chlorobenzaldehyde in 20 ml of dichloromethane is admixed cautiously with 3.66 ml of trimethylsilyl cyanide and then with a catalytic amount of zinc iodide ($ZnI_2$). The reaction medium is stirred for 3 hours at ambient temperature and then at 60° C. for 2 hours. The reaction medium is cooled to 0° C. and 9 ml of concentrated HCl are added. The reaction medium is stirred for 18 hours at ambient temperature and then 1 hour at reflux. After cooling, the reaction mixture is poured into water and extracted twice with 50 ml of AcOEt. The combined organic phases are extracted with 100 ml of 7.5N NaOH at 4° C. After separation, the aqueous phase is washed with 3×50 ml of AcOEt. The aqueous phase is acidified with 70 ml of 12N HCl and extracted with 3×50 ml of AcOEt. The combined organic phases are dried and the solvent is evaporated.

(R)-3-Chloromandelic acid is separated by crystallization in the form of (R)-(+)-phenylethylamine salt. (S)-3-Chloromandelic acid is obtained from the mother liquor by crystallization in the form of (S)-(−)-phenethylamine salt. This gives 78 mg of white crystals.

The acid obtained is used without further purification in the following step.

EXAMPLE 17.2

Methyl 2-[2-[2-(3-chloro)-2-hydroxy-(2S)-acetylamino]-(2S)-pentanoylamino]-5-(1-methylethyl)-thiazole-4-carboxylate A solution of 0.072 g of methyl 2-(2-amino-(2S)-pentanoylamino)-5-(1-methylethyl)thiazole-4-carboxylate, obtained in step 5.1 of Example 5, in 5 ml of dimethylformamide at 0° C. is admixed with 29-µl of N-methylmorpholine, 0.081 g of (S)-3-chloromandelic acid and then 0.137 g of PyBOP. The reaction medium is stirred for 40 hours after return to ambient temperature and then is concentrated under reduced pressure. The residue is taken up in 50 ml of ethyl acetate and washed successively with 50 ml of a saturated solution of $KHSO_4$ in $H_2O$, 50 ml of a saturated solution of $K_3CO_3$ in $H_2O$, 50 ml of saturated NaCl solution and then 50 ml of $H_2O$. After drying and evaporation of the organic phase, the residue is chromatographed on a silica (40 g) column, eluted with a gradient from 100% of petroleum ether to 100% of ethyl acetate. This gives 0.059 g of white crystals.

LC/MS: $MH^+=468$.

NMR 500 MHz (DMSO) δ ppm: 0.87 (t, 3H); 1.20 (m, 2H); 1.22 (d, 6H); 1.70 (m, 2H); 3.80 (s, 3H); 4.00 (m, 1H); 4.43 (m, 1H); 5.02 (s, 1H); 6.44 (s, 1H); 7.30 (m, 3H); 7.45 (s, 1H); 8.20 (d, 1H); 12.45 (s, 1H).

EXAMPLE 18

Methyl 2-[2-(3-ethyl-2-hydroxy-(2S)-pentanoylamino)-(2S)-pentanoylamino]-5-(1-methylethyl)thiazole-4-carboxylate (Compound 108) and methyl 2-[2-(3-ethyl-2-hydroxy-(2R)-pentanoylamino)-(2S)-pentanoylamino]-5-(1-methylethyl)thiazole-4-carboxylate (Compound 109)

EXAMPLE 18.1

3-Ethyl-2-hydroxypentanoic acid

A solution of 1.24 ml of 2-ethylbutyraldehyde in 18 ml of anhydrous dichloromethane is admixed cautiously with 1.5 ml of trimethylsilyl cyanide and then with a catalytic amount of $ZnI_2$. The reaction medium is stirred for 2 hours at ambient temperature and then at 60° C. for 3.5 hours. The reaction medium is cooled to 0° C. and 3.5 ml of concentrated HCl are added. The reaction medium is stirred for 18 hours at ambient temperature and then for 1 hour at reflux. After cooling, the reaction mixture is poured into water and extracted twice with 50 ml of AcOEt. The combined organic phases are extracted with 100 ml of 7.5N NaOH at 4° C. After separation, the aqueous phase is washed with 3×50 ml of AcOEt. The aqueous phase is acidified with 70 ml of 12N HCl and extracted with 3×50 ml of AcOEt. The combined organic phases are dried and the solvent is evaporated.

The acid obtained is used without further purification in the following step.

EXAMPLE 18.2

Methyl 2-[2-(3-ethyl-2-hydroxy-(2S)-pentanoylamino)-(2S)-pentanoylamino]-5-(1-methylethyl)thiazole-4-carboxylate and methyl 2-[2-(3-ethyl-2-hydroxy-(2R)-pentanoylamino)-(2S)-pentanoylamino]-5-(1-methylethyl)thiazole-4-carboxylate A solution of 0.457 g of methyl 2-(2-amino-(2S)-pentanoylamino)-5-(1-methylethyl)thiazole-4-carboxylate obtained in step 5.1 of Example 5, in 15 ml of dimethylformamide at 0° C. is admixed with 181 µl of N-methylmorpholine, 0.45 g of 3-ethyl-2-(S)-hydroxypentanoic acid and then 0.858 g of PyBOP. The reaction medium is stirred for 18 hours after return to ambient temperature and then is concentrated under reduced pressure. The residue is taken up in 50 ml of ethyl acetate and washed successively with 50 ml of a saturated solution of $KHSO_4$ in $H_2O$, 50 ml of a saturated solution of $K_2CO_3$ in $H_2O$, 50 ml of saturated NaCl solution and then 50 ml of $H_2O$. After drying and evaporation of the organic phase, the residue is chromatographed on a silica (40 g) column, eluted with a gradient from 100% of petroleum ether to a 20/80 mixture of petroleum ether/ethyl acetate (v/v). This gives 78 mg of (S,S) isomer and 131 mg of (R,S) isomer.

(S,S) isomer:

LC/MS: $MH^+=428$.

NMR 500 MHz (DMSO) δ ppm: 0.86 (t, 3H); 0.93 (m, 6H); 1.24 (m, 2H); 1.32 (d, 6H); 1.38 (m, 4H); 1.55 (m, 1H); 1.72 (m, 2H); 3.78 (s, 3H); 3.98 (m, 1H); 4.05 (m, 1H); 4.55 (m, 1H); 5.55 (d, 1H); 7.92 (d, 1H); 12.50 (s, 1H).

$\alpha_D^{20}=53.9°$ (c=1.0, /MeOH).

(R,S) isomer:

LC/MS: $MH^+=436$.

NMR 500 MHz (DMSO) δ ppm: 0.80 (t, 3H); 0.90 (m, 6H); 1.20 (m, 2H); 1.30 (d, 6H); 1.34 (m, 4H); 1.55 (m, 1H); 1.74 (m, 2H); 3.86 (s, 3H); 4.00 (m, 2H); 4.53 (m, 1H); 5.42 (d, 1H); 8.00 (d, 1H); 12.54 (s, 1H).

$\alpha_D^{20}=26.9°$ (c=1.0, /MeOH).

EXAMPLE 19

Methyl 2-[2-[3-(3,5-difluorophenyl)-2-hydroxy-(2S)-propionylamino]-(2S)-pentanoylamino]-5-(1-methylethyl)thiazole-4-carboxylate (Compound 110)

EXAMPLE 19.1

3-(3,5-Difluorophenyl)-2-hydroxy-(2S)-propionic acid

A suspension of 1.6 g of (S)-3,5-difluoro-phenylalanine in 5.3 ml of $H_2SO_4$ (2.5N) is admixed dropwise at 0° C. with a solution of 0.829 g of sodium nitrite in 4.2 ml of $H_2O$. The reaction mixture is stirred for 2 hours at 0° C. and then for 17 hours at ambient temperature. The reaction mixture is extracted with 2×100 ml of AcOEt. The combined organic phases are washed with 100 ml of saturated NaCl solution in $H_2O$. Drying gives 1.197 g of yellow crystals. The acid obtained is used without further purification in the following step.

EXAMPLE 19.2

Methyl 2-[2-[3-(3,5-difluorophenyl)-2-hydroxy-(2S)-propionylamino]-(2S)-pentanoylamino]-5-(1-methylethyl)thiazole-4-carboxylate A solution of 0.897 g of methyl 2-(2-amino-(2S)-pentanoylamino)-5-(1-methylethyl)thiazole-4-carboxylate, obtained in step 5.1 of Example 5, in 10 ml of dimethylformamide at 0° C. is admixed with 363 µl of N-methylmorpholine, 0.666 g of 3-(3,5-difluorophenyl)-2-hydroxypropionic acid and then 1.72 g of PyBOP. The reaction medium is stirred for 17 hours after return to ambient temperature and then is concentrated under reduced pressure. The residue is taken up in 50 ml of ethyl acetate and washed successively with 50 ml of a saturated solution of $KHSO_4$ in $H_2O$, 50 ml of a saturated solution of $K_2CO_3$ in $H_2O$, 50 ml of a saturated solution of NaCl and then 50 ml of $H_2O$. After drying and evaporation of the organic phase, the residue is chromatographed on a silica (90 g) column, eluted with a gradient from 100% of petroleum ether to a 10/90 mixture of petroleum ether/ethyl acetate (v/v). This gives 0.43 g of white crystals.

LC/MS: $MH^+$=484.

NMR 500 MHz (DMSO) δ ppm: 0.82 (m, 3H); 1.10 (m, 2H); 1.27 (m, 6H); 1.61 (m, 2H); 2.83 and 2.95 (2m, 1H); 3.77 (s, 3H); 3.96 (m, 1H); 4.21 (m, 1H); 4.43 (m, 1H); 5.68 and 5.81 (2d, 1H); 6.93-7.01 (m, 3H); 7.84 and 7.97 (2d, 1H); 12.46 (s, 1H).

$\alpha_D^{20}$=−32.8° (c=1.0, /MeOH).

EXAMPLE 20

Methyl 2-[2-[2-(2-benzyloxyphenyl)-2-hydroxy-acetylamino]-(2S)-pentanoylamino]-5-(1-methylethyl)thiazole-4-carboxylate (Compound 122)

EXAMPLE 20.1

(2-Benzyloxyphenyl)hydroxyacetic acid

A solution of 1.24 ml of 2-benzyloxy-benzaldehyde in 10 ml of anhydrous dichloromethane is admixed cautiously with 4.4 ml of trimethylsilyl cyanide and then with a catalytic amount of $ZnI_2$. The reaction medium is stirred for 2.5 hours at ambient temperature and then at 60° C. for 4 hours. The reaction medium is cooled to 0° C. and 10.5 ml of concentrated HCl are added. The reaction medium is stirred for 18 hours at ambient temperature and then for 1 hour at reflux. After cooling, the reaction mixture is poured into water and extracted twice with 50 ml of AcOEt. The combined organic phases are extracted with 100 ml of 7.5N NaOH at 4° C. After separation, the aqueous phase is washed with 3×50 ml of AcOEt. The aqueous phase is acidified with 70 ml of 12N HCl and extracted with 3×50 ml of AcOEt. The combined organic phases are dried and the solvent is evaporated. The acid obtained is used without further purification in the following step.

EXAMPLE 20.2

Methyl 2-[2-[2-(2-benzyloxyphenyl)-2-hydroxy-acetylamino]-(2S)-pentanoylamino]-5-(1-methylethyl)thiazole-4-carboxylate A solution of 1.88 g of methyl 2-(2-amino-(2S)-pentanoylamino)-5-(1-methylethyl)thiazole-4-carboxylate, obtained in step 5.1 of Example 5, in 50 ml of dimethylformamide at 0° C. is admixed with 760 μl of N-methylmorpholine, 13 g of (2-benzyloxyphenyl)hydroxy-acetic acid and then 3.6 g of PyBOP. The reaction mixture is stirred for 17 hours after return to ambient temperature and then is concentrated under reduced pressure. The residue is taken up in 100 ml of ethyl acetate and washed successively with 100 ml of a saturated solution of $KHSO_4$ in $H_2O$, 100 ml of a saturated solution of $K_2CO_3$ in $H_2O$, 100 ml of saturated NaCl solution and then 100 ml of $H_2O$. After drying and evaporation of the organic phase, the residue is chromatographed on a silica (90 g) column, eluted with a gradient from 100% petroleum ether to a 30/70 mixture of petroleum ether/ethyl acetate (v/v). This gives 0.43 g of a white foam.

LC/MS: $MH^+$=540.

$\alpha_D^{20}$=87.0° (c=1.0, /MeOH).

NMR 500 MHz (DMSO) δ ppm: 0.85 (m, 3H); 1.26 (m, 2H); 1.28 (d, 6H); 1.69 (m, 2H); 3.78 (s, 3H); 3.98 (m, 1H); 4.47 (m, 1H); 5.22 (s, 2H); 5.33 (2d, 1H); 6.07 and 6.11 (2d, 1H); 6.90-7.50 (m, 8H) 8.00 (m, 1H); 12.48 (s, 1H).

EXAMPLE 21

Methyl 2-[2-[2-hydroxy-2-(2-hydroxyphenyl)-acetylamino]-(2S)-pentanoylamino]-5-(1-methylethyl)-thiazole-4-carboxylate (Compound 128)

A solution of 1.187 g of methyl 2-[2-[2-(2-benzyloxyphenyl)-2-hydroxyacetylamino]-(2S)-pentanoylamino]-5-(1-methylethyl)thiazole-4-carboxylate, obtained in Example 20, in 10 ml of ethanol under a nitrogen atmosphere is admixed with 144 mg of Pd/C (10%). The reaction mixture is stirred for 24 h under an $H_2$ atmosphere. The catalyst is removed by filtration and the solvent is evaporated under reduced pressure. The residue is chromatographed on a silica (90 g) column, eluted with a gradient from 100% of petroleum ether to a 40/60 mixture of petroleum ether/ethyl acetate (v/v). This gives 0.68 g of white crystals.

LC/MS: $MH^+$=450.

$\alpha_D^{20}$=−89.5° (c=1.0, /MeOH).

NMR 500 MHz (DMSO) δ ppm: 0.91 (m, 3H); 1.28 (m, 2H); 1.30 (d, 6H); 1.80 (m, 2H); 3.85 (s, 3H); 4.07 (m, 1H); 4.53 (m, 1H); 5.31 and 5.35 (2s, 1H); 6.87 (m, 2H); 7.13 (m, 1H); 7.27 (m, 1H); 8.17 (m, 1H); 9.66 (broad s, 1H); 12.49 (s, 1H).

EXAMPLE 22

Methyl 2-[2-[2-(3,5-difluorophenyl)-2-hydroxy-(2S)-acetylamino]-(2S)-(3-methoxypropionyl)amino]-5-(1-methylethyl)thiazole-4-carboxylate (Compound 60) and methyl 2-[2-[2-(3,5-difluorophenyl)-2-hydroxy-(2R)-acetylamino]-(2S)-(3-methoxypropionyl)amino]-5-(1-methylethyl)thiazole-4-carboxylate (Compound 61)

EXAMPLE 22.1

Methyl 2-[(2S)-2-amino-3-methoxypropionylamino]-5-(1-methylethyl)thiazole-4-carboxylate A solution of 2.00 g of methyl 2-amino-5-(1-methylethyl)thiazole-4-carboxylate, obtained in Example 1, in 100 ml of dimethylformamide at 0° C. is admixed with 1.01 g of N-methylmorpholine, 5.72 g of PyBOP and then 2.40 g of (S)—BOC—O-methylserine, dicyclohexylamine. The reaction is allowed to return to ambient temperature and the mixture is stirred for 18 h.

The solvent is evaporated and the residue is taken up in ethyl acetate and washed twice with saturated aqueous sodium bicarbonate solution, once with water and once with a 1N aqueous solution of potassium hydrogen sulfate and then with saturated aqueous sodium chloride solution.

The organic phase is dried over anhydrous sodium sulfate and concentrated. The residue is chromatographed on a silica column, eluting with an 8:2 (v/v) petroleum ether/ethyl acetate mixture, to give 2.70 g of a white powder.

LC/MS: $MH^+$=402.

NMR 300 MHz ($CDCl_3$): 1.33 (d, 6H); 1.48 (s, 9H); 3.32 (s, 3H); 3.33 and 3.99 (2m, 2H); 3.55 (m, 1H); 3.92 (s, 3H); 4.13 (m, 1H); 4.5 (broad s 1H); 5.40 (d, 1H).

A solution of 4.30 g of the product obtained in the manner described above, in 60 ml of trifluoroacetic acid, is stirred at ambient temperature for 30 min, and then the solution is evaporated.

The residue is taken up in ethyl acetate and washed twice with saturated aqueous sodium carbonate solution and then with saturated aqueous sodium chloride solution. The organic phase is dried over anhydrous sodium sulfate and then evaporated to give 0.50 g of a white solid, which is used without purification in the following step.

EXAMPLE 22.2

Methyl 2-[2-[2-(3,5-difluorophenyl)-2-hydroxy-(2S)-acetylamino]-(2S)-(3-methoxypropionyl)amino]-5-(1-methylethyl)thiazole-4-carboxylate and methyl 2-[2-[2-(3,5-difluorophenyl)-2-hydroxy-(2R)-acetylamino]-(2S)-(3-methoxypropionyl)amino]-5-(1-methylethyl)thiazole-4-carboxylate A solution of 0.29 g of methyl 2-[(2S)-2-amino-3-methoxypropionylamino]-5-(1-methylethyl)thiazole-4-carboxylate, obtained in step 22.2, in 80 ml of dimethylformamide at 0° C. is admixed with 0.106 g of N-methylmorpholine, 0.55 g of PyBOP and then 0.20 g of 3,5-difluoromandelic acid. The reaction medium is allowed to return to ambient temperature and is stirred for 16 h and then concentrated. The residue is taken up in ethyl acetate and washed twice with saturated aqueous sodium bicarbonate solution, twice with water, once with a 1M aqueous solution of potassium hydrogen sulfate and then with saturated aqueous sodium chloride solution. The organic phase is dried over anhydrous sodium sulfate and then concentrated. The residue is chromatographed on a column of silica gel, eluting with a (1:1) (v/v) petroleum ether/ethyl acetate mixture. The two isomers (S,S) and (R,S) can be separated in this way. This gives 0.10 g of a white powder [(S,S) isomer] and 0.50 g [(R,S) isomer].

(S,S) isomer:
LC/MS: MH$^+$=472.
NMR 500 MHz (DMSO) δ ppm: 1.25 (d, 6H); 3.23 (s, 2H); 3.59 (m, 1H); 3.61 (m, 1H); 3.78 (s, 3H); 3.96 (m, 1H); 4.64 (m, 1H); 5.09 (s, 1H); 6.62 (s, 1H); 7.13 (m, 3H); 8.23 (d, 1H); 12.53 (s, 1H).

(R,S) isomer:
LC/MS: MH$^+$=472.
NMR 500 MHz (DMSO) δ ppm: 1.26 (t, 3H); 3.23 (s, 2H); 3.62 (m, 1H); 3.71 (m, 1H); 3.78 (s, 3H); 3.97 (m, 1H); 4.00 (m, 1H); 5.10 (s, 1H); 6.56 (s, 1H); 7.13 (m, 3H); 8.26 (d, 1H); 12.59 (s, 1H).

EXAMPLE 23

Methyl 2-[2-[2-(3,5-difluorophenyl)acetyl-amino]-(2S)-(3-methoxypropionyl)amino]-5-(1-methylethyl)thiazole-4-carboxylate (Compound 59)

A solution of 0.21 g of methyl 2-[2-[2-(3,5-difluorophenyl)-2-hydroxyacetylamino]-(2S)-(3-methoxypropionyl)amino]-5-(1-methylethyl)thiazole-4-carboxylate, obtained in Example 22, in 30 ml of dimethylformamide at 0° C. is admixed with 0.09 g of N-methylmorpholine, 0.42 g of PyBOP and then 0.14 g of 3,5-difluorophenylacetic acid.

The reaction is allowed to return to ambient temperature and the mixture is stirred for 18 h. The reaction medium is evaporated. The residue is taken up in ethyl acetate and washed twice with saturated aqueous sodium bicarbonate solution, twice with water, once with 1M aqueous solution of potassium hydrogen sulfate and then with saturated aqueous sodium chloride solution. The organic phase is dried over anhydrous sodium sulfate and then concentrated. The residue is chromatographed on a silica column, eluting with a 1:1 (v/v) petroleum ether/ethyl acetate mixture to give 0.12 g of a white solid.
LC/MS: MH$^+$=456.
NMR 500 MHz (DMSO) δ ppm: 1.26 (t, 3H); 3.28 (d, 3H); 3.55 (s, 2H); 3.57 (m, 2H); 3.78 (s, 3H); 3.97 (m, 1H); 4.64 (m, 1H); 6.98 (d, 2H); 7.08 (m, 1H); 8.57 (d, 1H); 12.54 (s, 1H).

EXAMPLE 24

Methyl 2-[2-[2-(3,5-difluorophenyl)acetylamino]-(2S)-butyrylamino]-5-(1-methylethyl)thiazole-4-carboxylate (Compound 51)

EXAMPLE 24.1

Methyl 2-[(2S)-2-aminobutyrylamino]-5-(1-methylethyl)thiazole-4-carboxylate 2.03 g of 2-(2S)-(tert-butoxycarbonyl)amino-butyric acid in 50 ml of N,N-dimethylformamide are coupled with 1.92 g of methyl 2-amino-5-(1-methylethyl)thiazole-4-carboxylate, obtained in Example 1, with 5.72 g of PyBOP and 1.07 g of N-methylmorpholine to give, after chromatography, 2.50 g of a white powder. Deprotection of the BOC group in TFA gives, after basic washing, 1.60 g of a white solid, which is used without purification in the following step:
LC/MS: MH$^+$=286.

EXAMPLE 24.2

Methyl 2-[2-[2-(3,5-difluorophenyl)acetylamino]-(2S)-butyrylamino]-5-(1-methylethyl)thiazole-4-carboxylate Methyl 2-[(2S)-2-aminobutyrylamino]-5-(1-methylethyl)thiazole-4-carboxylate (1.6 g), obtained in step 24.1, in N,N-dimethylformamide is coupled by the process described in Example 5.2 with 0.38 g of 3,5-difluorophenylacetic acid, 1.14 g of PyBOP and 0.22 g of N-methylmorpholine to give, after chromatography, 0.66 g of a white powder.
LC/MS: MH$^+$=440.
NMR 500 MHz (DMSO) δ ppm: 0.79 (t, 3H); 1.26 (d, 6H); 1.73 (m, 2H); 3.78 (s, 3H); 3.96 (m, 1H); 4.36 (m, 1H); 5.06 (s, 1H); 6.56 (s, 1H); 7.13 (m, 3H); 8.22 (d, 1H); 12.46 (s, 1H).
$\alpha_D^{20}$=−73° (c=1.0, /MeOH).

EXAMPLE 25

2-[2-[2-(3,5-Difluorophenyl)acetylamino]-(2S)-pentanoylamino]-4-methylthiazole-5-N-methyl-N-phenylethylcarboxamide (Compound 176)

The title compound is obtained using the process described in Example 9 as further set forth below.

EXAMPLE 25.1

2-Amino-4-methylthiazole-5-N-methyl-N-phenylethylcarboxamide

A solution of 5.58 g of methyl 2-amino-4-methylthiazole-5-carboxylate, obtained by the process described in Example 2, in tetrahydrofuran is reacted with 7.19 g of di-tert-butyl dicarbonate and 0.18 g of dimethylaminopyridine to give 6.90 g of a white powder, which is used as it is without purification.

LC/MS: MH$^+$=187.

NMR 300 MHz (CDCl$_3$): 1.45 (s, 9H); 2.48 (s, 3H); 9.80 (broad s, 1H).

2-Amino-4-methylthiazole-5-N-methyl-N-phenylethylcarboxamide, protected on the amine by a BOC, is obtained by coupling the process described in Example 9.2. This is done by employing a solution of 1.50 g of ethyl 2-tert-butoxycarbonylamino-4-methylthiazole-5-carboxylate in 100 ml of N,N-dimethylformamide with 0.88 g of hydroxybenzotriazole hydrate, 0.95 g of EDAC, HCl and 0.78 g of N-methyl-N-phenethylamine. Chromatography gives 1.10 g of a white powder.

LC/MS: MH$^+$=376.

(M-BOC)$^+$=276.

The BOC protective group is deprotected by the process described in Example 9.3. This gives 0.90 g of 2-amino-4-methylthiazole-5-N-methyl-N-phenylethylcarboxamide in the form of a white powder.

LC/MS: MH$^+$=276.

EXAMPLE 25.2

2-(2-Amino-(2S)-pentanoylamino)-4-methylthiazole-5-N-methyl-N-phenylethylcarboxamide 0.90 g of 2-amino-4-methylthiazole-5-N-methyl-N-phenylethylcarboxamide, obtained in step 25.1, is coupled with 0.78 g of (S)—BOC-norvaline by the process described in step 5.1 of Example 5. Chromatography on silica, eluted with a 1:1 (v/v) ethyl acetate/petroleum ether mixture, gives 1.05 g of a white foam.

LC/MS: MH$^+$=475.

1.05 g of the compound obtained above are deprotected in 25 ml of trifluoroacetic acid by the process described in step 9.3. This gives 0.80 g of a white solid.

LC/MS: MH$^+$=375.

EXAMPLE 25.3

2-[2-[2-(3,5-Difluorophenyl)acetylamino]-(2S)-pentanoylamino]-4-methylthiazole-5-N-methyl-N-phenylethylcarboxamide The same process is followed as in Example 5.2.

0.80 g of 2-(2-amino-(2S)-pentanoylamino)-4-methylthiazole-5-N-methyl-N-phenylethylcarboxamide in 50 ml of N,N-dimethylformamide is coupled with 1.19 g of PyBOP, 0.23 g of N-methylmorpholine and 0.40 g of 3,5-difluorophenylacetic acid to give, after purification on a column of silica gel, eluted with a 1:1 (v/v) ethyl acetate/petroleum ether mixture, 0.67 g of a white powder.

LC/MS: MH$^+$=259.

NMR 500 MHz (DMSO) δ ppm: 0.92 (t, 3H); 1.38 (m, 2H); 1.65 (m, 2H); 2.14 (s, 3H); 2.88 (m, 2H); 2.97 (s, 3H); 3.63 (s, 2H); 3.67 (m, 2H); 4.51 (m, 1H); 7.04 (d, 2H); 7.12 (t, 1H); 7.24-7.30 (m, 5H); 8.55 (d, 1H); 12.46 (s, 1H).

$\alpha_D^{20}$=−103° (c=1, MeOH).

The table which follows illustrates the chemical structures and physical properties of some examples of compounds according to the invention.

TABLE (I)

| Cpd. | R₁ | R₂, R'₂ | R₃ | R₄ | R₅ | R₆ | R₇, R₈ | alpha D (C = 1, MeOH) | NMR(DMSO d6 unless specified) * signifies 300 MHz . ** signifies 360 MHz - *** signifies 500 MHz |
|---|---|---|---|---|---|---|---|---|---|
| 1. | 3,5-difluorophenyl | H, H | —CH₃ | —COR₆ | —CH(CH₃)₂ | OCH₃ | — | — | 1.16 (d,6H), 1.25 (d,3H), 3.53 (s,2H), 3.77 (s,3H), 3.97 (m,1H), 4.36 (m,1H), 6.97 (d,9H), 7.10 (m,1H), 8.55 (d,1H), 12.47 (s,1H)** |
| 2. | 3,5-difluorophenyl | H, H | —CH₃ | —COR₆ | —CH(CH₃)₂CH₃ | OCH₃ | — | — | 0.91 (q,3H), 1.30(d,3H), 1.61 (m,2H), 3.06 (t,2H), 3.53 (s,2H), 3.77 (s,3H), 4.38 (m,1H), 6.98 (m,2H), 7.08 (m,1H), 8.57 (d,1H), 12.49 (s,1H)*** |
| 3. | 3,5-difluorophenyl | H, H | —CH₃ | —COR₆ | —CH₂CH(CH₃)₂ | OCH₃ | — | — | 0.89 (d,6H), 1.30 (d,3H), 1.85 (m,1H), 2.98 (d,2H), 3.53 (s,2H), 3.77 (s,3H), 4.38 (m,1H), 6.98 (d,2H), 7.09 (m,1H), 8.57 (d,1H), 12.50 (s,1H)** |
| 4. | 3,5-difluorophenyl | H, H | —CH₃ | —COR₆ | —CH₂C(CH₃)₃ | OCH₃ | — | — | 0.91 (s,9H), 1.31 (d,3H), 3.07 (s,2H), 3.53 (s,2H), 3.76 (s,3H), 4.38 (m,1H), 6.97 (d,2H), 7.08 (m,1H), 8.57 (d,1H), 12.51 (s,1H)** |
| 5. | 3,5-difluorophenyl | H, H | —CH₃ | —COR₆ | cyclohexyl | OCH₃ | — | — | 1.30 (d,3H), 1.31 (m,5H), 1.67-1.97 (m,5H), 3.53 (s,2H), 3.65 (m,1H), 3.77 (s,3H), 4.38 (m,1H), 6.98 (d,2H), 7.08 (m,1H), 9.67 (d,1H), 12.47 (s,1H)** |
| 6. | 3,5-difluorophenyl | H, H | —CH₃ | —COR₆ | —(CH₂)₅CH₃ | OCH₃ | — | — | 0.85 (t,3H), 1.29 (9H), 1.56 (m,2H), 3.10 (t,2H), 3.69 (t,2H), 3.77 (s,3H), 4.41 (m,1H), 6.97 (m,2H), 7.07 (m,1H), 8.56 (d,1H), 12.48 (s,1H)** |
| 7. | 3,4-difluorophenyl | H, H | —CH₃ | —COR₆ | phenyl | OCH₃ | — | — | 1.33 (d,3H), 3.50 (s,2H), 3.67 (s,3H), 4.42 (m,1H), 7.28-7.48 (m,3H), 8.57 (d,1H), 12.70 (s,1H)** |
| 8. | 3,4-difluorophenyl | H, H | —CH₃ | —COR₆ | benzyl | OCH₃ | — | — | 1.25 (d,3H), 3.48 (s,2H), 3.85 (s,2H), 4.35 (m,1H), 4.47 (s,2H), 7.20-7.40 (m,3H), 8.50 (d,1H), 12.50 (s,1H)** |
| 9. | 3,5-difluorophenyl | H, H | —CH₃ | —COR₆ | H | OCH₂CH₃ | — | — | 1.25 (t+d,6H), 3.65 (s,2H), 4.25 (m,2H), 4.45 (m,1H), 6.95 (d,2H), 7.10 (m,1H), 8.05 (s,1H), 8.57 (d,1H), 12.65 (s,1H)** |
| 10. | 3,5-difluorophenyl | H, H | —CH₃ | —COR₆ | —CH₃ | OCH₃ | — | — | 1.27 (d,3H), 2.57 (s,3H), 3.50 (s,2H), 3.74 (s,3H), 4.36 (m,1H), 6.96 (d,2H), 7.05 (m,1H), 8.53 (d,1H), 12.43 (s,1H)*** |

TABLE-continued (I)

| Cpd. | R₁ | R₂, R'₂ | R₃ | R₄ | R₅ | R₆ | R₇, R₈ | alpha D (C = 1, MeOH) | NMR(DMSO d6 unless specified) * signifies 300 MHz.  signifies 360 MHz - * signifies 500 MHz |
|---|---|---|---|---|---|---|---|---|---|
| 11. | 3,5-difluorophenyl | H, H | —CH₃ | —COR₆ | ![4-methylphenyl-CH(CH₃)] | OCH₃ | — | — | 1.22 (d,6H), 1.33 (d,3H), 2.93 (m,1H), 3.54 (s,2H), 3.68 (s,3H), 4.42 (m,1H), 6.98 (d,2H), 7.08 (m,1H), 7.29 (d,2H), 7.39 (d,2H), 8.60 (d,1H), 12.68 (s,1H)** |
| 12. | 3,5-difluorophenyl | H, H | —CH₃ | —COR₆ | —(CH₂)₂CH₃ | NR₇R₈ | cyclohexyl | — | 0.89 (t,3H), 1.29 (m,3H), 1.31 (3H), 1.22-1.87 (m,10H), 3.10(t,2H), 3.53 (s,2H), 3.67 (m,1H), 4.43 (m,1H), 6.98 (m,2H), 7.07 (m,1H), 7.41 (d,1H), 8.54 (d,1H), 12.18 (s,1H)*** |
| 13. | 3,5-difluorophenyl | H, H | —CH₃ | —COR₆ | phenyl | OH | — | — | 1.30 (d,3H), 2.98 (t,2H), 3.38 (t,2H), 3.50 (s,2H), 4.41 (m,1H), 6.98 (d,2H), 7.07 (m,1H), 716-7.28 (m,5H), 8.53 (d,1H)*** |
| 14. | 3,5-difluorophenyl | H, H | —CH₃ | —COR₆ | CH₃(CH₂)₂— | NR₇R₈ | cyclohexenyl-CH₂CH₂, H | — | 0.89 (t,3H), 1.30 (d,3H), 1.49 (m,4H), 1.95 (m,4H), 2.10 (m,2H), 3.11 (m,2H), 3.30 (m,2H), 3.53 (s,2H), 4.49 (m,1H), 5.39 (s,1H), 6.98 (d,2H), 7.09 (m,1H), 7.61 (t,1H), 8.54 (d,1H), 12.13 (s,1H)** |
| 15. | 3,5-difluorophenyl | H, H | CH₃(S) | —COR₆ | (CH₃)₂CH— | OH | — | — | 1.24 (d,6H), 1.27 (d,3H), 3.51 (s,2H), 4.02 (m,1H), 4.38 (m,1H), 6.98 (d,2H), 7.09 (m,1H), 8.56 (d,1H), 12.41 (s, 1H)*** |
| 16. | 3,5-difluorophenyl | H, H | CH₃(S) | —COR₆ | (CH₃)₂CH— | OCH₃ | — | — | 1.25 (d,6H), 1.30 (d,3H), 3.53 (s,2H), 3.78 (s,3H), 3.97 (m,1H), 4.36 (m,1H), 6.96-7.11 (m,3H), 8.56 (d,1H), 12.47 (s,1H)*** |
| 17. | 3,5-difluorophenyl | OH, H(S) | CH₃(S) | —COR₆ | (CH₃)₂CH— | OCH₃ | — | — | 1.25 (d,6H), 1.30 (d,3H), 3.78 (s,3H), 3.97 (m,1H), 4.40 (m,1H), 5.04 (d,1H), 6.55 (s,1H), 7.13 (m,3H), 8.34 (d,1H), 12.43 (s,1H)*** |
| 18. | 3,5-difluorophenyl | H, H | —(CH₂)₂CH₃(S) | —COR₆ | (CH₃)₂CH— | OCH₃ | — | — | 0.85(t,3H), 1.26 (d,6H), 1.28-1.65 (m,4H), 3.53 (m,2H), 3.78 (s,3H), 3.97 (m,1H), 4.36 (m,1H), 6.96 (d,2H), 7.08 (m,1H), 8.49 (d,1H), 12.52 |
| 19. | 3,5-difluorophenyl | OH, H(S) | —(CH₂)₂CH₃(S) | —COR₆ | (CH₃)₂CH— | OCH₃ | — | −53° | 0.80 (t,3H), 1.18 (m,2H), 1.22 (d,6H), 1.68 (m,2H), 3.78 (s,3H), 3.97 (m,1H), 4.43 (m,1H), 5.05 (d,1H), 6.55 (d,1H), 7.13 (m,3H), 8.24 (d,1H), 12.46 (s,1H)*** |

TABLE-continued

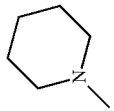

(I)

| Cpd. | R₁ | R₂, R'₂ | R₃ | R₄ | R₅ | R₆ | R₇, R₈ | alpha D (C = 1, MeOH) | NMR(DMSO d6 unless specified) * signifies 300 MHz.  signifies 360 MHz - * signifies 500 MHz |
|---|---|---|---|---|---|---|---|---|---|
| 20. | 3,5-difluorophenyl | OH, H(R) | —(CH₂)₂CH₃(S) | —COR₆ | (CH₃)₂CH— | OCH₃ | — | −83° | 0.82 (t,3H), 1.26 (d,6H), 1.26 (m,2H), 1.68 (m,2H), 3.78 (s,3H), 3.97 (m,1H), 4.40 (m,1H), 5.07 (d,1H), 6.42 (d,1H), 7.12 (m,3H), 8.27 (d,1H), 12.51 (s,1H)*** |
| 21. | 3,5-difluorophenyl | H, H | CH₃(CH₂)₂—(S) | —COR₆ | (CH₃)₂CH— | NR₇R₈ | 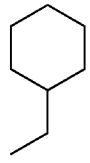 | — | 0.85 (t,3H), 1.22 (d,6H), 1.27-1.65 (m,1H), 3.19-3.30 (m,3H), 3.51-3.73 (m,4H), 4.40 (m,1H), 7.09-6.90 (m,3H), 8.49 (d,1H), 12.22 (s,1H)*** |
| 22. | 3,5-difluorophenyl | H, H | CH₃(CH₂)₂—(S) | —COR₆ | (CH₃)₃C— | OCH₃ | — | — | 0.85 (m,3H), 1.42 (s,9H), 1.30 (m,2H), 1.64 (m,2H), 3.29 (m,2H), 3.79 (s,3H), 4.37 (m, 1H), 6.98-7.09 (m,3H), 8.46 (d,1H), 12.39 (s,1H)*** |
| 23. | 3,5-difluorophenyl | H, H | CH₃(CH₂)₂—(S) | —COR₆ | cyclohexyl-CH₂CH₂— | OCH₃ | — | — | 0.85 (m,3H), 0.96 (t,2H), 0.95-1.69 (m,14H), 2.99 (t,2H), 3.54 (m,2H), 3.77 (s,3H), 4.37 (m,1H), 6.97 (d,2H), 7.08 (m,1H), 8.48 (d,1H), 12.51 (s,1H)*** |
| 24. | 3,5-difluorophenyl | H, H | CH₃(S) | —COR₆ | (CH₃)₂CH— | OC(CH₃)₃ | — | — | 1.26 (d,6H), 1.34 (d,3H), 1.51 (s,9H), 3.53 (s,2H), 3.90 (m,1H), 4.39 (m,1H), 6.93 (d,2H), 7.07 (m,1H), 8.51 (s,1H), 12.40 (s,1H)*** |
| 25. | 3,5-difluorophenyl | H, H | CH₃(CH₂)₃—(S) | —COR₆ | (CH₃)₂CH— | OCH₃ | — | — | 0.83 (t,3H), 1.25 (d,6H), 1.23-1.72 (m,6H), 3.55 (m,2H), 3.78 (s,3H), 3.97 (m,1H), 4.35 (m,1H), 7.09-6.97 (m,3H), 8.47 (d,1H), 12.49 (s,1H)*** |
| 26. | 3,5-difluorophenyl | H, H | CH₃(CH₂)₂—(S) | —COR₆ | (CH₃)₂CH— | NR₇R₈ | CH₃, CH₃ | −74° | 0.87 (t,3H), 1.24 (d,6H), 1.29-1.67 (m,4H), 2.86 (s,3H), 2.95 (s,3H), 3.22 (m,1H), 3.54 (m,2H), 4.41 (m,1H), 6.98 (d,2H), 7.08 (m,1H), 8.49 (d,1H), 12.21 (s,1H)*** |
| 27. | 3,5-difluorophenyl | OH, H(S) | CH₃(CH₂)₂—(S) | —COR₆ | (CH₃)₂CH— | OCH₃ | — | −54° | 0.81 (t,3H), 1.22 (m,2H), 1.43 (s,9H), 1.67 (m,2H), 3.78 (s,3H), 4.42 (m,1H), 5.05 (s,1H), 6.55 (s,1H), 7.12 (m,3H), 8.22 (d,1H), 12.37 (s,1H)*** |
| 28. | 3,5-difluorophenyl | OH, H(R) | CH₃(CH₂)₂—(S) | —COR₆ | (CH₃)₃C— | OCH₃ | — | −78° | 0.82 (t,3H), 1.25 (m,2H), 1.42 (s,9H), 1.69 (m,2H), 3.79 (s,3H), 4.40 (m,1H), 5.07 (d,1H), 6.42 (d,1H), 7.13 (m,3H), 8.26 (d,1H), 12.41 (s,1H)*** |
| 29. | 3,5-difluorophenyl | H, H | CH₃(CH₂)₂—(S) | —COR₆ | CH₃CH₂— | OCH₃ | — | −70° | 0.86 (t,3H), 1.27 (t,3H), 1.29-1.35 (m,2H), 1.63 (m,2H), 3.10 (q,2H), 3.54 (s,3H), 3.78 (s,3H), 4.39 (m,1H), 6.98 (d,2H), 7.07 (m,1H), 8.47 (d,1H), 12.50 (s,1H)*** |

TABLE-continued (I)

| Cpd. | R₁ | R₂, R'₂ | R₃ | R₄ | R₅ | R₆ | R₇, R₈ | alpha D (C = 1, MeOH) | NMR(DMSO d6 unless specified) * signifies 300 MHz.  signifies 360 MHz - * signifies 500 MHz |
|---|---|---|---|---|---|---|---|---|---|
| 30. | phenyl | OH, H(S) | CH₃(CH₂)₂— (S) | —COR₆ | (CH₃)₂CH— | OCH₃ | — | −51° | 0.80 (t,3H), 1.16 (m,2H), 1.26 (s,9H), 1.68 (m,2H), 3.78 (s,3H), 3.97 (m,1H), 4.43 (m,1H), 4.98 (d,1H), 6.31 (6,1H), 7.32 (m,5H), 8.14 (d,1H), 12.46 (s,1H)*** |
| 31. | phenyl | OH, H(R) | CH₃(CH₂)₂— (S) | —COR₆ | (CH₃)₂CH— | OCH₃ | — | −110° | 0.85 (t,3H), 1.28 (s,6H), 1.28 (m,2H), 1.68 (m,2H), 3.78 (s,3H), 3.97 (m,1H), 4.44 (m,1H), 5.00 (d,1H), 6.17 (d,1H), 7.30 (m,5H), 8.17 (d,1H), 12.51 (s,1H)*** |
| 32. | 3,5-difluorophenyl | OH, H | CH₃(CH₂)₂— (S) | —COR₆ | (CH₃)₂CH— | OCH₃ | — | −66° | 0.85 (m,3H), 1.28 (d,6H), 1.30 (m,2H), 3.78 (s,3H), 3.96 (m,1H), 4.45 (m,1H), 5.20 and 5.22 (2s,1H), 6.44-6.50 (2s,1H), 7.05 (m,1H), 7.19 (m,1H), 7.44 (m,1H), 8.19 and 8.23 (2d,1H), 12.50 (s,1H)*** |
| 33. | 3,4-difluorophenyl | OH, H | CH₃(CH₂)₂— (S) | —COR₆ | (CH₃)₂CH— | OCH₃ | — | −67° | 0.82 (m,3H), 1.26 (d,6H), 3.97 (m,1H), 4.41 (m,1H), 5.03 (m,1H), 6.35 and 6.48 (2s,1H), 7.27 (m,1H), 7.42 (m,2H), 8.23 (m,1H), 12.48 (d,1H)*** |
| 34. | 2-chlorophenyl | OH, H | CH₃(CH₂)₂— (S) | —COR₆ | (CH₃)₂CH— | OCH₃ | — | −127° | 0.86 (t,3H), 1.26 (d,6H), 1.29 (m,2H), 1.78 (m,2H), 3.78 (s,3H), 3.97 (m,1H), 4.46 (m,1H), 5.33 (s,1H), 6.44 (s,1H), 7.29 (d,2H), 7.39 (d,1H), 7.45 (d,1H), 8.24 (d,1H), 12.51 (s,1H)*** |
| 35. | 3-chlorophenyl | OH, H(R) | CH₃(CH₂)₂— (S) | —COR₆ | (CH₃)₂CH— | OCH₃ | — | −77° | 0.83 (t,3H), 1.23 (d,6H), 1.29 (m,2H), 1.69 (m,2H), 3.78 (s,3H), 3.96 (m,1H), 4.39 (m,1H), 5.04 (s,1H), 6.31 (s,1H), 7.30-7.46 (m,4H), 8.24 (d,1H), 12.51 (s,1H)*** |
| 36. | 2-chlorophenyl | OH, H | CH₃(CH₂)₂— (S) | —COR₆ | (CH₃)₂CH— | OCH₃ | — | −65° | 0.86(t,3H), 1.26 (d,6H), 1.34 (m,2H), 1.73 (m,2H), 3.78 (s,3H), 3.96 (m,1H), 4.46 (m,1H), 5.34 (d,1H), 6.44 and 6.49 (2s,1H), 7.30 and 7.42 (2m,4H), 8.18 and 8.23 (2d,1H), 12.50 (d,1H)*** |
| 37. | 2,6-difluorophenyl | OH, H | CH₃(CH₂)₂— (S) | —COR₆ | (CH₃)₂CH— | OCH₃ | — | −66° | 0.87 (t,3H), 1.26 (s,6H), 1.28 (m,2H), 3.79 (s,3H), 3.98 (m,1H), 4.54 (m,1H), 5.28 (d,1H), 6.69 and 6.73 (2d,1H), 7.06 (m,2H), 7.39 (m,1H), 8.11 and 8.21 (2d,1H), 12.54 (s,1H)*** |
| 38. | phenylethyl (benzyl-CH₂) | OH, H(S) | — | —COR₆ | (CH₃)₂CH— | OCH₃ | — | −58° | 0.81 (t,3H), 1.10 (m,2H), 1.26 (d,6H), 1.60 (m,2H), 2.74 and 2.95.(dd,2H), 3.78 (s,3H), 3.95 (m,1H), 4.15 (m,1H), 4.45 (m,1H), 5.69 (d,1H), 7.18 (m,5H), 7.80 (d,1H), 12.44 (s,1H)*** |

TABLE-continued (I)

| Cpd. | R₁ | R₂, R'₂ | R₃ | R₄ | R₅ | R₆ | R₇, R₈ | alpha D (C = 1, MeOH) | NMR(DMSO d6 unless specified) * signifies 300 MHz.  signifies 360 MHz - * signifies 500 MHz |
|---|---|---|---|---|---|---|---|---|---|
| 39. | 3-methylbenzothiophene | OH, H(R) | CH₃(CH₂)₂— (S) | —COR₆ | (CH₃)₂CH— | OCH₃ | — | −6° | 0.84(t,3H), 1.18 (m,2H), 1.26 (m,6H), 1.64 (m,2H), 2.70 and 2.93 (dd,2H), 3.79 (s,3H), 3.98 (m,1H), 4.14 (m,1H), 4.45 (m,1H), 5.57 (d,1H), 7.09-7.21 (m,5H), 7.95 (d,1H), 12.44 (s,1H)*** |
| 40. | cyclohexyl | OH, H(S) | CH₃(CH₂)₂— (S) | —COR₆ | (CH₃)₂CH— | OCH₃ | — | −59° | 0.85 (t,3H), 1.11-1.18 (m,7H), 1.24 (d,6H), 1.28 (m,1H), 1.65-1.69 (m,7H), 3.69 (d,1H), 3.78 (s,3H), 3.97 (m,1H), 4.50 (m,1H), 5.46 (d,1H), 7.80 (d,1H), 12.44 (s,1H)*** |
| 41. | cyclohexyl | OH, H(R) | CH₃(CH₂)₂— (S) | —COR₆ | (CH₃)₂CH— | OCH₃ | — | insoluble MeOH | 0.85 (t,3H), 1.25 (d,6H), 1.05-1.67 (m,15H), 3.70 (d,1H), 3.78 (s,3H), 3.96 (m,1H), 4.45 (m,1H), 5.34 (d,1H), 7.82 (d,1H), 12.50 (s,1H)*** |
| 42. | 3,5-difluorophenyl | OH, H(S) | CH₃(CH₂)₃— (S) | —COR₆ | (CH₃)₂CH— | OCH₃ | — | −49° | 0.78(t,3H), 1.18 (m,4H), 1.27 (d,6H), 1.71 (m,1H), 3.78 (s,3H), 3.97 (m,1H), 4.42 (m,1H), 5.05 (m,1H), 6.56 (s,1H), 7.13 (m,3H), 8.23 (d, 1H), 12.45 (s,1H)*** |
| 43. | 3,5-difluorophenyl | OH, H(S) | CH₃(CH₂)₂— (S) | —COR₆ | cyclohexylmethyl | OCH₃ | — | — | 0.80 (t,3H), 0.95 (m,2H), 1.13-1.69 (m,13H), 2.99 (d,2H), 3.77 (s,3H), 4.42 (m,1H), 5.05 (s,1H), 6.55 (s,1H), 7.11 (m,3H), 8.24 (d,1H), 12.51 (s,1H)*** |
| 44. | 3,5-difluorophenyl | OH, H(S) | CH₃(CH₂)₂— (S) | —COR₆ | CH₃CH₂— | OCH₃ | — | −55° | 0.80 (t,3H), 1.19 (d,3H), 1.20 (m,1H), 1.69 (m,2H), 3.09 (m,2H), 3.78 (s,3H), 4.41 (m,1H), 5.05 (s,1H), 6.55 (s,1H), 7.12 (m,3H), 8.26 (d,1H), 12.45 (s,1H)*** |
| 45. | 3,5-difluorophenyl | OH, H(R) | CH₃(CH₂)₂— (S) | —COR₆ | CH₃CH₂— | OCH₃ | — | — | 0.83 (t,3H), 1.22 (t,3H), 1.28 (m,1H), 1.69 (m,2H), 3.09 (m,2H), 3.78 (s,3H), 4.40 (m,1H), 5.07 (s,1H), 6.42 (s,1H), 7.12 (m,3H), 8.29 (d,1H), 12.51 (s,1H)*** |
| 46. | 3,5-difluorophenyl | H, H | CH₃(CH₂)₂— (S) | —COR₆ | (CH₃)₂CH— | NR₇R₈ | CH₃CH₂, CH₃CH₂ | — | 0.85 (t,3H), 1.03-1.11 (m,6H), 1.20 (d,6H), 1.20-1.32 (m,2H), 1.60 (m,2H), 3.18 (m,3H), 3.39 (m,2H), 3.55 (s,2H), 4.42 (m,1H), 6.98 (d,2H), 7.07 (m,1H), 8.49 (d, 1H), 12.21 (s,1H)*** |
| 47. | 3,5-difluorophenyl | H, H | CH₃(CH₂)₂— (S) | —COR₆ | (CH₃)₂CH— | NR₇R₈ | morpholine | −66° | 0.85 (t,3H), 1.21 (d,6H), 1.34-1.22 (m,2H), 1.64 (m,2H), 3.26 (m,1H), 3.27 (s,2H), 3.50 (s,2H), 3.51 (s,2H), 3.57 (s,4H), 4.41 (m,1H), 6.97 (d,2H), 7.08 (m,1H), 8.49 (s,1H), 12.25 (s,1H)*** |

TABLE-continued (I)

| Cpd. | R₁ | R₂, R'₂ | R₃ | R₄ | R₅ | R₆ | R₇, R₈ | alpha D (C = 1, MeOH) | NMR(DMSO d6 unless specified) * signifies 300 MHz.  signifies 360 MHz - * signifies 500 MHz |
|---|---|---|---|---|---|---|---|---|---|
| 48. | 3,5-difluorophenyl | H, H | CH₃(CH₂)₂— (S) | —COR₆ | (CH₃)₂CH— | NR₇R₈ | CH₃, H | — | 0.86 (t,3H), 1.22 (d,6H), 1.35 (m,2H), 1.63 (m,2H), 2.75 (s,3H), 3.58 (d,2H), 4.18 (m,1H), 4.47 (m,1H), 6.98 (d,2H), 7.07 (m, 1H), 7.69 (s,1H), 8.50 (s,1H), 12.13 (s,1H)*** |
| 49. | 3,5-difluorophenyl | H, H | CH₃(CH₂)₂— (S) | —COR₆ | (CH₃)₂CH— | NR₇R₈ | azetidinyl | — | 0.86 (m,3H), 1.21 (d,6H), 1.34 (m,2H), 1.62 (m,2H), 2.20 (m,2H), 3.54 (s,2H), 3.97 (m,2H), 4.38 (m,2H), 4.47 (m,1H), 6.97 (d,2H), 7.08 (m,1H), 8.52 (d,1H), 12.08 (s,1H)*** |
| 50. | 3,5-difluorophenyl | H, H | CH₃(CH₂)₂— (S) | —COR₆ | phenyl | OCH₃ | — | −112° | 0.87 (t,3H), 1.30 (m,2H), 1.67 (m,2H), 3.56 (s,2H), 3.67 (s,3H), 4.43 (m,1H), 6.98 (d,2H), 7.06 (m,1H), 7.44 (m,5H), 8.56 (d,1H), 12.71 (s,1H)*** |
| 51. | 3,5-difluorophenyl | H, H | CH₃(CH₂)₂— (S) | —COR₆ | (CH₃)₂CH— | OCH₃ | — | −73° | 0.79 (t,3H), 1.26 (d,6H), 1.73 (m,2H), 3.78 (s,3H), 3.96 (m,1H), 4.36 (m,1H), 5.06 (s,4H), 6.56 (s,1H), 7.13 (m,3H), 8.22 (d,1H), 12.46 (s,1H)*** |
| 52. | phenyl | —OCH₃, H(S) | CH₃(CH₂)₂— (S) | —COR₆ | (CH₃)₂CH— | OCH₃ | — | −37° | 086 (t,3H), 1.25 (m,2H), 1.30 (d,6H), 1.75 (m,2H), 3.38 (s,3H), 3.79 (s,3H), 4.00 (m,1H), 4.47 (m,1H), 4.75 (s,1H), 7.33 (m,5H), 8.22 (d,1H), 12.50 (s,1H)*** |
| 53. | phenyl | —OCH₃, H(R) | CH₃(CH₂)₂— (S) | —COR₆ | (CH₃)₂CH— | OCH₃ | — | −113° | 0.85 (t,3H), 1.27 (d,6H), 1.26 (m,2H), 1.70 (m,2H), 3.30 (s,3H), 3.80 (s,3H), 3.98 (m,1H), 4.41 (m,1H), 4.77 (s,1H), 7.30 (m,5H), 8.30 (d,1H), 12.50 (s,1H)*** |
| 54. | phenyl | OH, CH₃ (S) | CH₃(CH₂)₂— (S) | —COR₆ | (CH₃)₂CH— | OCH₃ | — | −66° | 0.77 (t,3H), 1.10-1.17 (m,2H), 1.35 (d,6H), 1.68 (s,3H), 3.85 (s,3H), 4.05 (m,1H), 4.45 (m,1H), 6.30 (s,1H), 7.25-7.50 (m,5H), 8.00 (d,1H), 12.47 (s,1H)*** |
| 55. | phenyl | OH, CH₃ (R) | CH₃(CH₂)₂— (S) | —COR₆ | (CH₃)₂CH— | OCH₃ | — | −61° | 0.90 (t,3H), 1.28 (d,6H), 1.30 (m,2H), 1.65 (m,2H), 1.71 (m,2H), 3.83 (s,3H), 4.00 (m,1H), 6.28 (s,1H), 7.22-7.50 (m,5H), 8.00 (d,1H), 12.50 (s,1H)*** |
| 56. | 3,5-difluorophenyl | H, H | CH₃(CH₂)₂— (S) | —COR₆ | (CH₃)₂CH— | NR₇R₈ | (CH₃)₂CH—, CH₃ | — | 0.86 (t,3H), 1.07 (m,6H), 1.11 (m,6H), 1.21 (m,2H), 1.62 (m,2H), 2.66 (s,3H), 2.81 (s,3H), 3.27 (m,1H), 3.54 (s,2H), 3.77 (m,1H), 4.41 (m,1H), 6.97 (d,2H), 7.07 (m,1H), 8.48 (d,1H), 12.20 (s,1H)*** |
| 57. | 3,5-difluorophenyl | OH, H | CH₃(CH₂)₂— (S) | —COR₆ | (CH₃)₂CH— | NR₇R₈ | CH₃, CH₃ | −119° | 0.72 (t,3H), 1.06 (m,1H), 1.16 (m,1H), 1.27 (d,6H), 1.58 (m,2H), 2.10 (s,3H), 3.78 (s,3H), 3.96 (m,1H), 4.37 (m,1H), 5.97 (s,1H), 7.34 and 7.47 (2m,5H), 8.62 (s,1H), 12.49 (s,1H)*** |

TABLE-continued (I)

| Cpd. | R₁ | R₂, R'₂ | R₃ | R₄ | R₅ | R₆ | R₇, R₈ | alpha D (C = 1, MeOH) | NMR(DMSO d6 unless specified) * signifies 300 MHz.  signifies 360 MHz - * signifies 500 MHz |
|---|---|---|---|---|---|---|---|---|---|
| 58. | 3,5-difluorophenyl | H, H | CH₃(CH₂)₂— (S) | —COR₆ | (CH₃)₂CH— | NR₇R₈ | CH₃, OCH₃ | — | 0.86 (t,3H), 1.23 (s,6H), 1.28-1.35 (m,2H), 1.64 (m,2H), 3.20 (s,3H), 3.30 (m,1H), 3.52 (s,3H), 4.42 (m,1H), 6.98 (d,2H), 7.08 (m,1H), 8.49 (d,1H), 12.23 (s,1H)*** |
| 59. | 3,5-difluorophenyl | H, H | CH₃OCH₂— (S) | —COR₆ | (CH₃)₂CH— | OCH₃ | — | — | 1.26 (t,3H), 3.28 (d,3H), 3.55 (s,2H), 3.57 (m,2H), 3.78 (s,3H), 3.97 (m,1H), 4.64 (m,1H), 6.98 (d,2H), 7.08 (m,1H), 8.57 (d,1H), 12.54 (s,1H)*** |
| 60. | 3,5-difluorophenyl | OH, H(S) | CH₃OCH₂— (S) | —COR₆ | (CH₃)₂CH— | OCH₃ | — | — | 1.25 (d,6H), 3.23 (s,2H), 3.59 (m,1H), 3.61 (m,1H), 3.78 (s,3H), 3.96 (m,1H), 4.64 (m,1H), 5.09 (s,1H), 6.62 (s,1H), 7.13 (m,3H), 8.23 (d,1H), 12.53 (s,1H)*** |
| 61. | 3,5-difluorophenyl | OH, H(R) | CH₃OCH₂— (S) | —COR₆ | (CH₃)₂CH— | OCH₃ | — | — | 1.26 (t,3H), 3.23 (s,2H), 3.62 (m,1H), (m,1H), 3.78 (s,3H), 3.97 (m,1H), 4.00 (m,1H), 5.10 (s,1H), 6.56 (s,1H), 7.13 (m,3H), 8.26 (d,1H), 12.59 (s,1H)*** |
| 62. | ![structure with phenyl-CH(OH)CH₃] | H, H | CH₃(CH₂)₂— (S) | —COR₆ | (CH₃)₂CH— | OCH₃ | — | — | 0.86 (t,3H), 1.27 (d,6H), 1.28 (m,2H), 1.62 (m,2H), 3.78 (s,3H), 3.97 (m,1H), 4.41 (m,1H), 4.94 (m,1H), 5.33 (s,1H), 7.21 (m,5H), 8.13 (d,1H), 12.41 |
| 63. | ![structure with phenyl-CH(OH)CH₃] | H, H | CH₃(CH₂)₂— (S) | —COR₆ | (CH₃)₂CH— | OCH₃ | — | — | 0.79 (t,3H), 1.12 (d,6H), 1.27 (d,6H), 1.51 (m,2H), 3.78 (s,3H), 3.96 (m,1H), 4.37 (m,1H), 4.91 (m,1H), 5.34 (s,1H), 7.30 (m,5H), 8.09 (d,1H), 12.38 (s,1H)*** |
| 64. | 3,5-difluorophenyl | H, H | CH₃(CH₂)₂— (S) | —COR₆ | (CH₃)₂CH— | NR₇R₈ | CH₃CH₂—, CH₃ | — | 0.86 (t,3H), 1.05 (m,3H), 1.07 (d,6H), 1.08 (m,2H), 1.21 (m,2H), 2.82 and 2.92 (2s,3H), 3.20 (m,2H), 3.30 (m,1H), 3.55 (s,2H), 4.41 (m,1H), 6.98 (d,2H), 7.09 (m,1H), 8.49 (m,1H), 12.19 (s,1H)*** |
| 65. | phenyl | H, H | CH₃(CH₂)₂— (S) | —COR₆ | (CH₃)₂CH— | OCH₃ | — | — | 0.85 (t,3H), 1.26 (d,6H), 1.34 (m,2H), 3.46 (q,2H), 3.78 (s,3H), 3.97 (m,1H), 4.36 (m,1H), 7.24 (m,5H), 8.38 (d,1H), 12.47 (s,1H)*** |

TABLE-continued (I)

| Cpd. | $R_1$ | $R_2, R'_2$ | $R_3$ | $R_4$ | $R_5$ | $R_6$ | $R_7, R_8$ | alpha D (C = 1, MeOH) | NMR(DMSO d6 unless specified) * signifies 300 MHz.  signifies 360 MHz - * signifies 500 MHz |
|---|---|---|---|---|---|---|---|---|---|
| 66. | 2,3-difluorophenyl | OH, H | $CH_3(CH_2)_2$— (S) | —$COR_6$ | $(CH_3)_2CH$— | $OCH_3$ | — | −71° | 0.86 (m,3H), 1.26 (d,6H), 1.28 (m,2H), 1.72 (m,2H), 3.78 (s,3H), 3.96 (m,1H), 4.47 (m, 1H), 5.24 and 5.28 (2d,1H), 6.55 and 6.62 (2d,1H), 7.17-7.36 (m,3H), 8.19 and 8.23 (dd,1H), 12.49 (s,1H)*** |
| 67. | 2,3-difluorophenyl | OH, H | $CH_3(CH_2)_2$— (S) | —$COR_6$ | $(CH_3)_2CH$— | $OCH_3$ | — | −68° | 0.85 (m,3H), 1.26 (d,6H), 1.30 (m,2H), 1.72 (m,2H), 3.78 (s,3H), 3.97 (m, 1H), 4.45 (m,1H), 5.20 and 5.23 (2s,1H), 6.50 and 6.57 (2s,1H), 7.18 (m,3H), 8.19 and 8.25 (dd,1H), 12.48 (s,1H)*** |
| 68. | phenyl | =O | $CH_3(CH_2)_2$— (S) | —$COR_6$ | $(CH_3)_2CH$— | $OCH_3$ | — | −40° | 0.97 (t,3H), 1.20 (d,6H), 1.40 (m,2H), 1.80 (m,2H), 3.87 (s,3H), 4.05 (m,1H), 4.60 (m,1H), 7.60 (m,2H), 7.80 (m,1H), 7.99 (m,2H), 9.30 (d,1H), 12.70 (s,1H)** |
| 69. | 3,4-methylenedioxyphenyl | OH, H | $CH_3(CH_2)_2$— (S) | —$COR_6$ | $(CH_3)_2CH$— | $OCH_3$ | — | −66° | 0.86 (m,3H), 1.30 (d,6H), 1.25 (m,2H), 1.72 (m,2H), 3.81 (s,3H), 4.00 (m, 1H), 4.45 (m,1H), 4.90 and 4.94 (dd,1H), 5.99 (m,2H), 6.13 and 6.26 (dd,1H), 6.86 (m,3H), 8.14 (m,1H), 12.47 and 12.52 (d,1H)*** |
| 70. | phenyl | —(OC(O)CH_3, H(S) | $CH_3(CH_2)_2$— (S) | —$COR_6$ | $(CH_3)_2CH$— | $OCH_3$ | — | — | 0.86 (m,3H), 1.24 (d,6H), 1.26 (m,2H), 1.63 (m,2H), 2.11 (s,3H), 3.77 (s,3H), 3.95 (m,1H), 4.45 (m,1H), 5.94 (s,1H), 7.38 (m,5H), 8.55 (d,1H), 2.48 (s,1H)*** |
| 71. | phenyl | —(OC(O)CH_3, H(R) | $CH_3(CH_2)_2$— (S) | —$COR_6$ | $(CH_3)_2CH$— | $OCH_3$ | — | — | 0.81 (t,3H), 1.21 (d,6H), 1.22 (m,2H), 1.67 (m,2H), 2.86 (s,3H), 2.95 (s,3H), 3.22 (m,1H), 4.44 (m,1H), 5.06 (m,1H), 6.54 and 6.41 (2s,1H), 7.13 (m,3H), 8.26 (d,1H), 12.19 (s,1H)*** |
| 72. | 3,5-difluorophenyl | OH, H(S) | $CH_3(CH_2)_2$— (S) | —$COR_6$ | $(CH_3)_2CH$— | $OCH_3$ | — | — | 0.79 (t,3H), 1.25 (d,6H), 3.78 (s,3H), 3.96 (m,1H), 4.36 (m,1H), 5.06 (s,1H), 6.56 (s,1H), 7.13 (m,3H), 8.22 (d,1H), 12.46 (s,1H)*** |
| 73. | 3,5-difluorophenyl | OH, H(R) | $CH_3(CH_2)_2$— (S) | —$COR_6$ | $(CH_3)_2CH$— | $OCH_3$ | — | — | 0.83 (t,3H), 1.26 (d,6H), 1.73 (m,2H), 3.78 (s,3H), 3.95 (m,1H), 4.32 (m,1H), 5.08 (s,1H), 6.44 (s,1H), 7.12 (m,3H), 8.26 (d,1H), 12.50 (s,1H)*** |
| 74. | 3,5-difluorophenyl | H, H | $CH_3(CH_2)_2CH$— (S) | —$COR_6$ | $(CH_3CH_2)_2CH$— | $OCH_3$ | — | — | 0.77 (m,6H), 0.83 (t,3H), 1.43-1.75 (m,8H), 3.53 (d,2H), 3.70 (m,1H), 3.77 (s,3H), 4.36 (m,1H), 6.98 (m,2H), 7.08 (m,1H), 8.46 (d,1H), 12.51 (s,1H)*** |

TABLE-continued (I)

| Cpd. | R₁ | R₂, R'₂ | R₃ | R₄ | R₅ | R₆ | R₇, R₈ | alpha D (C = 1, MeOH) | NMR(DMSO d6 unless specified) * signifies 300 MHz .  signifies 360 MHz - * signifies 500 MHz |
|---|---|---|---|---|---|---|---|---|---|
| 75. | 3,5-difluorophenyl | O (ketone) | CH₃(CH₂)₂— (S) | —COR₆ | (CH₃)₂CH— | OCH₃ | — | — | 0.89 (t,3H), 1.28 (d,6H), 1.33 (m,2H), 1.77 (m,2H), 3.78 (s,3H), 3.98 (m,1H), 4.56 (m,1H), 7.70 (m,3H), 9.36 (d,1H), 12.62 (s,1H)*** |
| 76. | CH3S(CH2)2— | OH, H | CH₃(CH₂)₂— (S) | —COR₆ | (CH₃)₂CH— | OCH₃ | — | — | 0.93 (t,3H), 1.38 (d,6H), 1.39 (m,2H), 1.74-1.90 (m, 2H), 2.10 (s,3H), 2.56 (s,2H), 3.85 (s,3H), 4.04 (m,1H), 4.08 (m,1H), 4.51 (m,1H), 5.73 (d,1H), 7.97 (d,1H), 12.50 (s,1H)*** |
| 77. | (CH3)2CHCH2— | OH, H(S) | CH₃(CH₂)₂— (S) | —COR₆ | (CH₃)₂CH— | OCH₃ | — | — | 0.87 (m,9H), 1.27 (d,6H), 1.26-1.39 (m,4H), 1.67 (m,3H), 3.78 (s,3H), 3.90 (m,2H), 4.45 (m,1H), 5.49 (d,1H), 7.85 (d,1H), 12.43 (s,1H)*** |
| 78. | 3,5-difluorophenyl | OH, H(S) | CH₃CH₂CH— (S) | —COR₆ | (CH₃)₂CH— | OCH₃ | — | −61° | 0.80 (m,9H), 1.25 (m,2H), 1.50 (m,2H), 1.70 (m,4H), 3.73 (m,1H), 3.80 (s,3H), 4.45 (m,1H), 5.05 (s,1H), 6.55 (s,1H), 7.15 (m,3H), 8.25 (d,1H), 12.43 (s,1H)*** |
| 79. | 3,5-difluorophenyl | OH, H(R) | CH₃CH₂CH— (S) | —COR₆ | (CH₃)₂CH— | OCH₃ | — | — | 0.80 (m,6H), 0.85 (m,3H), 1.30 (m,2H), 1.50 (m,2H), 1.75 (m,4H), 3.75 (m,1H), 3.85 (s,3H), 4.45 (m,1H), 5.11 (s,1H), 6.45 (s,1H), 7.18 (m,3H), 8.31 (d,1H), 12.60 (s,1H)*** |
| 80. | 3,5-difluorophenyl | H, H | CH₃(CH₂)₂— (S) | —COR₆ | cyclopropyl | OCH₃ | — | −96° | 0.78 (d,2H), 0.88 (t,3H), 1.20 (d,2H), 1.25-1.40 (m, 2H), 1.68 (m,2H), 2.90 (m,1H), 3.55 (m,2H), 3.82 (s,3H), 4.38 (m,1H), 7.00-7.15 (m,3H), 8.50 (d,1H), 12.48 (s,1H)*** |
| 81. | 3,5-difluorophenyl | OH, H(S) | CH₃(CH₂)₂— (S) | —COR₆ | cyclopropyl | OCH₃ | — | −56° | 0.75 (m,2H), 0.82 (t,3H), 1.22 (m,2H), 1.70 (m,2H), 2.90 (m,1H), 3.80 (s,3H), 4.42 (m,1H), 5.08 (s,1H), 6.48 (s,1H), 7.13 (m,3H), 8.25 (d,1H), 12.48 (s,1H)*** |
| 82. | 3,5-difluorophenyl | OH, H(R) | CH₃(CH₂)₂— (S) | —COR₆ | cyclopropyl | OCH₃ | — | −84° | 0.78 (m,2H), 0.90(m,3H), 1.20 (m,2H), 1.30 (m,2H), 1.70 (m,2H), 2.90 (m,1H), 3.85 (s,3H), 4.40 (m,1H), 5.10 (s,1H), 6.42 (s,1H), 7.18 (m,3H), 8.30 (d,1H), 12.55 (s,1H)*** |
| 83. | phenyl | CH₃(CH₂)₂—, H(S) | CH₃(CH₂)₂— (S) | —COR₆ | (CH₃)₂CH— | OCH₃ | — | −25° | 0.80 (t,3H), 0.86 (t,3H), 1.26 (d,6H), 1.30-1.40 (m,2H), 1.65 (m,2H), 3.50 (m,1H), 3.80 (s,3H), 3.95 (m,1H), 4.45 (m,1H), 7.20-7.30 (m,5H), 8.30 (d,1H), 12.45 (s,1H)*** |

TABLE-continued (I)

| Cpd. | R₁ | R₂, R'₂ | R₃ | R₄ | R₅ | R₆ | R₇, R₈ | alpha D (C = 1, MeOH) | NMR(DMSO d6 unless specified) * signifies 300 MHz.  signifies 360 MHz - * signifies 500 MHz |
|---|---|---|---|---|---|---|---|---|---|
| 84. | phenyl | CH₃(CH₂)₂—, H(R) | CH₃(CH₂)₂— (S) | —COR₆ | (CH₃)₂CH— | OCH₃ | — | — | 0.80(t,3H), 0.85(t,3H), 1.18-1.30 (m,2H), 1.30 (d,6H), 1.60 (m,2H), 1.95 (m,2H), 3.50 (m,1H), 3.80 (s,3H), 4.00 (m,1H), 4.30 (m,2H), 7.20-7.30 (m,5H), 8.32 (d,1H), 12.45 (s,1H)*** |
| 85. | phenyl | CH₃, H(S) | CH₃(CH₂)₂— (S) | —COR₆ | (CH₃)₂CH— | OCH₃ | — | −17° | 0.91 (t,3H), 1.30 (d,6H), 1.38(d,3H), 1.30-1.45 (m,2H), 1.68 (m,2H), 3.80 (m,1H), 3.85 (s,3H), 4.00 (m, 1H), 4.48 (m,1H), 7.21-7.30 (m,5H), 8.30 (d,2H), 12.48 (s,1H)*** |
| 86. | phenyl | CH₃, H(R) | CH₃(CH₂)₂— (S) | —COR₆ | (CH₃)₂CH— | OCH₃ | — | — | 0.78 (t,3H), 1.14-1.25 (m,2H), 1.30 (m,6H), 1.57 (m,2H), 3.72 (m,1H), 3.75 (s,3H), 3.98 (m,1H), 4.31 (m,1H),7.24-7.40 (m,5H), 8.26 (d,1H), 12.45 (s, 1H)*** |
| 87. | phenyl | cyclohexyl-CH | CH₃(CH₂)₂— (S) | —COR₆ | (CH₃)₂CH— | OCH₃ | — | — | 0.78 and 0.90 (2t,3H), 0.60-2.00 (m,15H), 1.25 and 1.35 (2d,6H), 3.30 (m,1H), 3.80 (2s,3H), 4.00 (m,1H), 4.25 and 4.45 (2m,1H), 7.20-7.35 (m,5H), 8.30 (m,1H), 12.45 (m,1H)*** |
| 88. | 3,5-difluorophenyl | OH, H(S) | CH₃(CH₂)₂— (S) | —COR₆ | (CH₃)₂CH— | NR₇R₈ | CH₃, CH₃ | — | 0.80 (t,3H), 1.25 (d,6H), 1.28 (m,2H), 1.75 (m,2H), 2.80 (s,3H), 3.00 (s,3H), 3.25 (m,1H), 4.49 (m1H), 5.08 (s,1H), 6.55 (broad s,1H), 7.13 (d,3H), 8.25 (d,1H), 12.15 (s,1H)*** |
| 89. | 3,5-difluorophenyl | OH, H(R) | CH₃(CH₂)₂— (S) | —COR₆ | (CH₃)₂CH— | NR₇R₈ | CH₃, CH₃ | −64° | 0.88 (t,3H), 1.22 (d,6H), 1.30 (m,2H), 1.68 (m,2H), 2.87 (s,3H), 2.98 (s,3H), 3.25 (m,1H), 4.45 (m,H), 5.10 (s,1H), 6.42 (s,1H), 7.18 (m,5H), 8.30 (d,1H), 12.20 (s,1H)*** |
| 90. | 3,5-difluorophenyl | H, H | CH₃(CH₂)₂— (S) | —COR₆ | H | OCH₂CH₃ | — | — | 0.89 (t,3H), 1.28 (t,3H), 1.35 (m,2H), 1.65 (m,2H), 3.58 (m,2H), 4.28 (m,1H), 4.40 (m,1H), 6.98 (d,2H), 7.08 (t,1H), 8.05 (s,1H), 8.50 (d,1H), 12.67 (s,1H)*** |
| 91. | cyclohexyl | H, H | CH₃(CH₂)₂— (S) | —COR₆ | (CH₃)₂CH— | OCH₃ | — | — | 0.85 (t,3H), 0.90 (m,3H), 1.30 (m,2H), 1.30 (d,6H), 1.60 (m,9H), 2.00 (m,2H), 3.80 (s,3H), 3.98 (m,1H), 4.36 (m,1H), 8.08 (d1,1H), 12.40 (s,1H)*** |
| 92. | 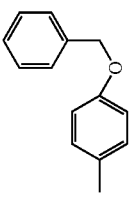 | H, H | CH₃(CH₂)₂— (S) | —COR₆ | (CH₃)₂CH— | OCH₃ | — | — | 0.85 (t,3H), 1.28 (d,6H), 1.30 (m,2H), 1.60 (m,1H), 3.60 (m,2H), 3.80 (s,1H), 4.00 (m,1H), 5.10 (s,2H), 6.86-7.46 (m,9H), 8.18 (d,1H), 12.42 (s,1H)*** |

TABLE-continued (I)

| Cpd. | R$_1$ | R$_2$, R'$_2$ | R$_3$ | R$_4$ | R$_5$ | R$_6$ | R$_7$, R$_8$ | alpha D (C = 1, MeOH) | NMR(DMSO d6 unless specified) * signifies 300 MHz.  signifies 360 MHz - * signifies 500 MHz |
|---|---|---|---|---|---|---|---|---|---|
| 93. | 3-hydroxyphenyl | H, H | CH$_3$(CH$_2$)$_2$— (S) | —COR$_6$ | (CH$_3$)$_2$CH— | OCH$_3$ | — | — | 0.88 (t,3H), 1.28 (d,6H), 1.75 (m,2H), 3.50 (m,2H), 3.80 (s,3H), 4.00 (m,1H), 4.40 (m,1H), 6.70-7.10 (m,4H), 8.25 (s,1H), 9.55 (s,1H), 12.45 (s,1H)*** |
| 94. | [benzyloxy-methylphenyl structure] | OH, H(S) | CH$_3$(CH$_2$)$_2$— (S) | —COR$_6$ | (CH$_3$)$_2$CH— | OCH$_3$ | — | −74° | 0.89 (t,3H), 1.29 (d,6H), 1.32 (m,2H), 1.67 (m,2H), 3.80 (s,3H), 4.00 (m,2H), 4.55 (m,1H), 4.92 (d,1H), 5.51 (d,1H), 7.20-7.40 (m,5H), 7.80 (d,1H), 12.50 (s,1H)*** |
| 95. | [phenyl-CH(OH)- structure] | OH, H(R) | CH$_3$(CH$_2$)$_2$— (S) | —COR$_6$ | (CH$_3$)$_2$CH— | OCH$_3$ | — | +38° | 0.90 (t,3H), 1.26 (d,6H), 1.38 (d,6H), 1.69 (m,2H), 3.86 (s,3H), 4.05 (m,1H), 4.08 (m,1H), 4.53 (m,1H), 4.92 (m,1H), 5.33 (m,1H), 5.41 (d,1H), 7.25-7.45 (m,5H), 8.05 (d,1H), 12.50 (s,1H)*** |
| 96. | Ph(CH$_2$)$_2$— | OH, H(S) | CH$_3$(CH$_2$)$_2$— (S) | —COR$_6$ | (CH$_3$)$_2$CH— | OCH$_3$ | — | −8° | 0.86 (t,3H), 1.25 (d,6H), 1.28 (m,2H), 1.68 (m,2H), 1.74 (m,2H), 2.51 (m,2H), 3.78 (s,3H), 3.91 (m,1H), 3.97 (m,1H), 4.43 (m,1H), 5.65 (s,1H), 7.13-7.26 (m,5H), 7.91 (d,1H), 12.47 (s,1H)*** |
| 97. | (CH$_3$)$_3$C— | OH, H(S) | CH$_3$(CH$_2$)$_2$— (S) | —COR$_6$ | (CH$_3$)$_2$CH— | OCH$_3$ | — | — | 0.90 (t,3H), 0.93 (s,9H), 1.30 (d,6H), 1.32 (m,2H), 1.71 (m,2H), 3.58 (d,1H), 3.82 (s,3H), 4.02 (m,1H), 4.52 (m,1H), 5.60 (d,1H), 7.82 (d,1H), 12.45 (s,1H)*** |
| 98. | phenyl | F, H(S) | CH$_3$(CH$_2$)$_2$— (S) | —COR$_6$ | (CH$_3$)$_2$CH— | OCH$_3$ | — | — | 0.87 (t,3H), 1.22 (d,6H), 1.32 (m,2H), 1.70 (m,2H), 3.78 (s,3H), 3.98 (m,1H), 4.52 (m,1H), 5.90 and 6.00 (2s,1H), 7.44 (m,5H), 8.70 (d,1H), 12.55 (s,1H)*** |
| 99. | phenyl | F, H(R) | CH$_3$(CH$_2$)$_2$— (S) | —COR$_6$ | (CH$_3$)$_2$CH— | OCH$_3$ | — | — | 0.90 (t,3H), 1.24 (m,2H), 1.30 (s,6H), 1.77 (m,2H), 3.85 (s,3H), 4.05 (m,1H), 4.48 (m,1H), 5.97 and 6.05 (2s,1H), 7.50 (m,5H), 8.80 (d,1H), 12.62 (s,1H)*** |
| 100. | (CH$_3$)$_2$CH— | OH, H(S) | CH$_3$(CH$_2$)$_2$— (S) | —COR$_6$ | (CH$_3$)$_2$CH— | OCH$_3$ | — | — | 0.77 (d,3H), 0.85 (t,3H), 0.95 (d,3H), 1.26 (d,6H), 1.32 (m,2H), 1.70 (m,2H), 1.95 (m,1H), 3.72 (m,1H), 3.78 (s,3H), 3.98 (m,1H), 4.50 (m,1H), 5.45 (d,1H), 7.80 (d,1H), 12.45 (s,1H)*** |

TABLE-continued (I)

| Cpd. | R₁ | R₂, R'₂ | R₃ | R₄ | R₅ | R₆ | R₇, R₈ | alpha D (C = 1, MeOH) | NMR(DMSO d6 unless specified) * signifies 300 MHz.  signifies 360 MHz - * signifies 500 MHz |
|------|-----|---------|-----|-----|-----|-----|---------|---------|---------|
| 101. | 3,5-difluorophenyl | H, H | CH₃(CH₂)₂— (S) | —COR₆ | phenylpropyl | OCH₂CH₃ | — | — | 0.92 (t,3H), 1.36 (m,2H), 1.71 (m,2H), 2.96 (m,2H), 3.44 (m,2H), 3.61 (5,1H), 3.84 (s,3H), 4.47 (m,1H), 7.12 (d,2H), 7.16 (t,1H), 7.23-7.36 (m,5H), 8.53 (d,1H), 12.55 (s,1H)*** |
| 102. | 3,5-difluorophenyl | =O | CH₃(CH₂)₂— (S) | —COR₆ | cyclopropyl | OCH₃ | — | — | 0.81 (m,2H), 0.97 (t,3H), 1.25 (m,2H), 1.39(m,2H), 1.83 (m,2H), 2.95 (m,1H), 3.86 (s,3H), 4.61 (m,1H), 7.78 (m,3H), 9.40 (d,1H), 12.68 (s,1H)*** |
| 103. | 3,5-difluorophenyl | H, H | CH₃(CH₂)₂— (S) | —COR₆ | methylcyclohexyl | OCH₃ | — | — | 0.92 (t,3H), 1.34-1.43 (m,7H), 1.69-1.84 (m,5H), 2.00 (m,2H), 3.61 (d,2H), 3.69 (m,1H), 3.84 (s,3H), 4.47 (m,1H), 7.06 (d,2H), 7.25 (1,1H), 8.55 (d,1H), 12.55 (s, 1H)*** |
| 104. | 3,5-difluorophenyl | H, H | CH₃(CH₂)₂— (S) | —COR₆ | (CH₃)₃CCH₂— | OCH₃ | — | — | 0.86 (t,3H), 0.91 (s,9H), 1.34 (m,2H), 1.66 (m,2H), 3.12 (m,2H), 3.58 (m,2H), 3.76 (s,3H), 4.40 (m,1H), 7.02 (d,2H), 7.09 (t,1H), 8.49 (d,1H), 12.50 (s, 1H)*** |
| 105. | 3,5-difluorophenyl | =O | CH₃(CH₂)₂— (S) | —COR₆ | (CH₃)₂CH— | NR₇R₈ | CH₃, CH₃ | — | 0.89 (t,3H), 1.23 (d,6H), 1.37 (m,2H), 1.73 (m,2H), 2.88 (s,3H), 2.95 (s,3H), 3.24 (m,1H), 4.58 (m,1H), 7.72 (m,3H), 9.36 (d,1H), 12.36 (s,1H)*** |
| 106. | (CH₃)₃C— | OH, H | CH₃(CH₂)₂— (S) | —COR₆ | (CH₃)₂CH— | NR₇R₈ | CH₃, CH₃ | — | 0.87 (t,3H), 0.90 (s,9H), 1.25 (d,6H), 1.33 (m,2H), 1.68 (m,2H), 2.89 (s,3H), 2.97 (s,3H), 3.57 (s,1H), 4.54 (m,1H), 5.56 (s,1H), 7.84 (d,1H), 12.15 (s,1H)*** |
| 107. | 3-chlorophenyl | OH, H(S) | CH₃(CH₂)₂— (S) | —COR₆ | (CH₃)₂CH— | OCH₃ | — | — | 0.87 (t,3H), 1.20 (m,2H), 1.22 (d,6H), 1.70 (m,2H), 3.80 (s,3H), 4.00 (m,1H), 4.43 (m,1H), 5.02 (s,1H), 6.44 (s,1H), 7.30 (m,3H), 7.45 (s,1H), 8.20 (d,1H), 12.45 (s,1H)*** |
| 108. | (CH₃CH₂)₂CH— | OH, H(S) | CH₃(CH₂)₂— (S) | —COR₆ | (CH₃)₂CH— | OCH₃ | — | — | 0.86 (t,3H), 0.93 (m,6H), 1.24 (m,2H), 1.32 (d,6H), 1.38 (m,4H), 1.55 (m,1H), 1.72 (m,2H), 3.78 (s,3H), 3.98 (m,1H), 4.05 (m,1H), 4.55 (m,1H), 5.55 (d,1H), 7.92 (d,1H), 12.50 (s,1H)*** |

TABLE-continued (I)

| Cpd. | R₁ | R₂, R'₂ | R₃ | R₄ | R₅ | R₆ | R₇, R₈ | alpha D (C = 1, MeOH) | NMR(DMSO d6 unless specified) * signifies 300 MHz.  signifies 360 MHz - * signifies 500 MHz |
|---|---|---|---|---|---|---|---|---|---|
| 109. | (CH₃CH₂)₂CH— | OH, H(R) | CH₃(CH₂)₂ (S) | —COR₆ | (CH₃)₂CH— | OCH₃ | — | — | 0.80 (t,3H), 0.90 (m,6H), 1.20 (m,2H), 1.30 (d,6H), 1.34 (m,4H), 1.55 (m,1H), 1.74 (m,2H), 3.86 (s,3H), 4.00 (m,2H), 4.53 (m,1H), 5.42 (d,1H), 8.00 (d,1H), 12.54 (s,1H)*** |
| 110. | 3,5-difluorophenyl | OH, H | CH₃(CH₂)₂ (S) | —COR₆ | (CH₃)₂CH— | OCH₃ | — | — | 0.82 (m,3H), 1.10 (m,2H), 1.27 (m,6H), 1.61 (m,2H), 2.83 and 2.95 (2m,1H), 3.77 (s,3H), 3.96 (m,1H), 4.21 (m,1H), 4.43 (m,1H), 5.68 and 5.81 (2d,1H), 6.93-7.01 (M,3H), 7.84 and 7.97 (2d,1H), 12.46 (s,1H)*** |
| 111. | 3,5-difluorophenyl | H, H | CH₃(CH₂)₂ (S) | —COR₆ | benzyl | OCH₃ | — | — | 0.87 (t,3H), 1.32 (m,2H), 1.61 (m,2H), 3.55 (m,2H), 3.83 (s,3H), 4.39 (m,1H), 4.61 (s,2H), 6.98 (d,2H), 7.10 (t,1H), 7.30 (m,5H), 8.49 (d,1H), 12.55 (s,1H)*** |
| 112. | 3,5-difluorophenyl | OH, H(S) | CH₃(CH₂)₂ (S) | —COR₆ | benzyl | OCH₃ | — | — | 0.81 (t,3H), 1.22 (m,2H), 1.68 (m,2H), 3.83 (s,3H), 4.40 (m,1H), 4.44 (s,2H), 5.06 (s, 1H), 6.56 (s,1H), 7.15-7.24 (m,3H), 7.32 (m,5H), 8.24 (d,1H), 12.52 (s,1H)*** |
| 113. | 3,5-difluorophenyl | OH, H(R) | CH₃(CH₂)₂ (S) | —COR₆ | benzyl | OCH₃ | — | — | 0.83 (t,3H), 1,24 (m,2H), 1.69 (m,2H), 3.82 (s,3H), 4.37 (m,1H), 4.48 (s,2H), 5.07 (s,1H), 6.55 (s,1H), 7.13 (m,3H), 7.33 (m,5H), 8.26 (d,1H), 12.59 (s,1H)*** |
| 114. | 1-phenylethyl | OH, H | CH₃(CH₂)₂ (S) | —COR₆ | (CH₃)₂CH— | OCH₃ | — | — | 0.70-0.80 (m,3H), 1.12-1.20 (m,3H), 1.20-1.35 (m,2H), 1.30 (m,6H), 1.60 (m,2H), 3.15 (m,1H), 3.80 (s,3H), 4.05 (m,2H), 4.40 (m,1H), 5.43, 5.55 and 5.80 (3d,1H), 6.95-7.30 (m,5H), 7.60 and 7.95 (2d,1H), 12.30.1 2.50 (m,1H)*** |
| 115. | 3-methylthiophene | H, H | CH₃(CH₂)₂ (S) | —COR₆ | (CH₃)₂CH— | OCH₃ | — | — | 0.88 (t,3H), 1.27 (d,6H), 1.35 (m,2H), 1.67 (m,2H), 3.50 (m,2H), 3.80 (s,3H), 4.00 (m,1H), 4.38 (m,1H), 7.00 (d,1H), 7.25 (d,1H), 7.50 (4,1H), 8.35 (d,1H), 12.50 (s,1H)*** |

| Cpd. | R₁ | R₂, R'₂ | R₃ | R₄ | R₅ | R₆ | R₇, R₈ | alpha D (C = 1, MeOH) | NMR(DMSO d6 unless specified) * signifies 300 MHz . ** signifies 360 MHz - *** signifies 500 MHz |
|---|---|---|---|---|---|---|---|---|---|
| 116. | 3,5-difluorophenyl | OH, H(S) | CH₃(CH₂)₂— (S) | —COR₆ | phenyl | OCH₃ | — | — | 0.84 (t,3H), 1.19-1.31 (m,2H), 1.74 (m,2H), 3.69 (s,3H), 4.50 (m,1H), 5.09 (m,1H), 6.58 (s,1H), 7.50 (broad s,3H), 7.45 and 7.51 (2s,5H), 8.31 (d,1H), 12.75 (s,1H)*** |
| 117. | 3,5-difluorophenyl | OH, H(R) | CH₃(CH₂)₂— (S) | —COR₆ | phenyl | OCH₃ | — | — | 0.86 (t,3H), 1.26-1.36 (m,2H), 1.75 (m,2H), 3.69 (s,3H), 4.48 (m,1H), 5.11 (s,1H), 6.59 (s,1H), 7.14 (broad s,3H), 7.34 and 7.49 (2s,5H), 8.35 (d,1H), 12.84 (s,1H)*** |
| 118. | 3,5-difluorophenyl | H, H | CH₃(CH₂)₂— (S) | —COR₆ | (CH₃)₂CH— | OCH₂CH₃ | — | — | 0.87 (t,3H), 1.32 (d,6H), 1.35 (m,2H), 1.61 (m,2H), 3.54 (m,2H), 3.96 (m,1H), 4.24 (m,2H), 4.37 (m,1H), 6.96 (d,2H), 7.07 (t,1H), 8.46 (d,1H), 12.50 (s,1H)*** |
| 119. | 3,5-difluorophenyl | OH, H(S) | CH₃(CH₂)₂— (S) | —COR₆ | (CH₃)₂CH— | OCH₂ | — | — | 0.81 (t,3H), 0.90 (s,9H), 1.21 (m,2H), 1.69 (m,2H), 3.08 (m,2H), 3.77 (s,3H), 4.44 (m,1H), 5.07 (s,1H), 7.17 (m,3H), 8.28 (d,1H)*** |
| 120. | 3,5-difluorophenyl | OH, H(R) | CH₃(CH₂)₂— (S) | —COR₆ | (CH₃)₂CH— | OCH₂ | — | — | 0.87 (t,3H), 0.97 (s,9H), 1.24 (m,2H), 1.72 (m,2H), 3.12 (m,2H), 3.80 (s,3H), 4.41 (m,1H), 5.10 (d,1H), 6.45 (d,1H), 7.10 (m,3H), 8.30 (d,1H), 12.50 (s,1H)*** |
| 121. | 3-chlorophenyl | ⟨ketone group⟩ | CH₃(CH₂)₂— (S) | —COR₆ | (CH₃)₂CH— | OCH₃ | — | — | 0.91 (t,3H), 1.32 (d,6H), 1.37 (m,2H), 1.78 (m,2H), 3.79 (s,3H), 4.02 (m,1H), 4.56 (m,1H), 7.63 (t,1H), 7.80 (d,1H), 7.94 (d,1H), 7.99 (s,1H), 9.33 (d,1H), 12.66 (s,1H)*** |
| 122. | 2-benzyloxyphenyl | OH, H | CH₃(CH₂)₂— (S) | —COR₆ | (CH₃)₂CH— | OCH₃ | — | — | 0.85 (m,3H), 1.26 (d,6H), 1.28 (d,6H), 1.69 (m,2H), 3.78 (s,3H), 3.98 (m,1H), 4.47 (m,1H), 5.22 (s,2H), 5.33 (2d,1H), 6.07 and 6.11 (2d,1H), 6.90-7.50 (m,8H) 8.00 (m,1H), 12.48 (s,1H)*** |
| 123. | ⟨thiophene⟩ | H, H | CH₃(CH₂)₂— (S) | —COR₆ | (CH₃)₂CH— | OCH₃ | — | — | 0.87 (t,3H), 1.28 (d,6H), 1.36 (m,2H), 1.67 (m,2H), 3.70 (m,2H), 3.78 (s,3H), 3.98 (m,1H), 4.36 (m,1H), 6.90 and 6.92 (d+t,2H), 7.33 (d,1H), 8.41 (d,1H), 12.58 (s,1H)*** |
| 124. | 2,3-difluorophenyl | OH, H(S) | CH₃(CH₂)₂— (S) | —COR₆ | (CH₃)₂CH— | OCH₃ | — | — | 0.85 (t,3H), 1.27 (d,6H), 1.31 (m,2H), 1.72 (m,2H), 3.79 (s,3H), 3.97 (m,1H), 4.49 (m,1H), 5.25 (s,1H), 6.62 (broad s 1H), 7.22 (m,2H), 7.36 (m,1H), 8.21 (d,1H), 12.53 (s,1H)*** |

TABLE-continued (I)

| Cpd. | R₁ | R₂, R'₂ | R₃ | R₄ | R₅ | R₆ | R₇, R₈ | alpha D (C = 1, MeOH) | NMR(DMSO d6 unless specified) * signifies 300 MHz.  signifies 360 MHz - * signifies 500 MHz |
|---|---|---|---|---|---|---|---|---|---|
| 125. | 2,3-difluorophenyl | OH, H(R) | CH₃(CH₂)₂— (S) | —COR₆ | (CH₃)₂CH— | OCH₃ | — | — | 0.89 (t,3H), 1.29 (d,6H), 1.33 (m,2H), 1.71 (m,2H), 3.80 (s,3H), 3.96 (m,1H), 4.47 (m,1H), 5.30 (d,1H), 6.58 (d,1H), 7.19 (m,2H), 7.26 (m,1H), 8.26 (d,1H), 12.57 (s,1H)*** |
| 126. | 2,5-difluorophenyl | OH, H(S) | CH₃(CH₂)₂— (S) | —COR₆ | (CH₃)₂CH— | OCH₃ | — | — | 0.86 (t,3H), 1.28 (d,6H), 1.31 (m,2H), 1.72 (m,2H), 3.79 (s,3H), 3.98 (m,1H), 4.48 (m,1H), 5.21 (s,1H), 6.59 (broad s 1H), 7.21 (m,3H), 8.22 (d,1H), 12.51 (s,1H)*** |
| 127. | 2,5-difluorophenyl | OH, H(R) | CH₃(CH₂)₂— (S) | —COR₆ | (CH₃)₂CH— | OCH₃ | — | — | 0.90 (t,3H), 1.34 (d,6H), 1.39 (m,2H), 1.77 (m,2H), 3.83 (s,3H), 4.06 (m,1H), 4.50 (m,1H), 5.36 (d,1H), 6.56 (d,1H), 7.25 (m,3H), 8.32 (d,1H), 12.58 (s,1H)*** |
| 128. | 2-hydroxyphenyl | OH, H | CH₃(CH₂)₂— (S) | —COR₆ | (CH₃)₂CH— | OCH₃ | — | — | 0.91 (m,3H), 1.28 (m,2H), 1.30 (d,6H), 1.80 (m,2H), 3.85 (s,3H), 4.07 (m,1H), 4.53 (m,1H), 5.31 and 5.35 (2s,1H), 6.87 (m,2H), 7.13 (m,1H), 7.27 (m,1H), 8.17 (m,1H), 9.66 (broad s 1H), 12.49 (s,1H)*** |
| 129. | CF₃—CH(CF₃)— | OH, H(R) | CH₃(CH₂)₂— (S) | —COR₆ | (CH₃)₂CH— | OCH₃ | — | — | 0.92 (t,3H), 1.27 (m,2H), 1.32 (d,6H), 1.77 (m,2H), 3.84 (s,3H), 4.05 (m,1H), 4.34 (m,1H), 4.59 (m,1H), 4.64 (m,1H), 7.08 (d,1H), 8.25 (d,1H), 12.50 (s,1H)*** |
| 130. | CF₃—CH(CF₃)— | OH, H(R) | CH₃(CH₂)₂— (S) | —COR₆ | (CH₃)₂CH— | OCH₃ | — | — | 0.94 (t,3H), 1.37 (D,6H), 1.42 (m,2H), 1.78 (m,2H), 3.85 (s,3H), 4.06 (m,1H), 4.28 (m,1H), 4.56 (m,1H), 4.66 (m,1H), 7.10 (d,1H), 8.40 (d,1H), 12.58 (s,1H)*** |
| 131. | 3,5-difluorophenyl | H, H | CH₃(CH₂)₂— (S) | —COR₆ | (CH₃)₂CH— | NR7R8 | —(CH₂)₂-pyridin-2-yl | — | 0.87 (t,3H), 1.28 (d,6H), 1.29 (m,2H), 1.63 (m,2H), 2.98 (m,2H), 3.52 (m,2H), 3.62 (m,2H), 4.20 (m,1H), 4.46 (m,1H), 6.98 (d,2H), 7.10 (t,1H), 7.28 (m,2H), 7.70 (t,1H), 7.90 (m,2H), 8.53 (m,2H), 12.20 (s,1H)*** |
| 132. | cyclopropyl | OH, H(S) | CH₃(CH₂)₂— (S) | —COR₆ | (CH₃)₂CH— | OCH₃ | — | — | 0.33 (m,2H), 0.37 (m,2H), 0.90 (t,3H), 1.09 (m,1H), 1.30 (d,6H), 1.34 (m,2H), 1.71 (m,2H), 3.66 (m,1H), 3.83 (s,3H), 4.03 (m,1H), 4.59 (m,1H), 5.55 (d,1H), 7.88 (d,1H), 12.52 (s,1H)*** |

TABLE-continued

(I)

| Cpd. | R₁ | R₂, R'₂ | R₃ | R₄ | R₅ | R₆ | R₇, R₈ | alpha D (C = 1, MeOH) | NMR(DMSO d6 unless specified) * signifies 300 MHz.  signifies 360 MHz - * signifies 500 MHz |
|---|---|---|---|---|---|---|---|---|---|
| 133. | 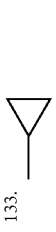 | OH, H | CH₃(CH₂)₂— (S) | —COR₆ | (CH₃)₂CH— | OCH₃ | — | — | 0.30 (m,2H), 0.38 (m,2H), 0.86 (t,3H), 1.03 (m,1H), 1.27 (d,6H), 1.30 (m,2H), 1.67 (m,2H), 3.55 (m,1H), 3.78 (s,3H), 3.99 (m,1H), 4.50 (m,1H), 5.37 and 5.50 (2d,1H), 7.76 and 7.84 (2d,1H), 12.50 (s,1H)*** |
| 134. | 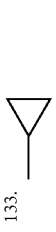 | H, H | CH₃(CH₂)₂— (S) | —COR₆ | (CH₃)₂CH— | OCH₃ | — | — | 0.87 (t,3H), 1.28 (d,6H), 1.36 (m,2H), 1.67 (m,2H), 3.75 (m,2H), 3.77 (s,3H), 3.98 (m,1H), 4.42 (m,1H), 7.33 (m,2H), 7.50 (s,1H), 7.83 (d,1H), 7.94 (d,1H), 8.52 (d,1H), 12.58 (s,1H)*** |
| 135. | 3-chlorophenyl | OH, H | CH₃(CH₂)₂— (S) | —COR₆ | (CH₃)₂CH— | OCH₃ | — | — | 0.87 (m,3H), 1.25 (m,2H), 1.28 (s,6H), 1.75 (m,2H), 3.83 (s,3H), 4.01 (m,1H), 4.48 (m,1H), 4.94 (2d,1H), 6.14 and 6.29 (2d,1H), 6.67 (m,1H), 6.87 (m,2H), 7.14 (m,1H), 8.11 (m,1H), 8.41 (2s,1H), 12.52 (d,1H)*** |
| 136. | 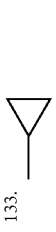 | H, H | CH₃(CH₂)₂— (S) | —COR₆ | (CH₃)₂CH— | OCH₃ | — | — | 0.87 (m,3H), 1.24 (s,6H), 1.26 (m,2H), 1.73 (m,2H), 3.80 (s,3H), 3.98 (m,1H), 4.45 (m,1H), 5.08 (m,1H), 6.17 and 6.27 (2d, 1H), 7.11 (d,1H), 7.41-7.48 (m,2H), 8.14 (m,1H), 12.50 (d,1H)*** |
| 137. |  | H, H | CH₃(CH₂)₂— (S) | —COR₆ | (CH₃)₂CH— | OCH₃ | — | — | 0.86 (t,3H), 1.28 (d,6H), 1.29 (m,2H), 1.61 (m,2H), 2.47 (m,2H), 2.81 (m,2H), 3.88 (s,3H), 4.00 (m,1H), 4.46 (m,1H), 6.98 (s,1H), 7.23 (s,1H), 7.43 (s,1H), 8.16 (d,1H), 12.44 (s,1H)*** |
| 138. | 3,5-difluorophenyl | H, H | CH₃(CH₂)₂— (S) | —COR₆ | (CH₃)₂CH— | NR₇R₈ | —(CH₂)₂—C₆H₅, H | — | 0.92 (t,3H), 1.31 (d,6H), 1.40 (m,2H), 1.71 (m,2H) 2.86 (m,2H), 3.54 (m,2H), 3.60 (m,2H), 4.24 (m,1H), 4.50 (m,1H), 7.13 (d,2H), 7.18 (t,1H), 7.25-7.36 (m,5H), 7.80 (d,1H), 8.56 (d,1H), 12.25 (s,1H)*** |

TABLE-continued (I)

| Cpd. | R₁ | R₂, R'₂ | R₃ | R₄ | R₅ | R₆ | R₇, R₈ | alpha D (C = 1, MeOH) | NMR(DMSO d6 unless specified) * signifies 300 MHz.  signifies 360 MHz - * signifies 500 MHz |
|---|---|---|---|---|---|---|---|---|---|
| 139. | 4-methylpyridinyl | OH, H | CH₃(CH₂)₂— (S) | —COR₆ | (CH₃)₂CH— | OCH₃ | — | — | 0.84 (t,1H), 1.20 (m,2H), 1.22 (d,6H), 1.70 (m,2H), 3.80 (s,3H), 3.99 (m,1H), 4.45 (m,1H), 5.07 (s,1H), 6.49 (d,1H), 7.37 (d,1H), 7.80 (d,1H), 8.27 (d,1H), 8.48 (d,1H), 8.61 (s,1H), 12.42 (broad s,1H)*** |
| 140. | 4-methylpyridinyl | =O | CH₃(CH₂)₂— (S) | —COR₆ | (CH₃)₂CH— | OCH₃ | — | — | 0.95 (t,3H), 1.35 (d,6H), 1.42 (m,2H), 1.85 (m,2H), 3.82 (s,3H), 4.05 (m,1H), 4.62 (m,1H), 7.70 (d,1H), 8.40 (d,1H), 8.90 (d,1H), 9.19 (s,1H), 9.35 (d,1H), 12.65 (s,1H)*** |
| 141. | 2-furyl | =O | CH₃(CH₂)₂— (S) | —COR₆ | (CH₃)₂CH— | OCH₃ | — | — | 0.95 (t,3H), 1.38 (d,6H), 1.41 (m,2H), 1.85 (m,2H), 3.84 (s,1H), 4.04 (m,1H), 4.58 (m,1H), 6.86 (s,1H), 7.86 (s,1H), 8.23 (s,1H), 9.20 (d,1H), 12.60 (s,1H) |
| 142. | 3,5-difluorophenyl | H, H | CH₃(CH₂)₂— (S) | —COR₆ | 6-methylnaphthalenyl | OCH₃ | — | — | 0.88 (t,3H), 1.35 (m,2H), 1.69 (m,2H), 3.61 (m,2H), 3.68 (s,3H), 4.46 (m,1H), 7.08 (d,2H), 7.09(t,1H), 7.60 (m,3H), 7.96 (m,3H), 7.99 (s,1H), 8.52 (s,1H), 12.78 (s,1H)*** |
| 143. | 3,5-difluorophenyl | H, H | CH₃(CH₂)₂— (S) | —COR₆ | 3-(benzyloxy)phenyl | OCH₃ | — | — | 0.89 (t,3H), 1.30 (m,2H), 1.68 (m,2H), 3.56 (m,2H), 3.67 (s,3H), 4.43 (m,1H), 5.13 (s,2H), 6.98 (d,2H), 7.08-7.47 (m,10H), 8.58 (d,1H), 12.65 (s,1H)*** |
| 144. | 3,5-difluorophenyl | H, H | CH₃ | —(CH₂)₃CH₃ | —COR₆ | OCH₃ | — | — | 0.88 (t,3H), 1.32 (d,3H), 1.66 (m,2H), 2.95 (m,2H), 3.54 (s,2H), 3.76 (s,3H), 4.47 (m,2H), 6.97 and 7.10 (2m,3H), 8.63 (d,1H), 12.66 (s,1H)*** |
| 145. | 3,5-difluorophenyl | H, H | CH₃(CH₂)₂— (S) | cyclohexylethyl | —COR₆ | OCH₃ | — | — | 0.87 (t,3H), 0.98 (m,2H), 1.13 (m,3H), 1.27 and 1.36 (2m,2H), 1.59-1.70 (m,8H), 2.83 and 2.93 (2m,2H), 3.28 (s,2H), 3.78 (s,3H), 4.44 (m,1H), 6.96 and 7.09 (m,3H), 8.54 (d,1H), 12.66 (s,1H)*** |

TABLE-continued (I)

| Cpd. | R₁ | R₂, R'₂ | R₃ | R₄ | R₅ | R₆ | R₇, R₈ | alpha D (C = 1, MeOH) | NMR(DMSO d6 unless specified) * signifies 300 MHz.  signifies 360 MHz - * signifies 500 MHz |
|---|---|---|---|---|---|---|---|---|---|
| 146. | 3,5-difluorophenyl | H, H | CH₃(CH₂)₂— (S) | —(CH₃)₂CH₃ | —COR₆ | OCH₃ | — | — | 0.87 (t,3H), 1.27 (d,6H), 1.35 (m,2H), 1.64 (m,2H), 3.54 (s,2H), 3.77 (s,3H), 3.90 (m,1H), 4.45 (m,1H), 6.96-7.09 (m,3H), 8.53 (d,1H), 12.69 (s,1H)*** |
| 147. | 3,5-difluorophenyl | OH, H(S) | CH₃(S) | —(CH₃)₂CH₃ | —COR₆ | OCH₃ | — | — | 1.18 (d,6H), 1.32 (d,3H), 3.77 (s,3H), 3.91 (m,1H), 4.48 (m,1H), 5.05 (s,1H), 6.53 (s,1H), 7.12 (m,3H), 8.37 (d,1H), 12.61 (s,1H)*** |
| 148. | 3,5-difluorophenyl | H, H | CH₃(S) | —CH(CH₃)₂ | —COR₆ | OCH₃ | — | — | 1.15 (d,6H), 1.32 (d,3H), 3.53 (s,2H), 3.77 (s,3H), 4.04 (m,1H), 4.47 (m,1H), 6.97-7.09 (m,3H), 8.59 (d,1H), 12.66 (s,1H)*** |
| 149. | 3,5-difluorophenyl | OH, H(S) | CH₃(S) | —CH(CH₃)₂ | —COR₆ | OCH₃ | — | — | 1.17 (d,6H), 1.35 (d,3H), 3.77 (s,3H), 3.91 (m,1H), 4.49 (m,1H), 5.04 (s,1H), 6.47 (s,1H), 7.12 (m,3H), 8.37 (d,1H), 12.62 (s,1H)*** |
| 150. | 3,5-difluorophenyl | OH, H(S) | CH₃(CH₂)₂— (S) | —CH(CH₃)₂ | —COR₆ | OCH₃ | — | −73° | 0.81 (t,3H), 1.18 (d,6H), 1.22 (m,2H), 1.71 (m,2H), 3.77 (s,3H), 3.90 (m,1H), 4.50 (m,1H), 5.06 (s,1H), 6.54 (s,1H), 7.12 (m,3H), 8.30 (d,1H), 12.66 (s,1H)*** |
| 151. | 3,5-difluorophenyl | OH, H(R) | CH₃(CH₂)₂— (S) | —CH(CH₃)₂ | —COR₆ | OCH₃ | — | −104° | 0.83 (t,3H), 1.19 (d,6H), 1.22 (m,2H), 1.70 (m,2H), 3.77 (s,3H), 3.91 (m,1H), 4.48 (m,1H), 5.07 (s,1H), 6.42 (s,1H), 7.12 (m,3H), 8.34 (d,1H), 12.67 (s,1H)*** |
| 152. | 3,5-difluorophenyl | H, H | CH₃(CH₂)₂— (S) | phènyle | —COR₆ | OCH₃ | — | −88° | 0.86 (t,3H), 1.19 (t,3H), 1.29 (m,2H), 1.67 (m,2H), 3.57 (s,2H), 4.18 (m,2H), 4.47 (m,1H), 6.98 and 7.10 (m,3H), 7.42 and 7.68 (2s,5H), 8.55(d,1H), 12.81 (s,1H)*** |
| 153. | 3,5-difluorophenyl | H, H | CH₃(CH₂)₂— (S) | —CH(CH₃)₂ | —COR₆ | OCH₂CH₃ | — | −120° | 0.87(t,3H), 1.18 (d,6H), 1.27 (t,3H), 1.30 (m,2H), 1.65 (m,2H), 3.55 (s,2H), 3.90 (m,1H), 4.25 (m,2H), 4.43 (m,1H), 6.80-7.13 (m,3H), 8.53 (d,1H), 12.66 (s,1H)*** |
| 154. | 3,5-difluorophenyl | OH, H(S) | CH₃(CH₂)₂— (S) | —CH(CH₃)₂ | —COR₆ | OCH₃ | — | — | 0.80 (t,3H), 0.90(t,3H), 1.22 (m,2H), 1.68 and 1.72 (2m,4H), 2.98 (m,2H), 3.78 (s,3H), 4.52 (m,1H), 5.06 (s,1H), 6.55 (s,1H), 7.17 (m,3H), 8.31 (d,1H), 12.68 (s,1H)*** |
| 155. | 3,5-difluorophenyl | OH, H(S) | CH₃(CH₂)₂— (S) | —(CH₂)₂CH₃ | —COR₆ | OCH₃ | — | — | 0.80 (t,3H), 0.90(3,3H), 1.22 (m,2H), 1.66 and 1.73 (2m,4H), 2.98 (m,2H), 3.78 (s,3H), 4.49 (m,1H), 5.09 (s,1H), 6.43 (s,1H), 7.14 (m,5H), 8.38 (d,1H), 12.68 (s,1H)*** |
| 156. | 3,5-difluorophenyl | H, H | CH₃(CH₂)₂— (S) | —(CH₂)₂CH₃ | —COR₆ | OCH₃ | — | −85° | 0.89 (2t,6H), 1.37 (m,2H), 1.63 (m,4H), 2.95 (m,2H), 3.55 (s,2H), 3.76 (s,3H), 4.43 (m,1H), 6.80-7.12 (m,3H), 8.55 (d,1H), 12.68 (s 1H)*** |

TABLE-continued

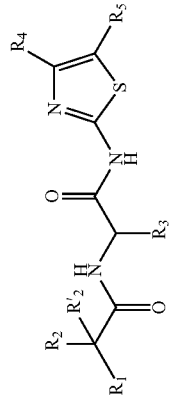

(I)

| Cpd. | R₁ | R₂, R'₂ | R₃ | R₄ | R₅ | R₆ | R₇, R₈ | alpha D (C = 1, MeOH) | NMR(DMSO d6 unless specified) * signifies 300 MHz.  signifies 360 MHz - * signifies 500 MHz |
|---|---|---|---|---|---|---|---|---|---|
| 157. | 3,5-difluorophenyl | H, H | CH₃(CH₂)₂— (S) | —CH₂CH₃ | —COR₆ | OCH₃ | — | −112° | 0.88(t,3H), 1.30(t,3H), 1.37 (m,2H), 1.63 (m,2H), 2.98 (m,1H), 3.56 (s,2H), 3.78 (s,3H), 4.50 (m,1H), 6.81-7.25 (m,3H), 8.56 (d,1H), 12.71 (s,1H)*** |
| 158. | 3,5-difluorophenyl | H, H | CH₃(CH₂)₂— (S) | —CH₂CH(CH₃)₂ | —COR₆ | OCH₃ | — | −99° | 0.89 (t+d,12H), 1.29 (m,2H), 1.66 (m,2H), 2.05 (m,1H), 2.86 (m,2H), 3.56 (s,2H), 3.78 (s,3H), 4.46 (m,1H), 7.06-7.15 (m,3H), 8.64 (d,1H), 12.68 (s,1H)*** |
| 159. | 3,5-difluorophenyl | H, H | CH₃(CH₂)₂— (S) | —CH₃ | —COR₆ | OCH₃ | — | −126° | 0.88(t,3H), 1.29 (m,2H), 1.65 (m,2H), 2.55 (s,3H), 3.56 (s,2H), 3.78 (s,3H), 4.45 (m,1H), 6.99-7.14 (m,5H), 8.55 (d,1H), 12.68 (s,1H)*** |
| 160. | 3,5-difluorophenyl | OH, H(S) | CH₃(CH₂)₂— (S) | —CH₂CH₃ | —COR₆ | OCH₃ | — | — | 0.82 (t,3H), 1.20 (d,6H), 1.26 (m,2H), 1.72 (m,2H), 2.99 (m,2H), 3.78 (s,3H), 4.49 (m,1H), 5.10 (s,1H), 6.43 (s,1H), 7.16 (m,3H), 8.36 (d,1H), 12.70 (s,1H)*** |
| 161. | 3,5-difluorophenyl | OH, H(R) | CH₃(CH₂)₂— (S) | —CH₂CH₃ | —COR₆ | OCH₃ | — | — | 0.89(t,3H), 1.24 (d,6H), 1.28 (m,2H), 1.77 (m,2H), 3.04 (m,2H), 3.83 (s,3H), 4.52 (m,1H), 5.15 (s,1H), 6.48 (s,1H), 7.18 (m,3H), 8.40 (d,1H), 12.65 (s,1H)*** |
| 162. | 3,5-difluorophenyl | =O | CH₃(CH₂)₂— (S) | —CH₂CH₃ | —COR₆ | OCH₃ | — | — | 0.92(t,3H), 1.20 (t,3H), 1.38 (m,2H), 1.78 (m,2H), 3.00 (m,2H), 3.80 (s,3H), 4.64 (m,1H), 7.72 (m,3H), 9.45 (d,1H), 12.95 (s,1H)*** |
| 163. | (CH₃)₃C— | OH, H(S) | CH₃(CH₂)₂— (S) | —CH₂CH₃ | —COR₆ | OCH₃ | — | — | 0.87 (t,3H), 0.91 (s,9H), 1.21 (t,3H), 1.27 (m,2H), 1.69 (m,2H), 3.01 (m,2H), 3.57 (d,1H), 3.78 (s,3H), 4.57 (m,1H), 5.56 (d,1H), 7.85 (d,1H), 12.63 (s,1H)*** |
| 164. | (CH₃)₃C— | =O | CH₃(CH₂)₂— (S) | —CH₂CH₃ | —COR₆ | OCH₃ | — | — | 0.95 (t,3H), 1.34 (s,9H), 1.35 (t,3H), 1.40 (m,2H), 1.75 (m,2H), 3.04 (m,2H), 3.98 (s,3H), 4.62 (m,1H), 9.03 (d,1H), 12.85 (s,1H)*** |
| 165. | 3,5-difluorophenyl | OH, H(S) | CH₃(CH₂)₂— (S) | —CH₃ | —COR₆ | OCH₃ | — | — | 0.82 (t,3H), 1.26 (m,2H), 1.69 (m,2H), 2.63 (s,3H), 3.77 (s,3H), 4.50 (m,1H), 5.07 (d,1H), 6.55 (d,1H), 7.16 (m,3H), 8.31 (d,1H), 12.65 (s,1H)*** |
| 166. | 3,5-difluorophenyl | H, H | CH₃(CH₂)₂— (S) | —CH₂C(CH₃)₃ | —COR₆ | OCH₃ | — | — | 0.87 (t,3H), 0.94 (s,9H), 1.31 (m,2H), 1.66 (m,2H), 2.89-3.05 (m,2H), 3.59 (s,2H), 3.77 (s,3H), 4.48 (m,1H), 6.98 (d,2H), 7.10 (t,1H), 8.54 (d,1H), 12.65 (s,1H)*** |

TABLE-continued (I)

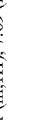

| Cpd. | R$_1$ | R$_2$, R'$_2$ | R$_3$ | R$_4$ | R$_5$ | R$_6$ | R$_7$, R$_8$ | alpha D (C = 1, MeOH) | NMR(DMSO d6 unless specified) * signifies 300 MHz .  signifies 360 MHz - * signifies 500 MHz |
|---|---|---|---|---|---|---|---|---|---|
| 167. | 3,5-difluorophenyl | =O | CH$_3$(CH$_2$)$_2$— (S) | —CH$_3$ | —COR$_6$ | OCH$_3$ | — | — | 0.90 (t,3H), 1.38 (m,2H), 1.75 (m,2H), 2.63 (s,3H), 3.78 (s,3H), 4.61 (m,1H), 7.69 (m,3H), 9.43 (d,1H)*** |
| 168. | 3,5-difluorophenyl | OH, H(S) | CH$_3$(CH$_2$)$_2$— (S) | —CH$_2$C(CH$_3$)$_3$ | —COR$_6$ | OCH$_3$ | — | — | 0.81 (t,3H), 0.92 (s,9H), 1.20 (m,2H), 1.70 (m,2H), 2.90- 2.98 (m,2H), 3.77 (s,3H), 4.50 (m,1H), 5.08 (d,1H), 6.52 (d,1H), 7.12 (m,3H), 8.30 (d,1H), 12.60 (s,1H)*** |
| 169. | 3,5-difluorophenyl | OH, H(R) | CH$_3$(CH$_2$)$_2$— (S) | —CH$_2$C(CH$_3$)$_3$ | —COR$_6$ | OCH$_3$ | — | — | 0.84 (t,3H), 0.93 (s,9H), 1.26 (m,2H), 1.71 (m,2H), 2.90- 3.00 (m,2H), 3.80 (s,3H), 4.47 (m,1H), 5.08 (d,1H), 6.43 (d,1H), 7.17 (m,3H), 8.35 (d,1H), 12.60 (s,1H)*** |
| 170. | 3,5-difluorophenyl | H, H | CH$_3$(CH$_2$)$_2$— (S) | 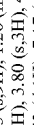 | —COR$_6$ | OCH$_2$CH$_3$ | — | — | 0.89 (t,3H), 1.27 (m,2H), 1.29 (m,2H), 1.66 (m,2H), 1.97 (m,2H), 2.63 (m,2H), 3.00 (m,2H), 3.57 (s,2H), 4.25 (m,2H), 4.45 (m,1H), 6.99 (d,2H), 7.09 (t,1H), 7.19-7.27 (m,5H), 8,55 (d,1H), 12.68 (s,1H)*** |
| 171. | 3,5-difluorophenyl | OH, H(S) | CH$_3$(CH$_2$)$_2$— (S) |  | —COR$_6$ | OCH$_3$ | — | — | 0.82 (t,3H), 1.18 (m,2H), 1.22 (t,3H), 1.67 (m,2H), 1.90 (m,2H), 2.61 (m,2H), 3.00 (m,2H), 4.23 (m,2H), 4.47 (m,1H), 5.06 (d,1H), 6.54 (d,1H), 7.10-7.32 (m,8H), 8.28 (d,1H), 12.60 (s,1H)*** |
| 172. | 3,5-difluorophenyl | OH, H(R) | CH$_3$(CH$_2$)$_2$— (S) |  | —COR$_6$ | OCH$_2$CH$_3$ | — | — | 0.82(t,3H), 1.24 (t,3H), 1.29 (m,2H), 1.68 (m,2H), 1.91 (m,2H), 2.61 (m,2H), 2.99 (m,2H), 4.21 (m,2H), 4.46 (m,1H), 5.07 (d,1H), 6.40 (d,1H), 7.07-7.31 (m,8H), 8.32 (d,1H), 12.60 (s,1H)*** |

TABLE-continued (I)

| Cpd. | R₁ | R₂, R'₂ | R₃ | R₄ | R₅ | R₆ | R₇, R₈ | alpha D (C = 1, MeOH) | NMR(DMSO d6 unless specified) * signifies 300 MHz.  signifies 360 MHz - * signifies 500 MHz |
|------|-----|---------|-----|-----|-----|-----|--------|---------------------|---|
| 173. | 3,5-difluorophenyl | H, H | CH₃(CH₂)₂— (S) | —(CH₂)₃-phenyl | —COR₆ | OCH₂CH₃ | — | — | 0.85 (t,3H), 1.26 (t,3H), 1.27 (m,2H), 1.59 (m,8H), 2.56 (m,2H), 2.99 (m,2H), 3.54 (m,2H), 4.23 (m,2H), 4.43 (m,1H), 6.98 (d,2H), 7.09 (t,1H), 7.14-7.30 (m,5H), 8.52 (d,1H), 12.82 (s,1H)*** |
| 174. | 3,5-difluorophenyl | H, H | CH₃(CH₂)₂— (S) | —(CH₂)₄CH(CH₃)₂ | —COR₆ | OCH₂CH₃ | — | — | 0.82 (d,6H), 0.86(t,3H), 1.18 (m,2H), 1.27 (t,3H), 1.28 (m,2H), 1.30 (m,2H), 1.47 (m,2H), 1.63 (m,4H), 2.96 (m,1H), 3.56 (m,2H), 4.24 (m,2H), 4.44 (m,1H), 6.98 (d,2H), 7.14 (t,1H), 8.53 (d,1H), 12.67 (s,1H)*** |
| 175. | 3,5-difluorophenyl | H, H | CH₃(CH₂)₂— (S) | —(CH₂)₂CH(CH₃)₂ | —COR₆ | OCH₃ | — | — | 0.88 (t,3H), 0.91 (d,6H), 1.37 (m,2H), 1.52 (m,4H), 1.63 (m,2H), 3.00 (m,1H), 3.63 (m,2H), 3.78 (s,3H), 4.45 (m,1H), 6.99 (d,2H), 7.10 (t,1H), 8.56 (d,1H), 12.67 (s,1H)*** |
| 176. | 3,5-difluorophenyl | H, H | CH₃(CH₂)₂— (S) | —CH₃ | —COR₆ | NR₇R₈ | CH₃, (CH₂)₂-phenyl | −103° | 0.92 (t,3H), 1.38 (m,2H), 1.65 (m,2H), 2.14 (s,3H), 2.88 (m,2H), 2.97 (s,3H), 3.63 (s,2H), 3.67 (m,2H), 4.51 (m,1H), 7.04 (d,2H), 7.12 (t,1H), 7.24-7.30 (m,5H), 8.55 (d,1H), 12.46 (s,1H)*** |
| 177. | 3,5-difluorophenyl | H, H | CH₃(CH₂)₂— (S) | —CH₃ | —COR₆ | NR₇R₈ | CH₃, (CH₂)₂-phenyl,H | −97° | 0.91 (t,3H), 1.37 (m,2H), 1.67 (m,2H), 2.45 (s,3H), 2.85 (m,2H), 3.45 (m,2H), 3.60 (s,2H), 4.53 (m,1H), 7.03 (d,2H), 7.14 (t,1H), 7.24-7.32 (m,5H), 7.99 (d,1H), 8.55 (d,1H), 12.44 (s,1H)*** |

TABLE-continued (I)

| Cpd. | $R_1$ | $R_2, R'_2$ | $R_3$ | $R_4$ | $R_5$ | $R_6$ | $R_7, R_8$ | alpha D (C = 1, MeOH) | NMR(DMSO d6 unless specified) * signifies 300 MHz.  signifies 360 MHz - * signifies 500 MHz |
|---|---|---|---|---|---|---|---|---|---|
| 178. | 3,5-difluorophenyl | H, H | $CH_3(CH_2)_2-$ (S) | $-CH_3$ | $-COR_6$ | $NR_7R_8$ | H, $CH_3$ | — | 0.91 (t,3H), 1.37 (m,2H), 1.66 (m,2H), 2.50 (s,3H), 2.75 (d,1H), 3.62 (s,2H), 4.48 (m,1H), 7.01 (d,2H), 7.14 (t,1H), 7.91 (d,1H), 8.54 (d,1H), 12.43 (s,1H) |
| 179. | 3,5-difluorophenyl | H, H | $CH_3(CH_2)_2-$ (S) | $-COR_6$ | ![phenoxy-methylphenyl] | $OCH_3$ | — | — | 0.91 (t,3N), 1.35 (m,2H), 1.72 (m,2H), 3.60 (m,2H), 3.85 (s,3H), 4.47 (m,1H), 7.02 (d,2H), 7.09 (t,1H), 7.10-7.47 (m,9H), 8.55 (d, 1H), 12.80 (s,1H)*** |
| 180. | 3,5-difluorophenyl | H, H | $CH_3(CH_2)_2-$ (S) | $-COR_6$ | ![hydroxy-methylphenyl] | $OCH_3$ | — | — | 0.93 (t,3H), 1.32 (m,2H), 1.70 (m,2H), 3.66 (m,2H), 3.78 (s,3H), 3.50 (m,1H), 6.90-6.95 (m,3H), 7.08 (d,2H), 7.17 (t,1H), 7.29 (t,1H), 8.58 (d,1H), 9.68 (s,1H), 12.77 (s,1H)*** |
| 181. | 3,5-difluorophenyl | H, H | $CH_3(CH_2)_2-$ (S) | $-COR_6$ | ![naphthyl] | $OCH_3$ | — | — | 0.92 (t,3H), 1.36 (m,2H), 1.70 (m,2H), 3.49 (s,3H), 3.61 (m,2H), 4.50 (m,1H), 7.02 (d,2H), 7.10 (t,1H), 7.53-7.62 (m,5H), 8.04 (m,2H), 8.55 (d,1H), 12.87 (s,1H)*** |
| 182. | 3,5-difluorophenyl | H, H | $CH_3(CH_2)_2-$ (S) | $-COR_6$ | ![benzyloxy-methylphenyl] | $OCH_3$ | — | — | 0.93 (m,3H), 1.39 (m,2H), 1.68 (m,2H), 3.57 (m,5H), 4.49 (m,1H), 5.15 (s,2H), 7.06 (d,2H), 7.19 (t, 1H), 7.34 (m,5H), 8.60 (s,1H), 12.67 (s,1H)*** |
| 183. | 3,5-difluorophenyl | H, H | $CH_3(CH_2)_2-$ (S) | $-COR_6$ | ![methoxy-methylphenyl] | $OCH_3$ | — | — | 0.93 (t,3H), 1.39 (m,2H), 1.68 (m,2H), 3.61 (m, 2H), 3.73 (s,3H), 4.82 (s,3H), 4.47 (m,2H), 7.06 (d, 2H), 7.04-7.14 (m,6H), 7.40 (t,1H), 8.56 (s,1H), 12.72 (s,1H)*** |
| 184. | 3,5-difluorophenyl | H, H | $CH_3(CH_2)_2-$ (S) | $-COR_6$ | ![ethoxy-methylphenyl] | $OCH_3$ | — | — | 0.91 (t,3H), 1.34 (m,2H), 1.39 (s,3H), 1.69 (m,2H), 3.57 (m,2H), 3.71 (s,3H), 4.10 (m,2H), 4.47 (m, 1H), 7.07 (m,6H), 7.35 (t,1H), 8.55 (s,1H), 12.78 (s, 1H)*** |

TABLE-continued (I)

| Cpd. | R$_1$ | R$_2$, R'$_2$ | R$_3$ | R$_4$ | R$_5$ | R$_6$ | R$_7$, R$_8$ | alpha D (C = 1, MeOH) | NMR(DMSO d6 unless specified) * signifies 300 MHz.  signifies 360 MHz - * signifies 500 MHz |
|---|---|---|---|---|---|---|---|---|---|
| 185. | 3,5-difluorophenyl | H, H | CH$_3$(CH$_2$)$_2$— (S) | —COR$_6$ | —CH(CH$_3$)$_2$ | OC(CH$_3$)$_3$ | — | — | 0.89 (t,3H); 1.31 (d,6H), 1.37 (m,2H), 1.55 (s,9H), 1.64 (m,2H), 3.59 (m,2H), 3.95 (m,2H), 4.45 (m,1H), 7.09 (d,2H), 7.12(t,1H), 8.49 (s,1H), 12.40 (s, 1H)*** |
| 186. | 3,5-difluorophenyl | H, H | CH$_3$(CH$_2$)$_2$— (S) | —COR$_6$ | —CH(CH$_3$)$_2$ | NR$_7$R$_8$ | CH$_3$, —(CH$_2$)$_2$-phenyl | — | 0.91 (m,3H) 1.22 (m,6H), 1.32 (m,2H); 1.69 (m,2H); 2.89 and 3.01 (2s,3H); 3.07-3.40 (m,2H); 3.71 (m,1H); 4.45-4.51 (2m,1H); 7.02 (m,2H) ; 7.18 (m,2H); 7.25 (m,2H); 7.35 (m,2H); 8.53 (m,1H); 12.25 (s,1H)*** |
| 187. | 2-methylthiophene | =O | CH$_3$(CH$_2$)$_2$— (S) | —COR$_6$ | —CH(CH$_3$)$_2$ | OCH$_3$ | — | −56° | 0.96 (t,3H); 1.36 (d,6H); 1.42 (m,2H); 1.87 (m,2H); 3.85 (s,3H); 4.07 (m,1H); 4.59 (m,1H); 7.38 (d,1H); 8.22 (d,1H); 8.26 (d,1H); 9.22 (d,1H); 12.68 (broad s,1H)*** |
| 188. | 3,5-difluorophenyl | H, H | CH$_3$(CH$_2$)$_2$— (S) | —COR$_6$ | 4-phenoxyphenyl-methyl (4-methylphenoxy-phenyl) | OCH$_3$ | — | — | 0.92 (t,3H); 1.32-1.39 (m,2H); 1.75 (m,2H); 3.75 (s,3N); 4.48 (m,1H); 7.06 (m,4H); 7.13 (m,3H); 7.24 (m,1H); 7.49 (m,2H); 7.55 (m,2H); 8.56 (m,1H); 12.77 (s,1H)*** |
| 189. | 3,5-difluorophenyl | OH, H(S) | CH$_3$(CH$_2$)$_2$— (S) | —COR$_6$ | 2-methylphenoxymethyl-benzyloxy | OCH$_3$ | — | −56° | 0.89 (t,3H); 1.29 (m,2H); 1.79 (m,2H); 3.63 (s,3H); 4.54 (m,1H); 5.13 (s,1H); 5.17 (s,2H); 6.62 (s,1H); 7.07 (t,1H); 7.23 (m,4H); 7.33 (m,6H); 7.43 (m,1H); 8.35 (d,1H); 12.68 (s,1H)s*** |

TABLE-continued (I)

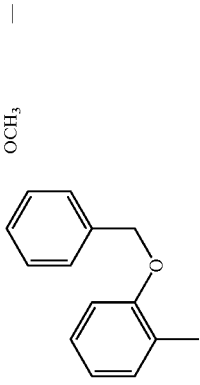

| Cpd. | R₁ | R₂, R'₂ | R₃ | R₄ | R₅ | R₆ | R₇, R₈ | alpha D (C = 1, MeOH) | NMR(DMSO d6 unless specified) * signifies 300 MHz.  signifies 360 MHz - * signifies 500 MHz |
|---|---|---|---|---|---|---|---|---|---|
| 190. | 3,5-difluorophenyl | OH, H(R) | CH₃(CH₂)₂— (S) | —COR₆ | 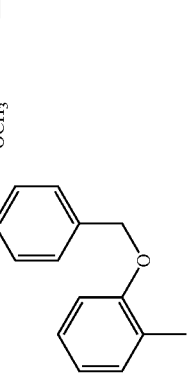 | OCH₃ | — | — | 0.94 (t,3H); 1.28-1.35 (2m,2H); 1.78 (m,2H); 3.65 (s,3H); 4.49 (m,1H); 5.13 (2s,3H); 6.47 (s,1H); 7.05 (t,1H); 7.21 (m,4H); 7.35 (m,6H); 7.45 (m,1H); 8.38 (d,1H); 12.70 (s,1H)*** |
| 191. | 3,5-difluorophenyl | 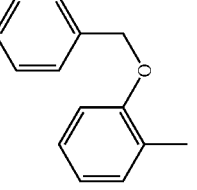 | CH₃(CH₂)₂— (S) | —COR₆ | 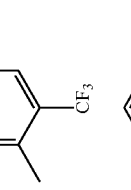 | OCH₃ | — | — | 0.99 (t,3H); 1.47 (m,2H); 1.80-1.86 (2m,2H); 3.64 (s,3H); 4.67 (m,1H); 5.19 (s,2H); 7.08 (t,1H); 7.24 (d,1H); 7.30-7.50 (m,8H); 7.78 (m,2H); 9.46 (broad s 1H); 12.87 (broad s 1H)*** |
| 192. | 3,5-difluorophenyl | H, H | CH₃(CH₂)₂— (S) | —COR₆ | 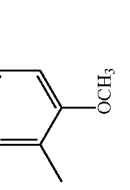 | OCH₃ | — | — | 0.98 (t,3H); 1.35-1.45 (m,2H); 1.75 (m,2H); 3.60 (m+s,5H); 3.50 (m,1H); 7.06 (d,2H); 7.15 (t,1H); 7.60 (d,1H); 7.77 (m,2H); 7.90 (d,1H); 8.55 (broad s 1H); 12.90 (s,1H)*** |
| 193. | 3,5-difluorophenyl | H, H | CH₃(CH₂)₂— (S) | —COR₆ | 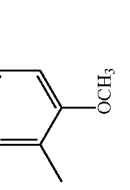 | OCH₃ | — | — | 0.97 (t,3H); 1.39 (m,2H); 1.75 (m,2H); 3.64 (m,2H); 3.81 (s,3H); 4.11 (s,3H); 4.51 (m,1H); 7.07 (m,3H); 7.17 (m,2H); 7.38 (d,1H); 7.48 (m,1H); 8.58 (broad s,1H); 12.75 (broad s 1H)*** |

TABLE-continued (I)

| Cpd. | R$_1$ | R$_2$, R'$_2$ | R$_3$ | R$_4$ | R$_5$ | R$_6$ | R$_7$, R$_8$ | alpha D (C = 1, MeOH) | NMR(DMSO d6 unless specified) * signifies 300 MHz.  signifies 360 MHz - * signifies 500 MHz |
|---|---|---|---|---|---|---|---|---|---|
| 194. | 3,5-difluorophenyl | H, H | CH$_3$(CH$_2$)$_2$— (S) | —COR$_6$ | 2-methylphenyl | OCH$_3$ | — | — | 0.94 (t,3H); 1.35 (m,1H); 1.40 (m,1H); 1.71 (m,2H); 2.17 (s,3H); 3.62 (m,2H); 3.73 (s3H); 4.47 (m,1H); 7.04 (d,2H); 7.15 (t,1H); 7.29 (broad s 2H); 7.36 (m,2H); 8.56 (broad d 1H); 12,78 (broad s 1H)*** |
| 195. | cyclopropyl-C(=O)— | | CH$_3$(CH$_2$)$_2$— (S) | —COR$_6$ | —CH(CH$_3$)$_2$ | OCH$_3$ | — | −28.5° | 0.94 (t,3H); 1.07 (m,2H); 1.19 (m,2H); 1.32 (d,6H); 1.37 (m,2H); 1.80 (m,2H); 2.86 (m,1H); 3.85 (s,3H); 4.03 (m,1H); 4.50 (m,1H); 8.80 (d,1H); 12.56 (broad s 1H)*** |
| 196. | 3,5-difluorophenyl | O=C(CH$_3$)— | CH$_3$(CH$_2$)$_2$— (S) | —COR$_6$ | benzyl (CH$_2$Ph) | OCH$_3$ | — | −71° | 0.94 (t,3H); 1.37 (m,2H); 1.79 (m,2H); 3.87 (s,3H); 4.54 (s,2H); 4.58 (m,1H); 7.29 (m,1H); 7.35 (m,4H); 7.75 (m,3H); 9.38 (m,1H); 12.66 (broad s 1H)*** |
| 197. | 3,5-difluorophenyl | H, H | CH$_3$(CH$_2$)$_2$— (S) | —COR$_6$ | 2-bromo-methylphenyl | OCH$_3$ | — | — | 0.95 (t,3H); 1.39-1.44 (2m,2H); 1.77 (m,2H);1,38and 1.43 (2m,2H); 1.75 (m,2H); 3.69 (m,2H); 3.81 (s,3H); 4.48 (m,1H); 7.15 (d,2H); 7.22 (t,1H); 7.45 (m,1H); 7.51 (m,2H); 7.79 (d,1H); 8.58 (broad s 1H); 12.89 (broad s 1H)*** |
| 198. | 3,5-difluorophenyl | H, H | CH$_3$(CH$_2$)$_2$— (S) | —COR$_6$ | —CH(CH$_3$)$_2$ | NR$_7$R$_8$ | H, —(CH$_2$)$_2$-morpholine | — | 0.93 (t,3H); 1.28 (d,6H); 1.38 (m,2H); 1.68 (m,2H); 2.50 (m,4H); 2.56 (m,2H); 3.45 (m,2H); 3.60 (m,6H); 4.28 (m,1H); 4.52 (m,1H); 7.06 (d,2H); 7.14 (t,1H); 7.73 (m,1H); 8.57 (d,1H); 12.30 (broad s 1H)*** |

TABLE-continued (I)

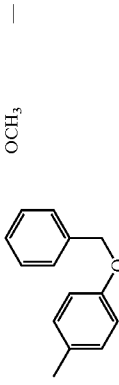

| Cpd. | R$_1$ | R$_2$, R'$_2$ | R$_3$ | R$_4$ | R$_5$ | R$_6$ | R$_7$, R$_8$ | alpha D (C = 1, MeOH) | NMR(DMSO d6 unless specified) * signifies 300 MHz.  signifies 360 MHz - * signifies 500 MHz |
|---|---|---|---|---|---|---|---|---|---|
| 199. | 3,5-difluorophenyl | H, H | CH$_3$(CH$_2$)$_2$— (S) | —COR$_6$ | 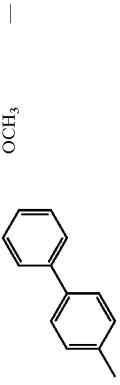 | OCH$_3$ | — | — | 0.94 (t,3H); 1.37-1.43 (2m,2H); 1.73 (m,2H); 3.60 (m,2H); 3.74 (s,3H); 4.50 (m,1H); 5.20 (s,2H); 7.06 (d,2H); 7.12 (m,3H); 7.36-7.50 (m,7H); 8.56 (d,1H); 12.76 (broad s 1H)*** |
| 200. | 3,5-difluorophenyl | H, H | CH$_3$(CH$_2$)$_2$— (S) | —COR$_6$ |  | OCH$_3$ | — | — | 0.93 (t,3H); 1.32-1,40 (m,2H); 1.70 (m,2H); 3.60 (m,2H); 3.78 (s,3H) ; 4.50 (m,1H); 7.03 (d,2H); 7.12 (t,1H); 7.40 (m,1H); 7.50 (m,2H); 7.53 (m,2H); 7.80 (m,4H); 8.58 (d,1H); 12.78 (broad s 1H)*** |
| 201. | (CH$_3$)$_2$CH— | OH, H(S) | CH$_3$(CH$_2$)$_2$— (S) | —COR$_6$ | 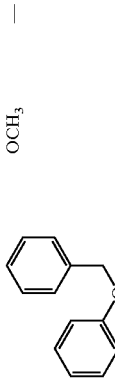 | OCH$_3$ | — | — | 0.93 (t,3H); 0.96 (s,9H); 1,40 (m,2H); 1.78 (m,2H); 3.62 (s,1H); 3.63 (s,3H); 4.59 (m,1H); 5.17 (s,2H); 5.65 (s,1H); 7.07 (m,1H); 7.21 (m,1H); 7.35 (m,6H); 7.44 (m,1H); 7.80 (d,1H); 12.62 (broad s 1H)*** |
| 202. | (CH$_3$)$_2$CH— | OH, H(S) | CH$_3$(CH$_2$)$_2$— (S) | —COR$_6$ | 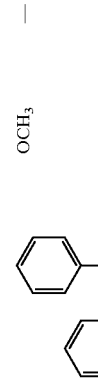 | OCH$_3$ | — | — | 0.78 (d,3H); 0.86 (d,3H); 0.97 (d,3H); 1,34 (m,2H); 1.78 (m,2H); 2,06 (m,1H); 3.66 (s,3H); 3.80 (s,1H); 3.59 (m,1H); 5.17 (s,2H); 5.54 (s,1H); 7.06 (m,1H); 7.20 (m,1H); 7.32 (m,6H); 7.42 (m,1H); 7.89 (d,1H); 12.66 (broad s 1H) |
| 203. | (CH$_3$)$_2$CH—CH$_2$— | OH, H(S) | CH$_3$(CH$_2$)$_2$— (S) | —COR$_6$ | | OCH$_3$ | — | — | 0.94 (d,6H); 1.32 (m,2H); 1.50 (m,2H); 1.80 (m,2H); 1.87 (m,2H) 3.78 (s,3H); 3.99 (m,1H); 3.62 (m,1H); 5.17 (s,2H); 5.60 (s,1H); 7.17 (t,1H); 7.20 (d,1H); 7.30 (m,6H); 7.42 (m,1H); 7.95 (d,1H); 12.61 (broad s 1H)*** |

TABLE-continued (I)

| Cpd. | R₁ | R₂, R'₂ | R₃ | R₄ | R₅ | R₆ | R₇, R₈ | alpha D (C = 1, MeOH) | NMR (DMSO d6 unless specified) * signifies 300 MHz.  signifies 360 MHz - * signifies 500 MHz |
|---|---|---|---|---|---|---|---|---|---|
| 204. | 3,5-difluorophenyl | H, H | CH₃(CH₂)₂— (S) | —COR₆ | —CH(CH₃)₂ | NR₇R₈ | CH₃, —CH₂—phenyl | — | 0.92 (t,3H); 1.24-1.29 (2d,6H); 1.40 (m,2H); 1.70 (m,2H); 2.86 and 2.93 (2s,3H); 3.40 (m,1H); 3.60 (m,2H); 4.50 (m,1H); 4.60 (s) and 4.72 (m) 2H; 7.08 (d,2H); 7.14(t,1H); 7.24 (d,1H); 7.39 (m,4H); 8.55 (d,1H); 12.35 (broad s 1H)*** |
| 205. | 3,5-difluorophenyl | H, H | CH₃(CH₂)₂— (S) | —COR₆ | —CH(CH₃)₂ | NR₇R₈ | CH₃, —CH₂—(2-pyridyl) | — | 0.92 (t,3H); 1.24 (d,6H); 1.32 and 1.41 (2m,2H); 1.68 (m,2H); 2.86 and 3.04 (2s,3H) 3.07-3.18 (m,2H); 3.36 (m,1H); 3.60 (m,2H); 3.84 (m,1H); 4.51 (m,1H); 7.03 (d,2H); 7.11 (t,1H); 7.2-7.4 (m,2H); 7.66 and 7.73 (2t,1H); 8.45-8.57 (m,2H); 12.27 (broad s 1H)*** |
| 206. | 3,5-difluorophenyl | H, H | CH₃(CH₂)₂— (S) | —COR₆ | 2-methyl-phenoxyphenyl | OCH₃ | — | — | 0.91 (t,3H); 1.33-1.40 (2m,2H); 1.67 (m,2H); 3.61 (m,2H); 3.70 (s,3H); 4.47 (m,1H); 6.93 (d,2H); 7.03 (t,3H); 7.14 (t,2H); 7.30 (t,1H); 7.39 (t,2H); 7.48 (t,1H); 7.54 (t,1H); 8.54 (d,1H); 12.78 (broad s 1H)*** |
| 207. | 3,5-difluorophenyl | H, H | CH₃(CH₂)₂— (S) | —COR₆ | 2-methyl-phenoxyphenyl | OCH₃ | — | — | 0.92 (t,3H); 1.32-1.41 (2m,2H); 1.67 (m,2H); 3.60 (s + m,5H); 3.66 (s,3H); 3.88 (s,3H); 4.48 (m,1H); 6.93 (d,1H); 7.03 (d,2H); 7.17 (m,3H); 8.56 (d,1H); 12.70 (broad s 1H)*** |
| 208. | 2-benzyloxy-3,5-difluorophenyl | OH, H | CH₃(CH₂)₂— (S) | —COR₆ | —CH(CH₃)₂ | OCH₃ | — | — | 0.92 (t,3H); 1.31 (d,6H); 1.35 (m,2H); 1.79 (m,2H); 3.86 (s,3H); 4.03 (m,1H); 4.59 (m,1H); 5.32 (d,2H); 5.32 (s,1H); 6.80 (m,1H); 7.01 (m,1H); 7.25 (m,1H); 7.40 (m,5H); 12.59 (broad s 1H)*** |

TABLE-continued (I)

| Cpd. | R₁ | R₂, R'₂ | R₃ | R₄ | R₅ | R₆ | R₇, R₈ | alpha D (C = 1, MeOH) | NMR(DMSO d6 unless specified) * signifies 300 MHz.  signifies 360 MHz - * signifies 500 MHz |
|---|---|---|---|---|---|---|---|---|---|
| 209. | 2-hydroxy-3,5-difluorophenyl | OH, H | CH₃(CH₂)₂— (S) | —COR₆ | —CH(CH₃)₂ | OCH₃ | — | — | 0.94 (t,3H); 1.33 (d,6H); 1.34 (m,2H); 1.82 (m,2H); 3.84 (s,3H); 4.04 (m,1H); 4.60 (m,1H); 5.30 (m,1H); 6.71 (m,1H); 6.80-7.20 (m,2H); 8.15 and 8.20 (2d,1H); 9.76 (broad s 1H); 12.57 (broad s 1H)*** |
| 210. | 3,5-difluorophenyl | H, H | CH₃(CH₂)₂— (S) | —COR₆ | —CH(CH₃)₂ | NR₇R₈ | CH₃, —(CH₂)₂OCH₃ | — | 0.93 (t,3H); 1.32 (d,6H); 1.34-1.41 (2m,2H); 1.70 (m,2H); 2.94 and 3.01 (2s,3H); 3.20 and 3.30 (2s,3H); 3.32-3.67 (4m,7H); 4.48 (m,1H); 7.04 (d,2H); 7.13 (t,1H); 8.55 (broad s 1H); 12.28 (s, broad s 1H)*** |
| 211. | 3,5-difluorophenyl | H, H | CH₃(CH₂)₂— (S) | —COR₆ | 2-methylbiphenyl | OCH₃ | — | — | 0.91 (t,3H); 1.33 (m,2H); 1.67 (m,2H); 3.61 (s,3H); 3.64 (m,2H); 4.43 (m,1H); 7.04 (m,2H); 7.14 (m,1H); 7.22 (m,2H); 7.28 (m,1H); 7.35 (m,2H); 7.48 (m,2H); 7.57 (m,1H); 8.60 (broad s 1H); 12.65 (broad s 1H)*** |
| 212. | 3,5-difluorophenyl | H, H | CH₃(CH₂)₂— (S) | —COR₆ | —CH(CH₃)₂ | NR₇R₈ | CH₃, —(CH₂)₂-(3,4-dimethoxyphenyl) | — | 0.87 (t,3H); 1.13 (2d,6H); 1.16-1.18 (2m,2H); 1.63 (m,2H); 2.80 (m,2H); 2.82 and 2.98 (2s,3H); 2.97 (m,1H); 3.15 (m,1H); 3.38 (m,1H); 3.60 (m,2H); 3.60-3.65-3.71 and 3.74 (4s,6H); 4.44 (m,1H); 6.58 (m,1H); 6.77 (m,1H); 6.86 (m,1H); 6.97 (m,2H); 7.06 (m,1H); 8.46 (broad s 1H); 12.23 (broad s 1H) |
| 213. | (CH₃)₃C— | OH, H(S) | CH₃(CH₂)₂— (S) | —COR₆ | 2-phenoxyphenyl | OCH₃ | — | — | 0.91 (t,3H); 0.93 (s,9H); 1.34 (m,2H); 1.77 (m,1H); 3.61 (d,2H); 3.71 (s,3H); 4.58 (m,1H); 5.65 (d,1H); 6.93 (d,2H); 7.03 (d,1H); 7.13 (t,1H); 7.29 (t,1H); 7.36 (t,2H); 7.48 (t,1H); 7.51 (d,1H); 7.86 (d,1H); 12.66 (broad s 1H)*** |

TABLE-continued (I)

| Cpd. | R₁ | R₂, R'₂ | R₃ | R₄ | R₅ | R₆ | R₇, R₈ | alpha D (C = 1, MeOH) | NMR(DMSO d6 unless specified) * signifies 300 MHz.  signifies 360 MHz - * signifies 500 MHz |
|---|---|---|---|---|---|---|---|---|---|
| 214. | 3,5-difluorophenyl | H, H | CH₃(CH₂)₂—(S) | —COR₆ | 2-methyl-6-(trifluoromethoxy)phenyl | OCH₃ | — | — | 0.93 (t,3H); 1.35-1.40 (2m,2H); 1.70 (m,2H); 3.60 (m,2H); 3.68 (s,3H); 4.50 (m,1H); 7.03 (d,2H); 7.12 (t,1H); 7.55 (m,2H); 7.63 (m,2H); 8.57 (broad s 1H); 12.88 (broad s 1H)*** |
| 215. | 3,5-difluorophenyl | OH, H(S) | CH₃(CH₂)₂—(S) | —COR₆ | 2-methyl-6-phenoxyphenyl | OCH₃ | — | — | 0.85 (t,3H); 1.26-1.29 (2m,2H); 1.75 (m,2H); 3.68 (s,3H); 4.47 (m,1H); 5.09 (s,1H); 6.58 (s,1H); 6.92 to 7.52 (7m,12H); 8.30 (broad s 1H); 12.68 (broad s 1H)*** |
| 216. | (CH₃)₃C— | OH, H(S) | CH₃(CH₂)₂—(S) | —COR₆ | 2-methylbiphenyl | OCH₃ | — | — | 0.91 (t,3H); 1.02 (s,9H); 1.35 (m,2H); 1.75 (m,2H); 3.58 (s,3H); 3.59 (s,1H); 4.54 (m,1H); 5.66 (s,1H); 7.20-7.57 (5m,9H); 7.83 (d,1H); 12.55 (broad s 1H)*** |
| 217. | 3,5-difluorophenyl | OH, H | CH₃(CH₂)₂—(S) | —COR₆ | 2-methylphenyl | NR₇R₈ | H, H | — | 0.91 (t,3H); 1.29 (m,2H); 1.79 (m,2H); 4.58 (m,1H); 5.15 (d,1H); 6.48 and 6.63 (2s,1H); 7.12 (m,3H); 7.42 (m,4H); 7.58 (m,1H); 7.59 (s,2H); 8.34 and 8.40 (2d,1H); 12.41 (broad s 1H)*** |
| 218. | 3,5-difluorophenyl | H, H | CH₃(CH₂)₂—(S) | —COR₆ | —CH(CH₃)₂ | O—CH₂—phenyl | — | — | 0.92 (t,3H); 1.25 (d,6H); 1.38 (m,2H); 3.05 (m,2H); 3.61 (m,2H); 3.88 (m,1H); 4.43 (m,1H); 4.51 (m,2H); 7.04 (d,2H); 7.15 (t,1H); 7.27 (m,1H); 7.36 (s,4H); 8.52 (d,1H); 12.55 (broad s 1H)*** |

| Cpd. | R₁ | R₂, R'₂ | R₃ | R₄ | R₅ | R₆ | R₇, R₈ | alpha D (C = 1, MeOH) | NMR(DMSO d6 unless specified) * signifies 300 MHz . ** signifies 360 MHz - *** signifies 500 MHz |
|---|---|---|---|---|---|---|---|---|---|
| 219. | (CH₃)₂CH— | OH, H(S) | CH₃(CH₂)₂— (S) | —COR₆ | 2-methyl-phenoxy-phenyl | OCH₃ | — | — | 0.80 (d,3H); 0.87 (t,3H); 0.90 (d,3H); 1.27 (m,2H); 1.70 (m,2H); 1.98 (m,1H); 3.65 (s,3H); 3.74 (m,1H); 5.48 (d,1H); 6.88 (d,2H); 6.97 (d,1H); 7.09 (t,1H); 7.24 (t,1H); 7.20 (m,2H); 7.30 (m,1H); 7.34 (d,1H); 7.85 (d,1H); 12.63 (s,1H)*** |
| 220. | 3,5-difluorophenyl | H, H | CH₃(CH₂)₂— (S) | —COR₆ | 2-methyl-phenoxy-phenyl | OCH₃ | — | — | 0.86 (t,3H); 1.32 (m,2H); 1.63 (m,2H); 3.55 (m,2H); 3.59 (s,3H); 4.43 (m,1H); 4.91 (s,2H); 6.83 (d,2H); 6.86 (m,1H); 6.99 (d,2H); 7.07 (m,1H); 7.18 (m,2H); 7.37 (t,1H); 7.40 (t,1H); 7.47 (t,1H); 7.57 (d,1H); 8.52 (d,1H); 12.62 (s,1H)*** |
| 221. | (CH₃)₃C— | OH, H(S) | CH₃(CH₂)₂— (S) | —COR₆ | 2-methyl-benzyloxy-phenyl | OCH₃ | — | — | 0.87 (t,3H); 0.90 (s,9H); 1.28 (m,2H); 1.70 (m,2H); 3.55 (s,1H); 3.59 (s,3H); 4.53 (m,1H); 4.91 (s,2H); 5.59 (d,1H); 6.83 (d,2H); 6.90 (t,1H); 7.22 (m,2H); 7.34 (d,1H); 7.40 (t,1H); 7.45 (t,1H); 7.59 (t,1H); 7.82 (d,1H)*** |
| 222. | (CH₃)₃C— | OH, H(S) | CH₃(CH₂)₂— (S) | —COR₆ | 2-methyl-(pyridinylmethoxy)-phenyl | OCH₃ | — | — | 0.96 (t,3N ; 0.99 (s,9H); 1.44 (m,2H); 1.77 (m,2H); 3.38 (s,3H); 3.64 (s,1H); 4.64 (m,1H); 5.26 (s,2H); 5.68 (d,1H); 7.12 (t,1H); 7.24 (d,1H); 7.34 (d,1H); 7.38 (m,1H); 7.44 (m,2H); 7.82 (t,1H); 7.90 (d,1H); 8.62 (d,1H); 12.68 (s,1H)*** |
| 223. | 3,5-difluorophenyl | H, H | CH₃(CH₂)₂— (S) | —COR₆ | 2-methyl-(pyridinylmethoxy)-phenyl | OCH₃ | — | — | 0.99 (t,3H); 1.46 (m,2H); 1.77 (m,2H); 3.63 (s,3H); 3.66 (m,2H); 4.54 (m,1H); 5.28 (s,2H); 7.10-7.48 (several m,9H); 7.83 (t,1H); 8.63 (m,2H); 12.80 (broad s 1H)*** |

TABLE-continued (I)

| Cpd. | R₁ | R₂, R'₂ | R₃ | R₄ | R₅ | R₆ | R₇, R₈ | alpha D (C = 1, MeOH) | NMR(DMSO d6 unless specified) * signifies 300 MHz .  signifies 360 MHz - * signifies 500 MHz |
|---|---|---|---|---|---|---|---|---|---|
| 224. | (CH₃)₃C— | OH, H(S) | CH₃(CH₂)₂— (S) | —COR₆ | 2-(trifluoromethyl)benzyloxy-o-tolyl | OCH₃ | — | — | 0.85 (t,3H); 0.91 (s,9H); 1.29 (m,2H); 1.68 (m,2H); 3.53 (s,3H); 3.56 (m,2H); 4.52 (m,1H); 5.24 (s,2H); 5.58 (d,1H); 7.05 (t,1H); 7.13 (d,1H); 7.36 (d,1H); 7.41 (t,1H); 7.54 (d,1H); 7.62 (t,1H); 7.73 (d,1H); 12.55 (s,1H)*** |
| 225. | (CH₃)₃C— | OH, H(S) | CH₃(CH₂)₂— (S) | —COR₆ | 2-fluorobenzyloxy-o-tolyl | OCH₃ | — | — | 0.87 (t,3H); 0.91 (s,9H); 1.28 (m,2H); 1.70 (m,2H); 3.56 (s,2H); 3.56 (s,3H); 4.54 (m,1H); 5.15 (s,2H); 5.60 (d,1H); 7.05 (t,1H); 7.20 (m,3H); 7.33 (m,3H); 7.39 (m,1H); 7.81 (d,1H); 12.54 (broad s 1H)*** |
| 226. | (CH₃)₃C— | OH, H(S) | CH₃(CH₂)₂— (S) | —COR₆ | 3-fluorobenzyloxy-o-tolyl | OCH₃ | — | — | 0.96 (t,3H); 0.99 (s,9H); 1.35 (m,2H); 1.80 (m,2H); 3.64 (d,1H); 3.65 (s,3H); 4.63 (m,1H); 5.23 (s,2H); 5.68 (d,1H); 7.12-7.22 (m,5H); 7.45 (m,3H); 7.92 (d,1H); 12.67 (broad s 1H)** |
| 227. | 3,5-difluorophenyl | H, H | CH₃(CH₂)₂— (S) | —COR₆ | 2-fluorobenzyloxy-o-tolyl | OCH₃ | — | — | 0.87 (t,3H); 1.32 (m,2H); 1.64 (m,2H); 3.57 (s,3H); 3.60 (m,2H); 4.43 (m,1H); 5.14 (s,2H); 6.98-7.40 (m,1H); 8.51 (d,1H); 12.63 (broad s 1H)*** |

TABLE-continued (I)

| Cpd. | R₁ | R₂, R'₂ | R₃ | R₄ | R₅ | R₆ | R₇, R₈ | alpha D (C=1, MeOH) | NMR(DMSO d6 unless specified) * signifies 300 MHz.  signifies 360 MHz - * signifies 500 MHz |
|------|-----|---------|-----|-----|-----|-----|---------|---------------------|---------------------------------------------------|
| 228. | 3,5-difluorophenyl | H, H | CH₃(CH₂)₂— (S) | —COR₆ | 3-fluorobenzyloxy-2-methylphenyl | OCH₃ | — | — | 0.95 (t,3H); 1.43 (m,2H); 1.71 (m,2H); 3.66 (m+s, 5H); 4.50 (m, 1H); 5.18 (s,2H); 7.06-7.19 (m,8H); 7.44 (m,3H); 8.64 (d,1H); 12.72 (broad s 1H)*** |
| 229. | 3,5-difluorophenyl | OH, H | CH₃(CH₂)₂— (S) | —COR₆ | pyridin-2-ylmethoxy-2-methylphenyl | OCH₃ | — | — | 0.83 (t,3H); 1.25 (m,2H); 1.69 (m,2H); 3.55 (s,3H); 4.45 (m,1H); 5.09 (m,1H); 5.16 (s,2H); 6.44 and 6.58 (2d,1H); 7.02 (t,1H); 7.14 (m,4H); 7.24-7.37 (m,4H); 7.33 (m,1H); 8.30 and 8.32 (2d,1H); 8.52 (s,1H); 12.63 and 12.71 (broad 2s 1H)*** |
| 230. | (CH₃)₃C— | OH, H(S) | CH₃(CH₂)₂— (S) | —COR₆ | 2-methylbenzyloxy-2-methylphenyl | OCH₃ | — | — | 0.97 (t,3H); 1.02 (s,9H); 1.36 (m,2H); 1.80 (m,2H); 2.30 (s,3H); 3.65 (s,3H); 3.67 (m,2H); 4.65 (m,1H); 5.18 (s,2H); 5.70 (d,1H); 7.10-7.50 (5m,8H); 7.96 (d,1H); 12.68 (broad s 1H)*** |
| 231. | 3,5-difluorophenyl | H, H | CH₃(CH₂)₂— (S) | —COR₆ | 2-methylbenzyloxy-2-methylphenyl | OCH₃ | — | — | 0.96 (t,3H); 1.39 (m,2H); 1.71 (m,2H); 2.36 (s,3H); 3.60 (s,3H); 3.62 (m,2H); 4.50 (m,1H); 5.16 (s,2H); 7.06-7.48 (6m,11H); 8.67 (d,1H); 12.77 (s,1H)*** |

TABLE-continued (I)

| Cpd. | R₁ | R₂, R'₂ | R₃ | R₄ | R₅ | R₆ | R₇, R₈ | alpha D (C = 1, MeOH) | NMR(DMSO d6 unless specified) * signifies 300 MHz.  signifies 360 MHz - * signifies 500 MHz |
|---|---|---|---|---|---|---|---|---|---|
| 232. | (CH₃)₃C— | OH, H(S) | CH₃(CH₂)₂— (S) | —COR₆ | 3-chloro-benzyloxy-2-methylphenyl group | OCH₃ | — | — | 0.95 (t,3H); 0.99 (s,9H); 1.37 (m,2H); 1.81 (m,2H); 3.64 (m,2H); 3.67 (s,3H); 4.63 (m,1H); 5.22 (s,2H); 5.71 (d,1H); 7.10 (t,1H); 7.22 (d,1H); 7.33 (d,1H); 7.40-7.50 (m,5H); 7.94 (d,1H); 12.62 (broad s 1H)*** |
| 233. | CF₃ | OH, H(S) | CH₃(CH₂)₂— (S) | —COR₆ | 3-fluoro-benzyloxy-2-methylphenyl group | OCH₃ | — | — | 0.96 (t,3H); 1.37 (m,2H); 1.82 (m,2H); 3.66 (s,3H); 4.60 (m,1H); 4.72 (m,1H); 5.23 (s,2H); 7.01-7.50 (2m,8H); 8.62 (d,1H); 12.86 (broad s 1H)*** |
| 234. | 3,5-difluorophenyl | H, H | CH₃(CH₂)₂— (S) | CH₃ | —COR₆ | NR₇R₈ | CH₃, CH₃ | — | 0.96 (t,3H); 1.40 (m,2H); 1.72 (m,2H); 2.32 (s,3H); 3.06 (s,6H); 3.62 (m,2H); 4.52 (m,1H); 7.08 (d,2H); 7.16 (t,1H); 8.58 (d,1H); 12.42 (broad s 1H)*** |
| 235. | 3,5-difluorophenyl | H, H | CH₃(CH₂)₂— (S) | CH₃ | —COR₆ | NR₇R₈ | 2-methoxyphenethyl | — | 0.85 (t,3H); 1.27 (m,2H); 1.62 (m,2H); 2.41 (s,3H); 2.78 (t,2H); 3.37 (t,2H); 3.55 (m,2H); 3.78 (s,3H); 4.43 (m,1H); 6.87 (t,1H); 7.08 (m,3H); 7.11 (m,2H); 7.20 (t,1H); 7.95 (broad s 1H); 8.51 (d,1H); 12.38 (broad s 1H) |
| 236. | 3,5-difluorophenyl | H, H | CH₃(CH₂)₂— (S) | H | —COR₆ | OCH₃ | — | — | 0.93 (t,3H); 1.30 and 1.41 (2m,2H); 1.70 (m,2H); 3.61 (m,2H); 3.85 (s,3H); 4.53 (m,1H); 7.04 (d,2H); 7.17 (t,1H); 8.21 (s,1H); 8.63 (d,1H); 12.82 (broad s 1H)*** |

TABLE-continued (I)

| Cpd. | R₁ | R₂, R'₂ | R₃ | R₄ | R₅ | R₆ | R₇, R₈ | alpha D (C = 1, MeOH) | NMR(DMSO d6 unless specified) * signifies 300 MHz.  signifies 360 MHz - * signifies 500 MHz |
|---|---|---|---|---|---|---|---|---|---|
| 237. | (CH₃)₃C— | OH, H(S) | CH₃(CH₂)₂— (S) | H | —COR₆ | NR₇R₈ | —(CH₂)₂-phenyl | — | 0.91 (t,3H); 0.95 (s,9H); 1.32 and 1.35 (2m,2H); 1.74 (m,2H); 2.90 (m,2H); 3.18 (broad s 3H); 3.60 (d,1H); 3.71 (m,2H); 3.61 (m,1H); 5.63 (d,1H); 7.22-7.35 (m,5H); 7.90 (broad s 1H) |
| 238. | (CH₃)₃C— | OH, H(S) | CH₃(CH₂)₂— (S) | —COR₆ | 2-chlorobenzyloxy-o-tolyl | OCH₃ | — | — | 0.96 (t,3H); 1.14 (s,9H); 1.39 (m,2H); 1.82 (m,2H); 3.65 (s,3H); 3.67 (s,1H); 4.64 (m,1H); 5.27 (s,2H); 5.73(d,1H); 7.16 (m,1H); 7.28 (d,1H); 7.40-7.50(4m,6H); 8.01 (d,1H); 12.70 (s, broad 1H)*** |
| 239. | (CH₃)₃C— | OH, H(S) | CH₃(CH₂)₂— (S) | —COR₆ | 2,6-difluorobenzyloxy-o-tolyl | OCH₃ | — | — | 0.94 (t,3H); 0.97 (s,9H); 1.34 (m,2H); 3.62 (s,3H); 3.63 (s,1H); 5.87 (m,2H); 5.15 (s,2H); 7.15 (m,3H); 7.41 (d,1H); 7.50 (m,2H); 7.69 (d,1H); 12.67 (s broad 1H)*** |
| 240. | (CH₃)₃C— | OH, H(S) | CH₃(CH₂)₂— (S) | —COR₆ | 3,5-difluorobenzyloxy-o-tolyl | OCH₃ | — | — | 0.97 (t,2H); 0.99 (s,9H); 1.39 (m,2H); 1.80 (m,2H); 3.65 (s,3H); 3.66 (s,1H); 4.63 (m,1H); 5.24 (s,2H); 5.70 (d,1H); 7.05-7.27 (3m,5H); 7.45-7.49 (2m,2H); 7.93 (d,1H); 12.70 (s broad 1H)*** |
| 241. | (CH₃)₃C— | OH, H(S) | CH₃(CH₂)₂— (S) | —COR₆ | 2,3-difluorobenzyloxy-o-tolyl | OCH₃ | — | — | 0.87 (t,3H); 0.91 (s,9H); 1.30 (m,2H); 1.73 (m,2H); 3.56 (2s,4H); 4.54 (m,1H); 5.19 (s,2H); 5.60 (d,1H); 7.06 (m,1H); 7.16 (m,2H); 7.23 (d,1H); 7.32-7.41 (m,3H); 7.82 (d,1H); 12.70 (s broad 1H)*** |

TABLE-continued (I)

| Cpd. | R₁ | R₂, R'₂ | R₃ | R₄ | R₅ | R₆ | R₇, R₈ | alpha D (C = 1, MeOH) | NMR(DMSO d6 unless specified) * signifies 300 MHz.  signifies 360 MHz - * signifies 500 MHz |
|---|---|---|---|---|---|---|---|---|---|
| 242. | (CH₃)₃C— | OH, H(S) | CH₃(CH₂)₂— (S) | —COR₆ | trans-2-phenylcyclopropyl | OCH₃ | — | — | 0.87 (t,3H); 0.91 (s,9H); 1.27 (m,2H); 1.45 (m,3H); 1.69 (m,1H); 2.32 (m,1H); 3.13 (m,1H); 3.56 (d,1H); 3.70 (s,3H); 4.52 (m,1H); 5.57 (d,1H); 7.19 (m,3H); 7.29 (m,2H); 7.80 (d,1H); 12.47 (s broad 1H)*** |
| 243. | 3,5-difluorophenyl | H, H | CH₃(CH₂)₂— (S) | —COR₆ | trans-2-phenylcyclopropyl | OCH₃ | — | — | 0.95 (t,3H); 1.35-1.41 (m,2H); 1.51 (M,1H); 1.72 (m,3H); 2.38 (m,1H); 3.20 (m,1H); 3.63 (m,2H); 3.76 (s,3H); 7.26 (m,3H); 7.33 (m,2H); 8.54 (s broad 1H); 12.65 (s broad 1H)*** |
| 244. | 3,5-difluorophenyl | H, H | CH₃(CH₂)₂— (S) | —COR₆ | 2-benzyloxy-3-fluoro-6-methylphenyl | OCH₃ | — | — | 0.94 (t,3H); 1.39 (m,2H); 1.70 (m,2H); 3.62 (m+s,5H); 4.48 (m,1H); 4.91 (s,2H); 7.04 (d,2H); 7.12 (m,3H); 7.22 (m,5H); 7.40 (m,1H); 8.57 (d broad 1H); 12.77(s broad 1H)*** |
| 245. | (CH₃)₃C— | OH, H(S) | CH₃(CH₂)₂— (S) | —COR₆ | 2-benzyloxy-3-fluoro-6-methylphenyl | OCH₃ | — | — | 0.96 (t,3H); 0.98 (s,9H); 1.39 (m,2H); 1.80 (m,2H); 3.65 (m,1H); 3.66 (s,3H); 4.64 (m,1H); 4.95 (s,2H); 5.65 (s,1H); 7.15 (m,2H); 7.27 (m,5H); 7.45 (m,1H); 7.91 (d,1H); 12.70 (s broad 1H)*** |

TABLE-continued (I)

| Cpd. | R₁ | R₂, R'₂ | R₃ | R₄ | R₅ | R₆ | R₇, R₈ | alpha D (C = 1, MeOH) | NMR(DMSO d6 unless specified) * signifies 300 MHz .  signifies 360 MHz - * signifies 500 MHz |
|---|---|---|---|---|---|---|---|---|---|
| 246. | (CH₃)₃C— | OH, H(S) | CH₃(CH₂)₂— (S) | —COR₆ | F—(2,5-difluorobenzyl-O-2-methylphenyl) | OCH₃ | — | — | 0.95 (t,3H); 0.98 (s,9H); 1.37 (m,2H); 1.80 (m,2H); 3.63 (d+s,5H); 4.61 (m,1H); 5.22 (s,2H); 5.68 (d,1H); 7.12 (t,1H); 7.16 (m,1H); 7.29 (m,3H); 7.40 (d,1H); 7.50 (m,1H); 7.89 (d,1H); 12.65 (s broad 1H)*** |
| 247. | 3,5-difluorophenyl | OH, H | CH₃(CH₂)₂— (S) | H | —COR₆ | NR₇R₈ | CH₃, (CH₂)₂-phenyl | — | 082 (t,3H); 1.16-1.28 (m,2H); 1.67 (m,2H); 2.86 (s broad 2H); 3.29 (sbroad 3H); 3.66 (s broad2H); 4.52(m,1H); 5.08 (2d,1H); 6.40 et 6.55 (2d,1H); 7.09-7.28 (3m,8H); 7.60 (sbroad 1H); 8.27 et 8.34 (2d,1H); 12.44 (s broad1H)**** |

In the table (S) or (R) in the columns "R₃" and "R₃, R'₂" indicate the stereochemistry of the asymmetric carbon, bearing R₃ or R'₂ in the formula (I). However, it is understood that, the indication (S) or (R) does not relate to the case in which R₂ and R'₂ taken together form an oxo group.

In the table (S) or (R) in the columns "$R_3$" and "$R_2$, $R'_2$" indicate the stereochemistry of the asymmetric carbon, bearing $R_3$ or $R'_2$ in the formula (I). However, it is understood that, the indication (S) or (R) does not relate to the case in which $R_2$ and $R'_2$ taken together form an oxo group.

The compounds of the invention were subjected to pharmacological tests which showed their advantage as active substances in therapy.

They were tested in particular for their inhibitory effects on the production of β-amyloid peptide (β-A4).

β-Amyloid peptide (β-A4) is a fragment of a larger precursor protein called APP (amyloid precursor protein). The latter is produced and is present in various cells of human or animal tissue. However its cleavage in cerebral tissue by protease-type enzymes leads to the formation of the β-A4 peptide, which accumulates in the form of an amyloid plaque. The two proteases responsible for producing the amyloid peptide are known by the name of beta- and gamma-secretases (Wolfe M S, Secretase targets for Alzheimer's disease: identification and therapeutic potential, J Med. Chem. 2001 Jun. 21; 44 (13): 2039-60).

It has however been demonstrated that this gradual deposition of the β-A4 peptide is neurotoxic and might play an important role in Alzheimer's disease.

Accordingly, the compounds of the present invention, as an inhibitor of the production of the β-amyloid peptide (β-A4) by inhibition of gamma-protease, can be used in the treatment of pathologies such as senile dementia, Alzheimer's disease, Down's syndrome, Parkinson's disease, amyloid angiopathy and/or cerebrovascular disorders.

The tests were conducted in accordance with the protocol described below.

For the β amyloid cellular test, the CHO—K1 line coexpressing the CT100 of APP and PS1 M146L clone 30-12 is used. The line targets the inhibition of gamma-secretase. Presenilin is linked to gamma-secretase activity (Wolfe M S, Haass C., The Role of presenilins in gamma-secretase activity, J Biol Chem. 2001 Feb. 23; 276(8): 5413-6) and its coexpression with the amyloid protein or its N-terminal fragment causes an increase in secretion of the peptide A1-42 (β-A4), thereby generating a pharmacological tool which allows inhibition by the compounds of formula (I) of the production of the β-A4 peptide to be evaluated. 96-well culture plates are inoculated with $1\times10^5$ cells per well in 150 µl of incubation medium. The presence of a minimum percentage (1.3% final) of serum allows cellular adhesion to the plastic after 2.3 hours of incubation at 37° C., in the presence of 5% $CO_2$. The products (15 µl) are tested at 10 µM DMSO 1% final and are incubated for 24-25 h at 37° C. in the presence of 5% $CO_2$ and 100% humidity. After this 24-25 h incubation, the cellular supernatants (100 µl) are transferred to ELISA plates, treated with the capture antibody 6E10 (6E10, epitope: aal-17, INTERCHIM/SENETEK 320/10, to determine the amount of amyloid peptides secreted by the cells in the presence of compounds according to the invention. A series of synthetic control peptide, "peptide 1-40", at 5 and 10 ng/ml is treated in parallel. The ELISA plates are incubated overnight at 4° C.

The quantity of bound peptide is detected indirectly in the presence of a competitor which corresponds to the truncated peptide, peptide 1-28 coupled to biotin, which is then detected with streptavidin coupled to alkaline phosphatase. The substrate, p-Nitrophenyl Phosphate (pNPP FAST p-nitrophenyl phosphate, Sigma N2770), gives a yellow, soluble reaction product which can be read at 405 nm. The reaction is stopped with 0.1M EDTA solution. For this purpose, following binding the amyloid peptide in the ELISA plate, 50 µl of biotinylated peptide 1-28 are added to 100 µl of cellular supernatant and incubated for 30 minutes at ambient temperature. The ELISA plates are then washed 3 times. After drying by inversion on absorbent paper, 100 µl of streptavidin-alkaline phosphatase (Interchim/Jackson ImmunoResearch Laboratories 016-050-084) are added per well and incubated for 1 hour at ambient temperature. The plates are washed again and then the alkaline phosphatase substrate (pNPP 1 mg/ml) is added in an amount of 100 µl per well. After 30 minutes of incubation at ambient temperature the reaction is stopped by adding 100 µl per well of 0.1M EDTA and reading is carried out 405 nm.

The compounds of formula (I) according to the present invention showed an IC50 (50% inhibitory concentration) of less than 500 nM, more particularly less than 100 nM.

The results of biological tests show that the compounds are inhibitors of the formation of the β-amyloid peptide (β-A4).

Accordingly these compounds can be employed in the treatment of pathologies in which a β-amyloid peptide (β-A4) formation inhibitor provides a therapeutic benefit. In particular, such pathologies include but not limited to senile dementia, Alzheimer's disease, Down's syndrome, Parkinson's disease, amyloid angiopathy and cerebrovascular disorders.

The use of the compounds according to the invention for preparing a medicament intended for treating the abovementioned pathologies forms an integral part of the invention.

The invention further provides medicaments which comprise a compound of formula (I), or an addition salt thereof with a pharmaceutically acceptable acid or a hydrate or a solvate of the compound of formula (I). These medicaments find their use in therapy, in particular, in the treatment of the abovementioned pathologies.

Another aspect of the present invention relates to pharmaceutical compositions comprising as active principle at least one compound according to the invention. These pharmaceutical compositions comprise an effective dose of a compound according to the invention, or of a pharmaceutically acceptable salt, hydrate or solvate of the said compound, and, optionally, one or more pharmaceutically acceptable excipients.

The said excipients are selected, according to the pharmaceutical form and the desired mode of administration, from the customary excipients which are known to the person skilled in the art.

In the pharmaceutical compositions of the present invention for oral, sublingual, subcutaneous, intramuscular, intravenous, topical, local, intratracheal, intranasal, transdermal or rectal administration the active principle of formula (I) above, or where appropriate its salt, solvate or its hydrate can be administered in unit form for administration, as a mixture with conventional pharmaceutical excipients, to animals and to human beings for the prophylaxis or treatment of the above diseases or disorders.

The appropriate unit forms for administration embrace the forms for oral administration such as tablets, soft or hard gelatin capsules, powders, granules, chewing gums and oral solutions or suspensions, the forms for sublingual, buccal, intratracheal, intraocular or intranasal administration or for administration by inhalation, the forms for subcutaneous, intramuscular or intravenous administration and the forms for rectal or vaginal administration. For topical application the compounds according to the invention can be used in creams, ointments or lotions.

By way of example, a unit for administration of a compound according to the invention in tablet form may comprise the following components:

| | |
|---|---|
| Compound according to the invention | 50.0 mg |
| Mannitol | 223.75 mg |
| Croscaramellose sodium | 6.0 mg |
| Corn starch | 15.0 mg |
| Hydroxypropyl-methylcellulose | 2.25 mg |
| Magnesium stearate | 3.0 mg |

In order to obtain the desired therapeutic or prophylactic effect, the dose of active principle may vary between 0.1 mg and 200 mg per kg of body weight per day. Although these dosages are average-situation examples, there may be particular cases in which higher or lower dosages are appropriate: such dosages are likewise part of the invention. In accordance with customary practice, the dosage appropriate to each patient is determined by the doctor in accordance with the mode of administration, the weight and the response of the said patient.

Each unit dose can contain from about 0.1 to about 1000 mg, preferably from about 0.1 to about 500 mg, of active principle in combination with one or more pharmaceutical excipients. This unit dose can be administered from 1 to 5 times per day in order to administer a daily dose of from about 0.5 to about 5000 mg, preferably from about 0.5 to about 2500 mg.

There may be particular cases in which higher or lower dosages are appropriate; such dosages are not outside the scope of the invention. In accordance with customary practice, the dosage appropriate to each patient is determined by the doctor in accordance with the mode of administration, the weight and the response of the said patient.

In another of its aspects the present invention likewise relates to a method of treating the pathologies indicated above which comprises administering a compound according to the invention, a pharmaceutically acceptable salt or a hydrate of the said compound.

What is claimed is:

1. A method of treating senile dementia, comprising administering to a patient in need of said treatment a compound of formula (I), including in the form of a pharmaceutically acceptable base or salt:

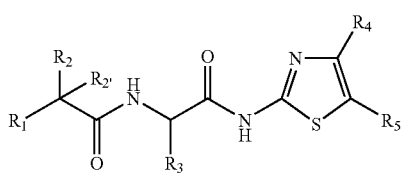

(I)

wherein $R_1$ is:

$C_{1-6}$ alkyl optionally substituted by one or two substituents selected from hydroxyl, trifluoromethyl, $C_{1-6}$ alkoxy, $C_{1-6}$ thioalkyl, thiophene or phenyl; or $C_{3-7}$ cycloalkyl, thiophene, benzothiophene, pyridinyl, furanyl or phenyl;

said phenyl being optionally substituted by one to three substituents selected from halogen, $C_{1-6}$ alkyl, $C_{1-6}$ alkoxy, hydroxyl, methylenedioxy, phenoxy or benzyloxy;

$R_2$ and $R'_2$ are independently of one another selected from: hydrogen, halogen, hydroxyl, $C_{1-3}$ alkoxy, $C_{1-3}$ alkyl, $C_{3-7}$ cycloalkyl, or O—C(O)—$C_{1-6}$ alkyl; or $R_2$ and $R'_2$ taken together form an oxo group;

$R_3$ is:

hydrogen or $C_{1-6}$ alkyl optionally substituted by hydroxyl or $C_{1-3}$ alkoxy;

$R_4$ and $R_5$ are independently of one another selected from:

hydrogen, $C_{1-7}$ alkyl optionally substituted by $C_{3-7}$ cycloalkyl or phenyl; or $C_{3-7}$ cycloalkyl, phenyl, naphthyl or —C(X)$R_6$;

said $C_{3-7}$ cycloalkyl and phenyl being optionally substituted by one or more groups selected from halogen, hydroxyl, $C_{1-3}$ alkyl, $C_{1-3}$ alkoxy, phenyl, phenoxy or benzyloxy;

provided that at least one of $R_4$ or $R_5$ is —C(X) $R_6$;

wherein

X is oxygen or sulfur;

$R_6$ is $C_{1-6}$ alkoxy, hydroxyl or —$NR_7R_8$;

and wherein $R_7$ and $R_8$ are independently of one another selected from:

hydrogen, $C_{1-6}$ alkyl optionally substituted by $C_{3-7}$ cycloalkyl, $C_{3-7}$ cycloalkenyl, phenyl or pyridinyl; or $C_{3-7}$ cycloalkyl, $C_{1-6}$ alkoxy or phenyl;

said $C_{3-7}$ cycloalkyl and phenyl being optionally substituted by $C_{1-3}$ alkyl, hydroxyl, $C_{1-3}$ alkoxy or halogen; or $R_7$ and $R_8$ taken together with the nitrogen atom to which they are attached form aziridine, azetidine, pyrrolidine, piperidine or morpholine.

2. The method as set forth in claim 1, wherein in the compound of formula (I)

$R_1$ is:

$C_{1-5}$ alkyl, optionally substituted by one or two substituents selected from hydroxyl, $C_{1-4}$ thioalkyl, thiophene or phenyl; or $C_{4-7}$ cycloalkyl, furanyl, thiophene, benzothiophene, pyridinyl or phenyl; said phenyl being optionally substituted by one or two substituents selected from halogen, hydroxyl, benzyloxy or methylenedioxy;

$R_2$ and $R'_2$ are independently of one another selected from: hydrogen, halogen, hydroxyl, $C_{1-3}$ alkyl, $C_{3-7}$ cycloalkyl, $C_{1-3}$ alkoxy, O—C(O—$C_{1-4}$ alkyl; or $R_2$ and $R'_2$ taken together form an oxo group;

$R_3$ is:

$C_{1-4}$ alkyl, optionally substituted by $C_{1-3}$ alkoxy;

$R_4$ and $R_5$ are independently of one another selected from:

hydrogen, $C_{1-7}$ alkyl, optionally substituted by phenyl or $C_{3-7}$ cycloalkyl; or $C_{3-7}$ cycloalkyl, phenyl, naphthyl or —C(X) $R_6$; said phenyl being optionally substituted by one or two groups selected from $C_{1-3}$ alkyl, hydroxyl, $C_{1-3}$ alkoxy, phenoxy or benzyloxy;

provided that at least one of $R_4$ or $R_5$ is —C(X) $R_6$;

wherein

X is oxygen;

$R_6$ is $C_{1-6}$ alkoxy, hydroxyl or —$NR_7R_8$;

$R_7$ and $R_8$ are independently of one another selected from:

hydrogen, $C_{1-3}$ alkyl, optionally substituted by $C_{3-7}$ cycloalkenyl, phenyl or pyridinyl; or $C_{1-3}$ alkoxy or $C_{3-6}$ cycloalkyl;

or $R_7$ and $R_8$ taken together with the nitrogen atom to which they are attached form azetidine, piperidine or morpholine.

3. The method as set forth in claim 1, wherein in the compound of formula (I)

$R_1$ is:

$C_{1-6}$ alkyl optionally substituted by one or two substituents selected from hydroxyl, $C_{1-6}$ alkoxy, $C_{1-6}$ thioalkyl, trifluoromethyl, thiophene or phenyl; or $C_{3-7}$ cycloalkyl, thiophene, benzothiophene, pyridinyl, furanyl or phenyl;

said phenyl being optionally substituted by one to three substituents selected from halogen, $C_{1-6}$ alkyl, $C_{1-6}$ alkoxy, hydroxyl, methylenedioxy, phenoxy or benzyloxy;

$R_2$ and $R'_2$ are independently of one another selected from:

hydrogen, halogen, hydroxyl, $C_{1-3}$ alkoxy, $C_{1-3}$ alkyl, $C_{3-7}$ cycloalkyl, O—C(O)—$C_{1-6}$ alkyl; or $R_2$ and $R'_2$ taken together form an oxo group;

$R_3$ is:

hydrogen or $C_{1-6}$ alkyl optionally substituted by hydroxyl or $C_{1-3}$ alkoxy;

$R_4$ and $R_5$ are independently of one another selected from:

hydrogen, $C_{1-7}$ alkyl optionally substituted by $C_{3-7}$ cycloalkyl or phenyl; or $C_{3-7}$ cycloalkyl, phenyl, naphthyl or —C(X)$R_6$;

said $C_{3-7}$ cycloalkyl and phenyl being optionally substituted by one or more groups selected from halogen, hydroxyl, $C_{1-3}$ alkyl, $C_{1-3}$ alkoxy, phenyl, phenoxy or benzyloxy;

provided that at least one of $R_4$ or $R_5$ is —C(X)$R_6$; wherein X is oxygen or sulfur;

$R_6$ is $C_{1-6}$ alkoxy, hydroxyl or —N$R_7R_8$; and wherein $R_7$ and $R_8$ are independently of one another selected from:

hydrogen, $C_{1-6}$ alkyl optionally substituted by $C_{3-7}$ cycloalkyl, $C_{3-7}$ cycloalkenyl, phenyl or pyridinyl; or $C_{3-7}$ cycloalkyl, $C_{1-6}$ alkoxy or phenyl;

said $C_{3-7}$ cycloalkyl and phenyl being optionally substituted by $C_{1-3}$ alkyl, hydroxyl, $C_{1-3}$ alkoxy or halogen; or $R_7$ and $R_8$ taken together with the nitrogen atom to which they are attached form aziridine, azetidine, pyrrolidine, piperidine or morpholine.

4. The method as set forth in claim 1, wherein in the compound of formula (I)

$R_1$ is $C_{1-4}$ alkyl or phenyl substituted by two fluorine atoms;

$R_2$ is hydroxyl and $R'_2$ is hydrogen;

$R_3$ is $C_{1-4}$ alkyl; and

X is oxygen.

5. The method as set forth in claim 2, wherein in the compound of formula (I)

$R_1$ is $C_{1-4}$ alkyl or phenyl substituted by two fluorine atoms;

$R_2$ is hydroxyl and $R'_2$ is hydrogen;

$R_3$ is $C_{1-4}$ alkyl; and

X is oxygen.

6. The method as set forth in claim 3, wherein in the compound of formula (I)

$R_1$ is $C_{1-4}$ alkyl or phenyl substituted by two fluorine atoms;

$R_2$ is hydroxyl and $R'_2$ is hydrogen;

$R_3$ is $C_{1-4}$ alkyl; and

X is oxygen.

* * * * *